(12) United States Patent
Meyers et al.

(10) Patent No.: US 6,608,111 B1
(45) Date of Patent: Aug. 19, 2003

(54) METHOD FOR TREATING OR PREVENTING PROSTATIC CONDITIONS

(75) Inventors: Cal Y. Meyers, Carbondale, IL (US); William J. Banz, Carterville, IL (US); Stuart R. Adler, Creve Coeur, MO (US); Todd A. Winters, Murphysboro, IL (US); Yuqing Hou, Carbondale, IL (US); Walter B. Dandliker, La Jolla, CA (US)

(73) Assignee: Southern Illinois University Office of Research, Development and Administration, Carbondale, IL (US)

(*) Notice: Subject to any disclaimer, the term of this patent is extended or adjusted under 35 U.S.C. 154(b) by 0 days.

(21) Appl. No.: 09/338,823

(22) Filed: Jun. 23, 1999

Related U.S. Application Data

(60) Provisional application No. 60/090,344, filed on Jun. 23, 1998.

(30) Foreign Application Priority Data

Jun. 22, 1999 (WO) .............................. PCT/US99/13940

(51) Int. Cl.[7] .............................................. A61K 31/19
(52) U.S. Cl. ....................................... 514/570; 514/569
(58) Field of Search ................................ 514/569, 570

(56) References Cited

U.S. PATENT DOCUMENTS

| | | | | |
|---|---|---|---|---|
| 4,634,695 A | | 1/1987 | Torelli et al. ................ 514/178 |
| 4,729,999 A | * | 3/1988 | Young ........................ 514/227 |
| 4,874,891 A | | 10/1989 | Covey et al. ................ 560/256 |
| 4,894,373 A | * | 1/1990 | Young ........................ 514/227 |
| 5,043,332 A | | 8/1991 | Teutsch et al. ............. 514/173 |
| 5,134,136 A | | 7/1992 | Kirsch et al. ............... 514/182 |
| 5,189,212 A | | 2/1993 | Ruenitz ....................... 562/468 |
| 5,344,826 A | | 9/1994 | Covey et al. ................ 514/167 |
| 5,420,161 A | | 5/1995 | Meyers ....................... 514/569 |
| 5,478,862 A | | 12/1995 | Peters et al. ................ 514/520 |
| 5,491,136 A | | 2/1996 | Peet et al. ................... 514/172 |
| 5,550,107 A | | 8/1996 | Labrie .......................... 514/11 |
| 5,631,249 A | | 5/1997 | Labrie et al. ............... 514/182 |
| 5,702,752 A | | 12/1997 | Gugger et al. |
| 5,773,477 A | | 6/1998 | MacLean et al. .......... 514/648 |
| 5,792,503 A | | 8/1998 | Gugger et al. |
| 5,798,348 A | | 8/1998 | Alemany ..................... 514/182 |
| 5,821,254 A | * | 10/1998 | Sporn et al. ................ 514/559 |
| 5,840,735 A | | 11/1998 | Labrie et al. ............... 514/320 |
| 5,843,934 A | | 12/1998 | Simpkins .................... 514/182 |
| 5,846,976 A | * | 12/1998 | Batchelor et al. .......... 514/284 |
| 5,856,340 A | | 1/1999 | Palkowitz ................... 514/324 |
| 6,033,714 A | | 3/2000 | Gugger et al. |
| 6,171,638 B1 | | 1/2001 | Gugger et al. |
| 6,261,565 B1 | | 7/2001 | Empie et al. |
| 6,391,308 B1 | | 5/2002 | Empie et al. |
| 6,391,309 B1 | | 5/2002 | Empie et al. |
| 6,391,310 B1 | | 5/2002 | Empie et al. |
| 6,395,279 B1 | | 5/2002 | Empie et al. |
| 6,399,072 B1 | | 6/2002 | Empie et al. |

FOREIGN PATENT DOCUMENTS

| | | |
|---|---|---|
| CH | 261123 | 9/1949 |
| FR | 941289 | 1/1949 |
| GB | 652003 | 4/1951 |
| WO | WO 97/07811 A1 | 3/1997 |

OTHER PUBLICATIONS

Biosis Abstract, AN 1986:126038, Geller et al. 1986.*
Medline Abstract, AN95042191, Kramer, 1995.*

(List continued on next page.)

*Primary Examiner*—Russell Travers
*Assistant Examiner*—Shengiun Wang
(74) *Attorney, Agent, or Firm*—Senniger, Powers, Leavitt & Roedel

(57) ABSTRACT

Provided is a method comprising administering (+)-Z-bisdehydrodoisynolic acid to a patient for treating, inhibiting or delaying the onset of prostatic conditions including prostatitis, benign prostatic hypertrophy and prostate cancer without accompanying feminizing effects.

5 Claims, 6 Drawing Sheets

OTHER PUBLICATIONS

Figure 1:
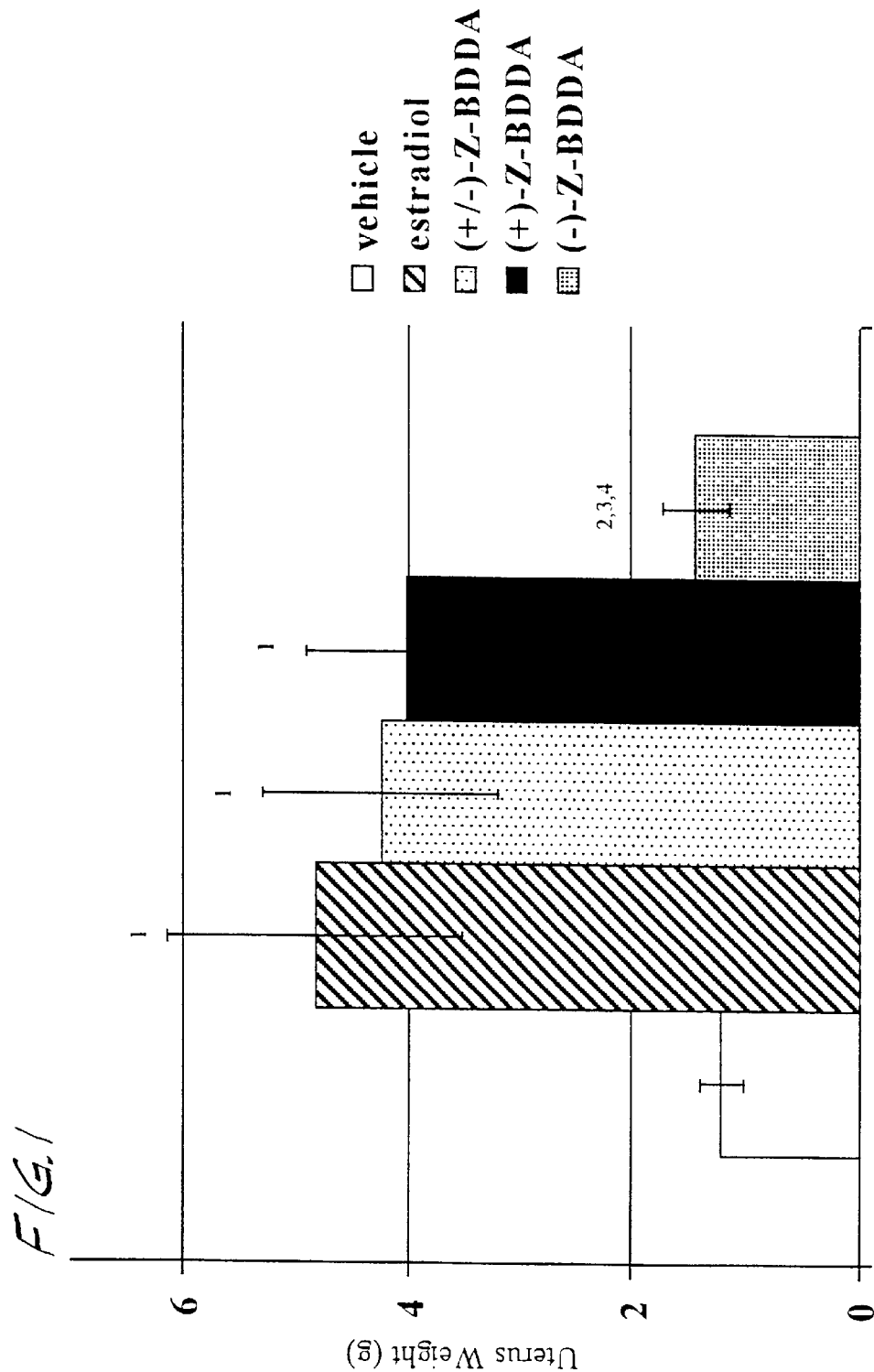

Akiyama, T. et al., "Genistein, A Specific Inhibitor Of Tyrosine–Specific Protein Kinases", *Journal of Biological Chemistry*, vol. 262, No. 12, pp. 5592–5595, 1987.

Anner, G. et al., "Die Totalsynthses Von Racemischen Doisynolsäuren. Über Oestrogene Carbonsäuren XXI", *Helv. Chim. Acta 30*, pp. 1422–1432, 1947.

Anner G. et al., "Hydrierungs– Und Umlagerungs–Reaktionen In Der Diosynolsäure–Reihe. Oestrogene Carbonsäuren XII", *Helv. Chim. Acta 29*, pp. 1889–1895, 1946.

Banz, W.J. et al., "Comparative Effects Of the Selective Estrogen Receptor Modulators(–)–, (+) and (±)–Z–Bisdehydrodoisynolic Acids On Metabolic And Reproductive Parameters In Male And Female Rats", *Hormone and Metabolic Research 30*, pp. 730–736, 1998.

Courrier, R. et al., "Biologie—L'acide Allenolique Et Ses Dérivés", *Acad. Sc. 224*, pp. 1401–1404, 1947.

Courier, R. et al., "Sur Un Nouvel Oestrogène Artificiel De Grande Activité", *Compt. Vend. Soc. De Biol. 141*, pp. 159–161, 1948.

Dodge, J. A. et al., "Environmental Estrogens: Effects On Cholesterol Lowering And Bone In The Ovariectomized Rat", *J. Steroid Biochem. Molec. Biol.*, vol. 59, No. 2, pp. 155–161, 1996.

Fieser, L.F., et al., *Natural Products Related To Phenanthrene*, 3rd Ed. Reinhold Publishing Corp., New York, NY, pp. 347–353, 1949.

Gay, R. et al., "N° 178.—Structure Moléculaire Et Activité Oestrogène (I). XV.—Préparation D'acides Dialcoyl–2,2 (Méthoxy–6 Naphtyl–2)–3 Pentanoïques Et D'acides Dailcoyl–2,2 (Méthoxy–6 Naphtyl–2)–3 Hexanoïques (Dérivés De L'acide Allénolique)"*Bull Soc. Chim France*, pp. 955–962, 1995.

Gudziak, M.R. et al., "Hormal Therapy for Stage D Cancer Of The Prostrate", *West J. Med.*, vol. 160, No. 4, pp. 351–359, 1994.

Hart, J.E., "Encocrine Pathology Of Estrogens: Species Differences", *Pharmac Ther*, vol. 47, pp. 203–218, 1990.

Heer, J. et al., "Totalsynthese der Racemischen Bisdehydro–doisynolsäuren. Über Oestrogene Carbonsäuren IV", *Helv. Chim. Acta 28*, pp. 1342–1354, 1945.

Herbai, G., "Separation Of Growth Inhibiting Potency From Oestrogenicity In Different Weak Oestrogenic Drugs Of Various Chemical Structures", *Acta Endocrinologica 68*, pp. 249–263, 1971.

Heywood, R. et al., "The Experimental Toxicology Of Estrogens", *Pharmac Ther.*, vol. 8, pp. 125–142, 1980.

Jacques, J. et al., N° 149—Structure Moléculaire Et Activité Oestrogène. (VI). Préparation De Quelques Dérivés De L'acide Amphihydroxynaphtyl β–Propionique (Acide Allénolique), *Bull. Soc. Chim. France*, pp. 711–716, 1948.

Jacques, J. et al., "N° 59—Structure Moléculaire Et Activité Oestrogène (VII). Dédoublement Optique De L'acide x.x–diméthyl β–éthyl Allénolique", *Bull. Soc. Chim. France*, pp. 301–303, 1949.

Knight, D. C. et al., "A Review Of The Clinical Effects Of Phytoestrogens", *Obstet Gynecol*, vol. 87, No. 5, Pt. 2, pp. 897–904, May 1996.

Kuiper G.G. et al., "Comparison Of The Ligand Binding Specificity And Transcript Tissue Distribution Of Estrogen Receptors αand β", *Endocrinology* vol. 138, No. 3, pp. 863–869, 1997.

Meyers, C.Y. et al., "Facile And Selective Chlorination–Cleavage Of Some Cyclanones And Cyclanols With The $CCl_4$–KOH–t–BuOH Reagent. In Situ Conversion Of Estrones and Estradiols Into Dichlorodiosynolic Acids", *J. Org. Chem*, vol. 43, pp. 1985–1990, 1978.

Meyers, C.Y. et al., "Doisynolic–Type Acids–Uterotropically Potent Estrogens Which Compete Poorly With Estradiol For Cytosolic Estradiol Receptors", *J. Steroid Biochem.*, vol. 31, No. 4A, pp. 393–404, 1988.

Meyers, C.Y. et al., "Transcriptional Regulation Of Estrogen–Responsive Genes By Non–Steroidal Estrogens: Doisynolic And Allenolic Acids", *J. Steroid Biochem. Molec. Biol.*, vol. 62, No. 5/6, pp. 477–489, 1997.

Miescher, K., "On Diosynolic Acids, A New Class Of Estrogens", *Chem. Rev.*, vol. 43, pp. 367–384, 1948.

Pace, P. et al., "Human Estrogen Receptor β Binds DNA In A Manner Similar To And Dimerizes With Estrogen Receptor α", *J. Biol. Chem.*, vol. 272, No. 41, pp. 25832–25838, 1997.

Rometsch, R. et al., "Die Spaltung Des Racemates Der N–Bisdehydro–Doisynolsäure. Über Östrogene Carsonsäuren X", *Helv. Chim. Acta 29*, pp. 1231–1235, 1946.

Sato, M. et al., "Raloxifene, Tamoxifen, Nafoxidine, Or Estrogen Effects On Reproductive and Nonreproductive Tissues In Ovariectomized Rats", *FASEB J*, vol. 10, pp. 905–912, 1996.

Schneeberg, N.G. et al., "Metallenestril, A New Synthetic Estrogen", *J. Am. Med. Assoc.*, vol. 161, No. 11, pp. 1062–1067, 1956.

Segaloff, A., "The Metabolism Of Estrogens With Particular Emphasis On Clinical Aspects Of Physiology And Function of Ovarian Hormones", *Recent Progress In Hormone Research IV*, pp. 85–111, 1949.

Sturnick, M.I. et al., "Clinical Assay Of A New Synthetic Estrogen: Vallestril", *New England J. Med.*, vol. 247, No. 22, pp. 829–834, 1952.

Terenius, L., "Inhibition of 17β–Oestradiol Uptake In Mouse Uterus By Doisynolic and Allenoic Acid Derivatives: An in Vitro Differentiation Between True Oestrogens And Pro–Oestrogens", Acta Pharmacol. et Toxicol., vol. 25, pp. 313–322, 1967.

Terenius, L., "Differential Inhibition in Vitro of 17β–Estradiol Binding In the Mouse Uterus And Vagina by Optical Antipodes Of Estrogens", *Molec. Pharmac*, vol. 4, pp. 301–310, 1968.

Tschopp, E., "Wirksamkeit, Organkonzentration Und Ausscheidung Der 7–Methyl–Bisdehydro–Doisynolsäure", *Helv. Physiol. Acta 4*, pp. 401–410, 1946.

Tschopp, E., "Die Oestrogene Wirkung Der Bisdehydro–Doisynolsäure Und Ihrer Derivate", *Helv. Physiol. Acta 4*, pp. 271–284, 1946.

Wieland, P. et al., "Abkömmlinge Alkylierter β–Naphtyl–Valeriansäuren. Über Oestrogene Carbonsäuren XXVI", *Helv. Chim. Acta 31*, pp. 1844–1854, 1948.

Soto, A.M., et al., "How Many Rings Can Be Cleaved From A Steroidal Estrogen While Preserving Its Estrogenic Activity?", *The Endorcine Society 1988 Abstract Form*.

Banz, W.J. et al., "Activities Of Non–classical Estrogens: Effects Of (–), (+), And (±) Z–Bisdehydrodoisynolic Acids In Vitro And On Body Weight In Male and Female Rats", *The Endocrine Society*, Jun. 1988, Abstract.

Horeau, A., et al., Académie Des Sciences, *Comptes Rendus*, vol. 224, pp. 862–864, 1947.

Winters et al., *Biol. Reprod.*, vol. 50 (Suppl. 1), 113, 1994.

Baker, V.L. et al., "Clinical Uses Of Antiestrogens", *Obstet Gynecol Surv*, vol. 51, pp. 45–59, 1996.

Behl, C. et al., "Neuroprotection Against Oxidative Stress By Estrogens: Structure–Activity Relationship", Mol. Pharmacol, vol. 51, pp. 535–541, 1997.

Bowen et al., *Programmed Cell Death In Tumors And Tissues,* Chapman & Hall, New York, NY, 1990.

Cooper, R.L. et al., "Endocrine Disruptors And Reproductive Development: A Weight–of–Evidence Overview", *J. Endocrinol*, vol. 152, pp. 159–166, 1997.

Crawley, G.C., "Hormones–nonsteroidal Estrogens", In Kirk–Othmer *Encyclo Chem. Technol,* vol. 12, pp. 670–671, 3rd. Ed., Grayson, Martin, Eckroth, David, Eds; Wiley: New York, 1980.

DanZo B.J., "Environmental Xenobiotics May Disrupt Normal Endocrine Function By Interfering With The Binding Of Physiological Ligands To Steroid Receptors And Binding Proteins", *Environ Health Perspect,* vol. 105, pp. 294–301, 1997.

deKlerk, D.P. et al., "Medical Therapy For Benign Prostatic Hyperplasia", *The Prostate,* pp. 119–128, JM Fitzpatrick and RJ Kranc, eds., Churchill Livingstone, New York, NY 1989.

Evans, S.F. et al., "Low And Conventional Dose Transdermal Oestradiol Are Equally Effective At Preventing Bone Loss In Spine And Femur At All Post–Menopausal Ages", *Clin. Endocrinol,* vol. 44, pp. 79–84, 1996.

Filley C.M., "Alzheimer's Disease In Women", *Am. J. Obstet. Gynecol.,* vol. 176, pp. 1–7, 1997.

Glashan, R.W. et al., "Cardiovascular Complications In The Treatment Of Prostatic Carcinoma", *Br. J. Urol,* vol. 53, pp. 624–627, 1981.

Hoover, J.E., *Remington's Pharmaceutical Sciences,* Mack Publishing Co., Easton, PA, 1975.

Jacobi, G.H., "Hormonal Treatment Of Metastatic Carcinoma", *The Prostate,* pp. 119–128, J.M. Fitzpatrick and R.J. Krane, eds., Churchill Livingstone, New York, NY, 1989.

Ke IIZ et al., "Comparative Effects Of Droloxifene, Tamoxifen, And Estrogen On Bone, Serum Cholesterol, And Uterine Histology In The Ovariectomized Rat Model", *Bone,* vol. 20, pp. 31–39, 1997.

Liberman, H.A. and Lachman, L., ed., *Pharmaceutical Dosage Forms,* Marcel Decker, New York, NY, 1980.

Nagel, S.C. et al., "Relative Binding Affinity–Serum Modified Access Assay Predicts The Relative In Vivo Bioactivity Of The Xenoestrogens Bisphenol A And Octylphenol", *Environ Health Perspect,* vol. 105 pp. 70–76, 1997.

Persson I., "Cancer Risk In Women Receiving Estrogen––Progestin Replacement Therapy", *Maturitas,* vol. 23, pp. S37–45, 1996.

Peterson, G. et al., "Genistein Inhibits both Estrogen and Growth Factor–Stimulated Proliferation Of Human Brest Cancer Cells", *Cell Growth & Differentiation,* vol. 7, pp. 1345–1351, 1996.

Reubimolf B.E. et al., "Effects Of Hormone Replacement Therpay On Weight, Body Composition, Fat Distribution, And Food Intake In Early Postmenopausal Women: A Prospective Study", *Fertil Steril,* vol. 64, pp. 963–968, 1995.

Smith, C.L. et al, "Modulation Of The Ligand–Independent Activation Of The Human Estrogen Receptor By Horomone And Antihormone", *Proc Natl Acad Sci,* vol. 90, pp. 6120–6124, 1993.

Spink, D.C. et al., "Stimulation Of 17 Beta–Estradiol metabolism In MCF–7 Cells by Bromochlor– And Chloromethyl–Substittued dibenZo–p–dioxins", *Environmental Health,* vol. 41, pp. 451–456, 1994.

Suttner et al., *Biol. Reprod.,* vol. 59(Suppl.): (Accepted for publication), 1998.

Tilly et al., *Endocrinology,* vol. 129, pp. 1799–1801, 1991.

Trenkle, A.H., "The Mechanisms Of Action Of Estrogens In Feeds On Mammalian And Avian Growth", *Proceedings Of A Symposium: The Use Of Drugs In Animal Feed,* National Academy of Science, Washington, D.C., pp. 150–164, 1968.

Wehling, M., "Specific, Nongenomic Actions Of Steroid Hormones", *Annu. Rev. Physiol,* vol. 59, pp. 365–393, 1997.

Wilson, P.W., "The Impact Of Estrogen On Cardiovascular Disease", Perspective Studies: The Framingham Study, *Postgrd Med 51–53,* pp. 89–90, 1989.

Wiseman H. et al., "Oestrogens As Antioxidant Cardioprotectants", *Biochemical Society Transactions,* vol. 25, pp. 54–59, 1977.

Hsi, et al., "Tumor Chemotherapy, XXXVI, Synethsis of Some 1–ethyl–2methyl–1,2,3, 4–tetrahydrophenanthrene–2–carboxylic acids and 2–naphthalenepropionic acids," Chemical Abstracts Service, 36(4), 1978.

Bercovici, J.P., "[Hormonal Treatment of the Menopause]. Le Traitement Hormonal De La Menopause," Contraception Fertilite Sexualite, 13/1 Suppl., 1985, pp. 277–281.

Vokaer, R., "[Estrogen Therapy (introduction)]. Introduction A La Therapeutique Par Les Oestrogenes," Annales D'Endocrinologie, 38/6, 1977, pp. 431–434.

"Management of the Menopause," Drug and Therapeutics Bulletin, 16/4, 1978, pp. 13–16.

Gordan, G.S. et al., "Antifracture Efficacy of Long Term Estrogens for Osteoporosis," Transactions of the Association of American Physicians, No. 86, 1973, pp. 326–332.

Bayard, F., "[Estrogens and Cancer]. Cestrogenes et Cancers," Revue Du Praticien, 29/21, 1979, pp. 1745–1752.

PCT International Search Report, Apr. 12, 2000, 14 pages.

* cited by examiner

Vehicle

Estradiol (−)-BDDA (+)-BDDA (−)-HAA (+)-HAA

Vehicle

Estradiol (−)-BDDA (+)-BDDA (−)-HAA (+)-HAA

METHOD FOR TREATING OR PREVENTING PROSTATIC CONDITIONS

This application claims benefit of provisional application 60/090,344, filed Jun. 23, 1998, and foreign priority of PCT/US99/13940, filed Jun. 22, 1999.

I. FIELD OF THE INVENTION

The present invention relates to the field of pharmaceutical therapeutics. More specifically, the present invention relates to the use of estrogenic carboxylic acids in improved therapies for the treatment of a variety of symptoms and disease conditions in mammals. The present invention also relates to the field of chemical synthesis, more specifically, the synthesis of estrogenic carboxylic acids.

II. BACKGROUND OF THE INVENTION

A. Estrogens

Estrogens, such as (+)-17β-estradiol (E2), have physiological effects on males as well as females. In addition to their activity in reproductive tissue, they promote rapid weight gain in specific species, and have been marketed to fatten livestock quickly. Trenkle, A H: "The Mechanisms of Action of Estrogens in Feeds on Mammalian and Avian Growth." *Proceedings of a Symposium: The Use of Drugs in Animal Feed.* National Academy of Science, Washington D.C. 150–164 (1968); Meyers, U.S. Pat. No. 5,420,161. Estrogens have long been prescribed for their beneficial effects by reducing susceptibility to osteoporosis and ameliorating menopausal and postmenopausal symptoms. Evans S F, Davie M W: "Low and Conventional Dose Transdermal Oestradiol Are Equally Effective at Preventing Bone Loss In Spine and Femur at All Post-Menopausal Ages." *Clin Endocrinol.* 44:79–84 (1996); Agarwal S K, Judd H L: "Menopause." *Curr Ther Endocrinol Metab.* 6:624–631 (1997). Long-term clinical studies suggest that estrogens may be beneficial in promoting cardiovascular health. Wilson P W: "The Impact of Estrogen on Cardiovascular Disease." Perspective Studies: The Framingham Study. *Postgrad Med* 51–53:89–90 (1989). More recently, estrogens have shown promise as an adjunct in treatment of Alzheimer's disease. Filley C M: "Alzheimer's Disease in Women." *Am J Obstet Gynecol* 176:1–7 (1997). Unfortunately, some estrogenic compounds administered in therapeutic doses are suspected carcinogens in target tissues including breast and uterus. Persson I: "Cancer Risk in Women Receiving Estrogen-Progestin Replacement Therapy." *Maturitas* 23:S37–45 (1996).

Non-steroidal estrogens and antiestrogens, including pharmaceuticals, environmental compounds, and phytochemicals, are currently receiving significant attention. This is understandable from the myriad potential applications increasingly being reported for estrogenic compounds, e.g., treating menopause- and post-menopause-related problems, as anti-carcinogens, alleviating osteoporosis, for contraceptive use, in estrogen-replacement therapy, treating prostatic disease, improving serum lipid profiles, etc. The multiplicity of estrogenic effects now being discovered has led many investigators to target specific populations for treatment with estrogen agonists and antagonists. Synthetic nonsteroidal compounds such as triphenylethylene derivatives (e.g., tamoxifen), dihydronapthalene derivatives (e.g., nafoxidine), and benzothiophene derivatives (e.g., raloxifene) exhibit estrogenic and anti-estrogenic activity in various tissues, these respective compounds showing specific advantages in the management of bone, uterine, serum cholesterol, and adipose tissue. See, generally, Trenkle, A H: "The Mechanisms of Action of Estrogens in Feeds on Mammalian and Avian Growth." *Proceedings of a Symposium: The Use of Drugs in Animal Feed.* National Academy of Science, Washington D.C. 150–164 (1968); Evans S F, Davie M W: "Low and Conventional Dose Transdermal Oestradiol Are Equally Effective at Preventing Bone Loss In Spine and Femur at All Post-Menopausal Ages." *Clin Endocrinol.* 44:79–84 (1996); Agarwal S K, Judd H L: "Menopause." *Curr Ther Endocrinol Metab.* 6:624–631 (1997); Wilson P W: "The Impact of Estrogen on Cardiovascular Disease." Perspective Studies: The Framingham Study. *Postgrad Med* 51–53:89–90 (1989); Filley C M: "Alzheimer's Disease in Women." *Am J Obstet Gynecol* 176:1–7 (1997); Persson I: "Cancer Risk in Women Receiving Estrogen-Progestin Replacement Therapy." *Maturitas* 23:S37–45 (1996); Heer J, Billeter J R, Miescher K: "Totalsynthese der racemischen bisdehydro-doisynolsäure. Über oestrogene carbosäuren IV." *Helv. Chim. Acta* 28:1342–1354 (1945); Ke H Z, Chen H A, Simmons H A, Qi H, Crawford D T, Pirie C M, Chidsey-Frink K L, Ma Y F, Jee W S S, Thompson D D: "Comparative Effects of Droloxifene, Tamoxifen, and Estrogen on Bone, Serum Cholesterol, and Uterine Histology in the Ovariectomized Rat Model." *Bone* 20:31–39 (1997); Sato M, Rippy M K, Bryant H U: "Raloxifene, Tamoxifen, Nafoxidine, or Estrogen Effects on Reproductive and Nonreproductive Tissues in Ovariectomized Rats." *FASEB J* 10:905–912 (1996); Dodge J A, Glasebrook A L, Magee D A, Phillips D L, Sato M, Short L L, Bryant H U: "Environmental Estrogens: Effects on Cholesterol Lowering and Bone in the Ovariectomized Rat." *J Steroid Biochem Molec Biol* 59:155–161(1996); Hart J E: "Endocrine Pathology of Estrogens: Species Differences." *Pharmac Ther* 47:203–218 (1990); Heywood R, Wadsworth P F: "The Experimental Toxicology of Estrogens." *Pharmac Ther* 8:125–142 (1980); Baker V L, Draper M, Paul S, Allerheiligen S, Glant M, Shifren J, Jaffe R B: "Reproductive Endocrine and Endometrial Effects of Raloxifene Hydrochloride, A Selective Estrogen Receptor Modulator, in Women with Regular Menstrual Cycles." *J Clin Endocrin Metab* 83:6–13 (1998); Danzo B J: "Environmental Xenobiotics May Disrupt Normal Endocrine Function by Interfering with the Binding of Physiological Ligands to Steroid Receptors and Binding Proteins." *Environ Health Perspect* 105:294–301 (1997); Baker V L, Jaffe R B: "Clinical Uses of Antiestrogens." *Obstet Gynecol Surv* 51:45–59 (1996); Knight D C, Eden J A: "A Review of the Clinical Effects of Phytoestrogens." *Obstet Gynecol* 87:897–904 (1996); Cooper R L, Kaviock R J: "Endocrine Disruptors and Reproductive Development: A Weight-of-Evidence Overview." *J Endocrinol* 152:159–166 (1997); Reubinoff B E, Wurtman J, Rojansky N, Adler D, Stein P, Schenker J G, Brzezinski A: "Effects of Hormone Replacement Therapy on Weight, Body Composition, Fat Distribution, and Food Intake in Early Postmenopausal Women: A Prospective Study." *Fertil Steril* 64:963–968 (1995).

B. Doisynolic Acids and Related Estrogenic Compounds

Doisynolic acids, named after their discoverer, Edward Doisy, are estrogenic compounds originally obtained from alkali fusion of estrone and equilenin. "Doisynolic acid," from estrone, contains a phenolic moiety; and "bisdehydro-doisynolic acid" (BDDA), from equilenin, possesses a β-naphtholic moiety. Both types are seco-steroids, i.e., the steroidal D-ring is cleaved. See Miescher K: "On Doisynolic Acids, A New Class of Estrogens." *Chem Rev* 43:367–384 (1948); Fieser L F, Fieser M: *Natural Products Related to Phenanthrene*, 347–353 (3rd Ed., Reinhold Publishing Corp., New York, N.Y. 1949). Meyers and Kolb reported the conversions of E2 and estrone under very mild conditions into doisynolic acids, which, in turn, exhibited estrogenic and antiestrogenic activity depending on dosage. Meyers C Y, Kolb V M: "Facile and Selective Chlorination and Cleavage of Some Cyclanones and Cyclanols With the $CCl_4$-KOH-t-BuOH Reagent. In situ Conversions of Estrones and Estradiols into Dichlorodoisynolic Acids." *J Org Chem* 43:1985–1990 (1978). A number of related pseudo-secosteroid acids (most of them containing only two rings or a shifted C ring) also have been prepared. These compounds have been cited as exhibiting varying degrees of estrogenicity. Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988).

It has been reported that (±)-Z-doisynolic acid is more estrogenic than (+)-E-doisynolic acid (C-14, S configuration) derived from estrone or E2. Anner G, Miescher K: Hydrierungs—Und Umlagerungs-Reaktion in der Doisynolsäure—Reihe. Oestrogene Carbonsäuren XII. *Helv. Chim. Acta* 29 (1946) 1889–1895; and Die totalsyntheses von racemischen doisynolsäuren XXI. Über oestrogene carbonsäueren. ibid 30:1422–1432 (1947). Of the Z and E isomers of the doisynolic-type compounds, (±)-Z-bisdehydrodoisynolic acid [(±)-Z-BDDA] has been reported to be among the most estrogenic in vivo, rivaling or even surpassing estradiol for vaginal cornification and uterotropism in the in vivo assays that were used to determine the comparative estrogenicity. Miescher K: "On Doisynolic Acids, A New Class of Estrogens." *Chem Rev* 43:367–384 (1948); Fieser L F, Fieser M: *Natural Products Related to Phenanthrene*, 347–353 (3rd Ed., Reinhold Publishing Corp., New York, N.Y. 1949); Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988); Tschopp E: "Wirksamkeit, organconzentration und ausscheidung der 7-methyl-bisdehydro-doisynolsäure." *Helv Physiol Pharmacol Acta* 4:401–410 (1946); Tschopp E: "Die oestrogene wirkung der bisdehydrodoisynolsäure und ihre derivate." *Helv Physiol Pharmacol Acta* 4:271–284 (1946); Rometsch R, Miescher K: "Die spaltung des racemates der n-bisdehydro-doisynolsäure. Über ostrogene carbonsäuren X." *Helv Chim Acta* 29:1231–1235 (1946); and Terenius L: "Differential Inhibition In Vitro of 17β-Estradiol Binding in the Mouse Uterus and Vagina by Optical Antipodes of Estrogen." *Molec Pharmac* 4:301–310 (1968). Additional assays of (±)-Z-BDDA for estrogenicity, based-on the estrogen-dependent cell proliferation in MCF-7 human mammary cancer cell line in culture, have confirmed the high estrogenic potency of this compound. Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988); and Soto A M, Meyers C Y, Sonnenschein C: "How Many Rings Can be Cleaved from a Steroidal Estrogen While Preserving its Estrogenic Activity?"*The Endocrine Society, 70th Annual Meeting*, Abstract (1988). And despite this estrogenic potency, the (±)-Z-BDDA has been reported to elicit neither toxicity nor carcinogenicity, even at 1000-times the estrogenic dosage. Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988). It has been reported that the (−) enantiomer of Z-BDDA is the one responsible for the observed estrogenic potency. Anner G, Miescher K: Hydrierungs—Und Umlagerungs-Reaktion in der Doisynolsäure—Reihe. Oestrogene Carbonsäuren XII. *Helv. Chim. Acta* 29 (1946) 1889–1895; Die totalsyntheses von racemischen doisynolsäuren XXI. Über oestrogene carbonsäueren. ibid 30:1422–1432 (1947); Tschopp E: "Wirksamkeit, organconzentration und ausscheidung der 7-methyl-bisdehydro-doisynolsäure." *Helv Physiol Pharmacol Acta* 4:401–410 (1946); Tschopp E: "Die oestrogene wirkung der bisdehydrodoisynolsäure und ihre derivate." *Helv Physiol Pharmacol Acta* 4:271–284 (1946); Rometsch R, Miescher K: "Die spaltung des racemates der n-bisdehydro-doisynolsäure. Über ostrogene carbonsäuren X." *Helv Chim Acta* 29:1231–1235 (1946); and Terenius L: "Differential Inhibition In Vitro of 17β-Estradiol Binding in the Mouse Uterus and Vagina by Optical Antipodes of Estrogen." *Molec Pharmac* 4:301–310 (1968).

One of the distinctive properties of estrogenic doisynolic acids is their very low binding affinity to cytosolic estrogen receptors when considered in context with their very high in vivo activity. This anomaly was discovered by competitive binding inhibition studies with $^3$H-estradiol using estrogen receptors extracted from rabbit uteri. Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988). Unlabeled estradiol has been reported to inhibit this binding strongly, while the doisynoic acids have been reported to do so only about 1% as well, despite being more active as estrogens in experimental animals. More recent direct binding studies with ER α and ER β confirmed these results. Segaloff A.: "The Metabolism of Estrogens with Particular Emphasis on Clinical Aspects of Physiology and Function of Ovarian Hormones." *Recent Progress in Hormone Research* 1949; IV:85–111; and Meyers C Y, Lutfi H G, Adler S: "Transcriptional Regulation of Estrogen-Responsive Genes by Non-Steroidal Estrogens: Doisynolic and Allenolic acids."*J Steroid Biochem Molec Biol* 62:477–489 (1997).

Many recent studies have focused particularly on the in vivo activity of (±)-Z-bisdehydrodoisynolic acid, the most active and easily available doisynolic acid. Competitive binding-inhibition studies with uterine cytosolic estrogen receptors (ER) showed that the binding affinity of (±)-Z-BDDA was on the order of 0.01–0.03 of that of E2. Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988); Soto A M, Meyers C Y, Sonnenschein C: "How Many Rings Can be Cleaved from a Steroidal Estrogen While Preserving its Estrogenic Activity? "*The Endocrine Society, 70th Annual Meeting*, Abstract (1988). Recent direct in vitro ER binding studies with human ER alpha (ER α) and ER beta (ER β) confirmed these results, in accord with the binding affinities of (−)-Z-BDDA determined with mouse uterine ER preparations in competitive binding-inhibition studies. Terenius L: "Differential Inhibition In Vitro of 17β-Estradiol Binding in the Mouse Uterus and Vagina by Optical Antipodes of Estrogen." *Molec Pharmac*

4:301–310 (1968); Segaloff A.: "The Metabolism of Estrogens with Particular Emphasis on Clinical Aspects of Physiology and Function of Ovarian Hormones." *Recent Progress in Hormone Research IV*:85–111 (1949); and Meyers C Y, Lutfi H G, Adler S: "Transcriptional Regulation of Estrogen-Responsive Genes by Non-Steroidal Estrogens: Doisynolic and Allenolic acids." *J Steroid Biochem Molec Biol* 62:477–489 (1997). Unlike most other estrogenic compounds studied with these techniques, the BDDA compounds exhibit a low binding affinity accompanied by a disproportionately high biological activity. Without being bound by any particular theory, it is believed that the classic estrogen receptor, ER, may not be the exclusive receptor or pathway involved in mediating the actions of Z-BDDA and other estrogenic compounds; and/or that doisynolic acid compounds may act in vivo by some mechanism other than by binding to estrogen cytosolic receptors to which estradiol, estrone, etc., normally bind. See Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988).

Differences in the activity of E2 and (±)-Z-BDDA based on other indices of estrogenic activity have also been observed. Specifically, while the rate of weight gain of female mice receiving E2 (e.g., 5 g/animal/day) was increased over that of the control group, the rate of weight gain of female mice receiving varying doses of (±)-Z-BDDA (e.g, 5, 50, and 500 g/animal/day) was actually diminished. Meyers, U.S. Pat. 5,420,161.

While estradiol and its 3-methyl ether have been reported to be estrogenic in animals and humans, the 3-methyl ether of (±)-Z-BDDA has only been reported to be estrogenic in some animals (but inactive in humans), and exhibits very little effect on proliferating human MCF-7 cell growth. Soto A M, Meyers C Y, Sonnenschein C: "How Many Rings Can be Cleaved from a Steroidal Estrogen While Preserving its Estrogenic Activity? *The Endocrine Society*, 70th Annual Meeting, Abstract (1988). It has been hypothesized that the enzyme or receptor responsible for the conversion of the 3-methyl ether of estradiol to the estrogenic phenolic estradiol is present in animals (including humans), while that required for the similar conversion of the 3-methyl ether of (±)-Z-BDDA is present in some animals, but not humans.

Despite the above-discussed advances, there still exists a need in the art for compounds exhibiting estrogen-like activity, but lacking the undesirable side effects often observed in connection with the use of conventional estrogens, for use in methods for treating a wide variety of symptoms, conditions, and diseases responsive to estrogens commonly employed at present.

C. Synthesis of Estrogenic Carboxylic Acids

In 1947 and 1948, Courrier, Horeau and Jacques (Courrier, R.; Horeau, A.; Jacques, J. Sur un nouvel oestrogene artificiel de grande activité. *Compt. rend. Soc. de biol.* 1948, 141, 159–161; Horeau, A.; Jacques, J. Structure moleculaire et activité oestrogene: acides hydroxynaphtylpropioniques substitutes. *Acad. Sc.* 1947, 224, 862–864; Courrier, R.; Horeau, A.; Jacques, J. L'acide allenolique et ses dérives. *Acad. Sc.* 1947, 224,1401–1407; Courrier, R.; Horeau, A.; Jacques, J. Action de l'acide dimethyl-ethyl-allenolique chez la femelle de cobaze qui allaite. *Compt. rend. Soc. de biol.* 1947, 141, 747; Jacques, J.; Horeau, A. Structure moleculaire et activité oestrogene (VI). Preparation de quelques derivés de l'acide amphihydroxynaphtyl β-propionique (acide allenolique). *Bull. Soc. Chim. France*, 1948, 711–716) reported the syntheses and biological studies of a series of estrogenic compounds derived from 3-[2-(6-hydroxynaphthyl)]propionic acid 1, which was named allenolic acid in honor of Dr. E. Allen. Of these compounds, (−)-3-[2-(6-methoxynaphthyl)]-2,2-dimethyl-pentanoic acid 2 was found to exhibit the strongest estrogenic activity in animals, including rats, cats, chicks, and guinea pigs, while the (+) enantiomer 3 showed only one-fifth the estrogenicity of 2 (Terenius, L. Inhibition of 17β-estradiol uptake on mouse uterus by doisynolic acid and allenolic acid derivatives: an in vitro differentiation between true oestrogens and pro-oestrogens. *Acta Pharmacol. et Toxicol.*, 1967, 25, 313–322; Herbai, G. Separation of Growth Inhibition Potency from Oestrogenicity in Different Weak Oestrogenic Drugs of Various Chemical Structures, *Acta Endocrinologica*, 1971, 68, 249–263). Later, the (−) enantiomer, 2, was marketed by G. D. Searle & Company under the trade name Vallestril® for the treatment of post-menopausal symptoms (Crawley, G. C. Hormones-nonsteroidal estrogens. In Kirk-Othmer *Encyclo. Chem. Technol.* 3rd Ed; Grayson, Martin, Eckroth, David, Eds; Wiley: New York, 1980; vol. 12, 670–671).

Although 2 was highly estrogenic in animals, equivalent to 17β-estradiol (E2), it was not found to have the same effects in women as E2. In clinical trials, high dosages were required to elicit strong estrogenic responses from women (Stumick, M. I.; Gargill, S. L. Clinical assay of a new synthetic estrogen: Vallestril. *New England J. Med.*, 1952, 247, 830–834; Schneeberg, N. G.; Perczek, L.; Nodine, J. H.; Perloff, W. H. Methallenstril, a new synthetic estrogen. *J. Am. Med. Assoc*; 1956, 161, 1062–1067), and thus 2 was eventually removed from the market.

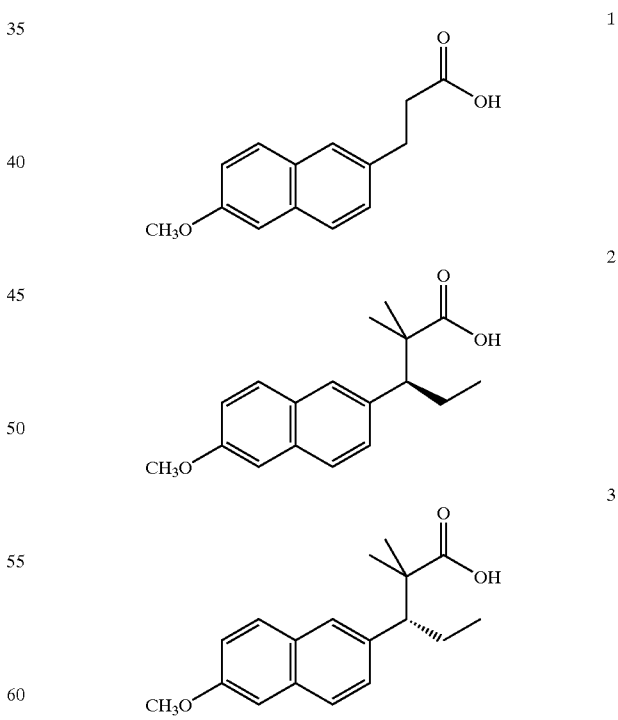

In 1967, Terenius (Terenius, L. Inhibition of 17β-estradiol uptake on mouse uterus by doisynolic acid and allenolic acid derivatives: an in vitro differentiation between true oestrogens and pro-oestrogens. *Acta Pharmacol. et Toxicol.*, 1967, 25, 313–322) proposed that 2 was a pro-estrogen, and that the true estrogen is its free phenolic form, i.e., compound 4, based on a study of the inhibition of 17β-estradiol uptake in mouse uterus by those compounds. In 1971, Herbai (Herbai, G. Separation of Growth Inhibition Potency from Oestrogenicity in Different Weak Oestrogenic Drugs of Various Chemical Structures, *Acta Endocrinologica*, 1971, 68, 249–263) reported that in mice, compound 4 exhibited a 100-fold stronger activity with regard to both inhibition of weight gain and sulfate incorporation than compound 2. However, the (+) enantiomer of 4, compound 5, caused significant depression of sulfate incorporation without the corresponding effects on weight gain. Some years later, Soto et al. (Soto, A. M.; Meyers, C. Y.; Sonnenschein, C. How Many Rings Can Be Cleaved from a Steroidal Estrogen while Preserving its Estrogenic Activity? The Endocrine Society, 70th Annual Meeting, Abstract (1988)) found that while 2 showed very little effect in human MCF-7 cell proliferation, its phenolic form, 4, was found to be highly effective, suggesting that the low estrogenicity of 2 in women is due to human inability to cleave the methyl group from the ethereal oxygen.

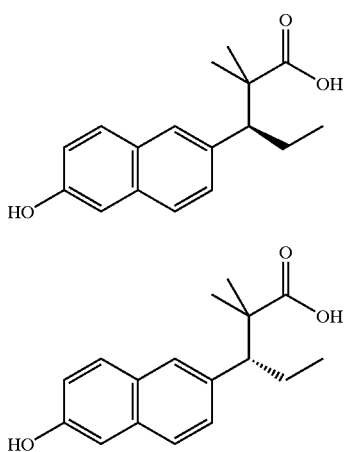

Currently, there is a great deal of research interest in selective estrogen receptor modulators (SERMs) (Baker, V. L.; Draper, M.; Paul, S.; Allerheiligen, S.; Glant, M.; Shifren, J.; Jaffe, R. B. Reproductive endocrine and endometrial effects of raloxifene hydrochloride, a selective estrogen receptor modulator, in women with regular menstrual cycles. *J. Clin. Endocrinol. Metab.*, 1998, 83, 6–13). SERMs have many potential medical applications, such as in treating postmenopausal symptoms, preventing osteoporosis, and hormonal therapy for prostate cancer, while eliminating the unwanted side effects. For example, raloxifene is marketed by Eli Lilly under the trade name Evista® to prevent osteoporosis in postmenpausal women while having little effect on other reproductive organs. Recent studies on the physiological effects of (+)- and (−)-cis-bisdehydrodoisynolic acids (cis-BDDA) in rats indicated that these compounds could be used in a number of therapeutic applications (Banz, W. J.; Winters, T. A.; Hou, Y.; Adler, S.; Meyers, C. Y. Comparative Effects of(−)-, (+)- and (±)-Z-Bisdehydrodoisynolic Acids and Estradiol on Body Weight, Food Intake and Metabolic Parameters in Male and Female Rats. *Hormone and Metabolic Research*, 1998, 30, 730–736). More importantly, (+)- and (−)-cis-BDDA have different physiological effects on vanous organs in intact rats. As estrogenic carboxylic acids, 4 and 5 have been shown to have similar in vitro and in vivo biological properties to cis-BDDA (Meyers, C. Y.; Lutfi, H. G.; Adler, S. Transcriptional regulation of estrogen-responsive genes by non-steroidal estrogens: Doisynolic and allenolic acids. *J. Steroid Biochem. Molec. Biol.*, 62, 477–489 (1997)).

3-[2-(6-methoxynaphthyl)]-2,2-dimethylpentanoic acid has an asymmetric center on the benzylic carbon. Thus, there exist two enantiomers, as indicated by structures 2 and 3, above. Previous syntheses all yielded a racemic mixture of 2 and 3. Thus, a resolution process was required to obtain the desired enantiomer, as in the case of Vallestril®. Jacques and Horeau reported that quinine could be used to resolve the two enantiomers by forming two. diastereomeric salts (Jacques, J.; Horeau, A. Structure moléculaire et activite oestrogène (VII). Dédoublement optique de l'acide α,α-diméthyl β-éthyl allénolique. *Bull. Soc. Chim. France*, 1949, 301–303).

Jacques and Horeau first reported the synthesis of (±)-3-[2-(6-methoxynaphthyl)]-2,2-dimethylpentanoic acid in 1947 and obtained a patent in 1949 (Scheme 1) (Jacques, J.; Horeau, A. Structure moleculaire et activité oestrogene (VI). Préparation de quelques dérivés de l'acide amphihydroxynaphtyl β-propionique (acide allenolique). *Bull. Soc. Chim. France*, 1948, 711–716; Jacques, J.; Horeau, A. Naphthalene derivatives having estrogenic activity. Fr. Pat. 941,289 (1949)).

Scheme 1

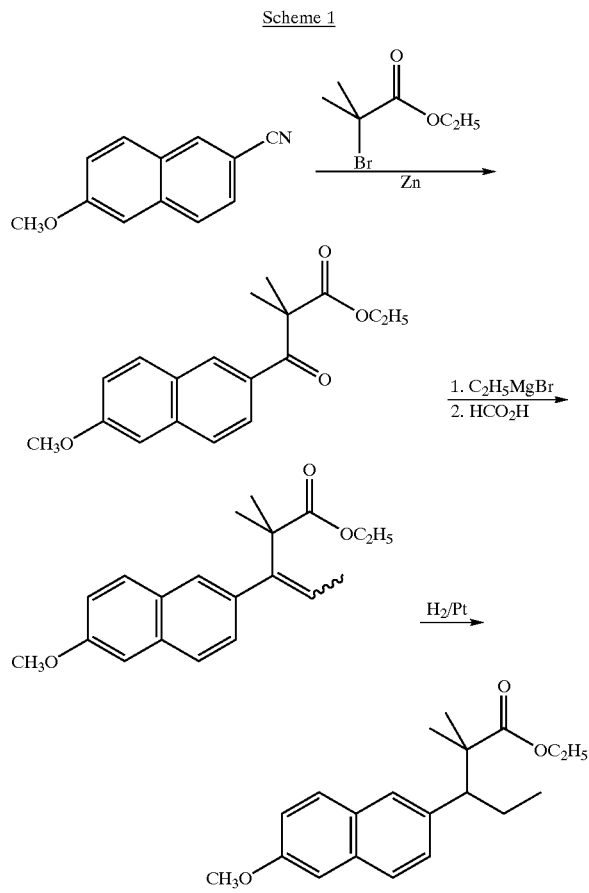

In 1948, Wieland and Miescher (Wieland, P.; Miescher, K. Estrogenic carboxylic acids. XXVI. Derivatives of alkylated β-naphthylvaleric acids. *Helv. Chim. Acta*, 1948, 31, 1844–1854) reported a different synthesis of a racemic mixture of 2 and 3, and Gay and Horeau (Gay, R.; Horeau, A. Molecular structure and estrogenic activity. XV. Preparation of 2,2-dialkyl-3-(6-methoxy-2-naphthyl)pentanoic acids and 2,2-dialkyl-3-(6-methoxy-2-naphthyl)hexanoic acids (derivatives of allenolic acid). *Bull. Soc. Chim. France*, 1955, 955–962) also synthesized a racemic mixture through a similar route (Scheme 2). These syntheses (Schemes 1 and 2) are multistep processes. After each step, separation of the intermediate product must be performed before it is used for the next reaction. Thus, additional chemicals, energy, and manpower are needed, which increases the cost of production and lowers the overall yield of the desired product.

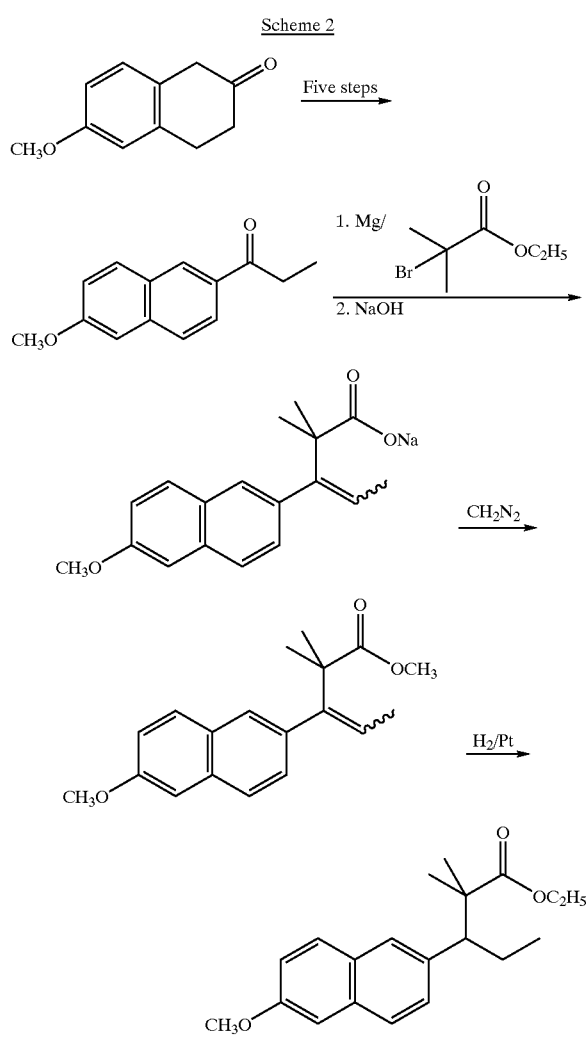

Ciba Ltd. patented the shortest reported synthesis of racemic mixture of 2 and 3 so far in literature (Scheme 3) (Ciba Ltd, Naphthalenepropionic Acid, Swiss Patent 261, 123 (1949); Ciba Ltd, Naphthalenepropionic Acids and Derivatives thereof, British Patent 652,003 (1951)). Although there is only one step in this process, the yield of the product was not high due to self-coupling reactions.

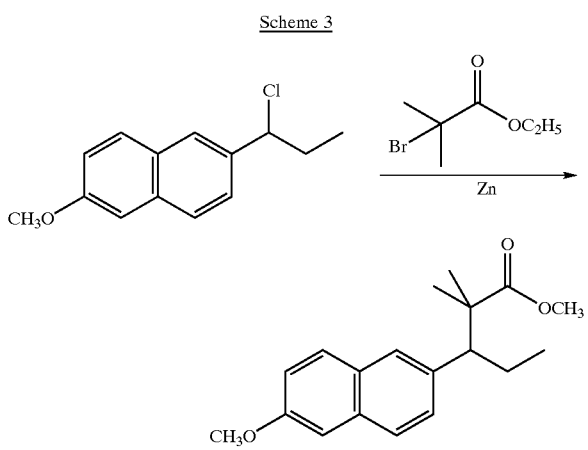

All of these syntheses lead to a racemic mixture containing equal amounts of 2 and 3. Due to the different biological properties of enantiomers 2 and 3, a resolution step must be performed to separate and isolate each enantiomer for pharmaceutical use, which also significantly increases the cost of production. In addition, the undesired enantiomer (50% of the racemic mixture) generated in the resolution process may be wasted if it is not used in other applications.

In the absence of a commercial source of 4 and 5, a one-pot, asymmetric synthesis of either 4 or 5 is needed in the art.

III. SUMMARY OF THE INVENTION

The present invention provides methods of using estrogenic carboxylic acids and other non-steroidal estrogen-like compounds to treat or prevent a variety of conditions and diseases now being treated with conventional estrogens such as estradiol, ethinyl estradiol, estrone, or Premarin. The methods disclosed herein are based in part on the emerging realization that the female hormones produced in males, and conversely male hormones produced in females, have far reaching effects in health and disease, affording new approaches to a variety of therapies. Further, the use of the estrogenic compounds disclosed herein in the methods described below should result in improved therapies lacking the undesirable side effects often seen in connection with the use of conventional estrogens.

Thus, in one aspect, the present invention provides a method for repressing weight gain or reducing weight in a male patient, comprising administering (+)-Z-bisdehydrodoisynolic acid in a dosage effective to repress weight gain or reduce weight to a male patient suffering from, or disposed to, weight gain.

In another aspect, the present invention provides a method for treating or preventing prostate cancer, comprising administering an estrogenic carboxylic acid in a dosage effective to treat or prevent prostate cancer to a patient suffering from, or disposed to, prostate cancer. The estrogenic carboxylic acid can also be used to maintain prostate cancer patients who have been previously treated with inhibitors of gondadotropin releasing hormone (GnRH) secretion or of testosterone. The predominant hormonal treatment now in use for prostate cancer consists of monthly injections of leuprolide, an antagonist of GnRH. Hot flashes resulting from this treatment are a common complaint. In addition, leuprolide, a polypeptide, may give rise to an immune response on continued use. In contrast, the estrogenic carboxylic acids of the present invention are almost certainly non-immunogenic. These compounds should reduce the size of the testes, thereby ameliorating the effects of prostate hyperplasia, limiting the spread of prostate cancer cells.

In another aspect, the present invention provides a method for treating or preventing peri- or post-menopausal symptoms, comprising administering an estrogenic carboxylic acid in a dosage effective to treat or prevent peri- or post-menopausal symptoms to a patient suffering from, or disposed to, said menopausal symptoms. The present estrogenic carboxylic acids can be used in place of conventional estrogens in hormone replacement therapy in menopause.

In another aspect, the present invention provides a method for treating an estrogen-responsive condition that no longer responds to treatment with conventional steroidal estrogens, comprising administering an estrogenic carboxylic acid in a dosage effective to repress, reduce, or otherwise ameliorate said condition to a patient suffering from said condition.

In yet another aspect, the present invention provides a method for treating or preventing an estrogen-responsive uterine cancer, comprising administering an estrogenic carboxylic acid in a dosage effective to treat or prevent said cancer to a patient suffering from, or disposed to, said cancer.

In yet another aspect, the present invention provides a method for treating or preventing breast cancer, comprising administering an estrogenic carboxylic acid in a dosage effective to treat or prevent said cancer to a patient suffering from, or disposed to, breast cancer.

These methods of treating uterine cancer and breast cancer are based on the estrogenic, antiestrogenic, and antioxidant properties of the present estrogenic carboxylic acids.

In another aspect, the present invention provides a method for treating or preventing ovarian follicle atresia, comprising administering an estrogenic carboxylic acid in a dosage effective to treat or prevent ovarian follicle atresia to a patient suffering from, or disposed to, atresia.

In a further aspect, the present invention provides a method for inducing ovulation to increase fertility, comprising administering an estrogenic carboxylic acid in a dosage effective to induce ovulation to a patient suffering from, or disposed to, ovulatory disorder. The estrogenic carboxylic acid can be administered during the mid-portion of the first part of the menstrual cycle, for example, for five days, starting at the fifth day of said menstrual cycle.

In yet a further aspect, the present invention provides a method for oral contraception, comprising administering an estrogenic carboxylic acid in a dosage effective to prevent ovulation to said patient throughout the menstrual cycle, starting at day one thereof and continuing throughout said menstrual cycle to about day 21. This method is especially useful for treatment of a patient not suitable for treatment with a steroidal estrogen, for example one who is a tobacco smoker, an obese patient, a patient suffering from breast disease, or a patient prone to producing emboli. In obese patients, this method provides the added benefit of promoting concomitant weight loss. In these methods, the estrogenic carboxylic acid can be administered in combination with a progestin.

In another aspect, the present invention provides a method for treating or preventing a disease or condition caused or prolonged by free radicals, comprising administering an estrogenic carboxylic acid in a dosage effective to treat or prevent said disease or condition to a patient suffering from, or disposed to, said disease or condition.

Another aspect of the present invention provides a method for treating or preventing cardiovascular disease, comprising administering an estrogenic carboxylic acid in a dosage effective to treat or prevent cardiovascular disease to a patient suffering from, or disposed to, cardiovascular disease.

In another aspect, the present invention provides a method for treating or preventing hyperlipidemia or hypercholesterolemia, comprising administering an estrogenic carboxylic acid in a dosage effective to treat or prevent hyperlipidemia or hypercholesterolemia to a patient suffering from, or disposed to, hyperlipidemia or hypercholesterolemia.

In another aspect, the present invention provides a method for treating or preventing hyperglycemia, comprising administering an estrogenic carboxylic acid in a dosage effective to treat or prevent hyperglycemia to a patient suffering from, or disposed to, hyperglycemia.

Yet another aspect of the present invention involves a method for improving body fat distribution, comprising administering an estrogenic carboxylic acid in a dosage effective to improve body fat distribution to a patient suffering from, or disposed to, abnormal body fat distribution.

A further aspect of the present invention relates to a method for treating or preventing Alzheimer's disease, comprising administering an estrogenic carboxylic acid in a dosage effective to treat or prevent Alzheimer's disease to a patient suffering from, or disposed to, Alzheimer's disease.

Yet a further aspect of the present invention relates to a method for treating or preventing osteoporosis, comprising administering an estrogenic carboxylic acid in a dosage effective to treat or prevent osteoporosis to a patient suffering from, or disposed to, osteoporosis.

In still another aspect, the present invention provides a method for treating or preventing pattern baldness, comprising administering an estrogenic carboxylic acid in a dosage effective to treat or prevent pattern baldness to a patient suffering from, or disposed to, pattern baldness. Such patients include both males and females. In balding men, hair growth should be stimulated by the reduction of testosterone levels produced by feedback inhibition of the pituitary occasioned by the rise in estrogen.

In another aspect, the present invention provides a method for treating or preventing a prostatic disease or condition, comprising administering an estrogenic carboxylic acid in a dosage effective to treat or prevent a prostatic disease or condition to a patient suffering from, or disposed to, such disease or condition. (+)-Z-BDDA, (−)-Z-BDDA, (−)-HAA, (+)-HAA, can be used in this method, with (+)-Z-BDDA being preferred. Examples of prostatic diseases and conditions amenable to such treatment include, but are not limited to, prostate cancer, benign prostate hypertrophy, and prostatitis. These and other prostatic diseases and conditions can be treated without negative side effects such as testis shrinkage, inhibition of spermatogenesis, gynecomastia, or other feminizing effects in males in accordance with this method.

In another aspect, the present invention provides a method for treating or preventing an androgen-responsive pathological condition in a male, comprising administering an estrogenic carboxylic acid in a dosage effective to treat or prevent said pathological condition to a male patient suffering from, or disposed to, said pathological condition.

In yet another aspect, the present invention provides a method of birth control, comprising administering an estrogenic carboxylic acid in a dosage effective to inhibit spermatogenesis in a male. Compounds useful in this method include, but are not limited to, (−)-Z-BDDA, (−)-HAA, and (+)-HAA.

In a still further aspect, the present invention provides a method for chemical castration in a male, comprising administering an estrogenic carboxylic acid in a dosage effective to shrink the testis or cause a loss of libido and/or impotence in a male. Compounds useful in this method include, but are not limited to, (−)-Z-BDDA, (−)-HAA, and (+)-HAA.

Treatment of the foregoing symptoms, conditions, and diseases with the compounds of the present invention should be accompanied by fewer side effects than are often observed in connection with the use of conventional estrogens.

In any of the foregoing methods, the estrogenic therapeutic compound most preferably is an estrogenic carboxylic acid, such as, for example, a doisynolic acid, an allenolic acid, a phenylcyclohexenecarboxylic acid, a hydroxyphenylcyclo-hexenecarboxylic acid, a phenylcyclohexanecarboxylic acid, a hydroxyphenylcyclohexanecarboxylic acid, a hydroxytetrahydro-anthracenecarboxylic acid, or a tetrahyroanthracene-carboxylic acid. More specifically, the estrogenic carboxylic acid can be, for example, (+)-doisynolic acid, (−)-Z-bisdehydrodoisynolic acid, (+)-Z-bisdehydrodoisynolic acid, (±)-Z-bisdehydrodoisynolic acid (Z-BDDA), (−)-allenolic acid, (+)-allenolic acid, 1-(p-hydroxyphenyl)-6-ethyl-5-methylcyclohexene-4-carboxylic acid, 1-(p-hydroxyphenyl)-2-ethyl-3-methylcyclohexene-4-carboxylic acid, 1-p-hydroxyphenyl)-2-ethyl-3,5,5-trimethylcyclohexene-4-carboxylic acid, 4-(p-hydroxyphenyl)-2,2,6,6-tetramethylcyclohexanecarboxylic acid, 1-ethyl-6-hydroxy-2-methyl-1,2,3,4-tetrahydroanthracene-2-carboxylic acid, 1-phenyl-2-ethyl-3-methylcyclohexene-4-carboxylic acid, and 1-phenyl-5,6-dimethylcyclohexene-4-carboxylic acid. Derivatives of such compounds (e.g., a pharmaceutically acceptable salt, ester, or anhydride) may also be used. In the methods disclosed herein, these estrogenic carboxylic acids can be used alone or in combination.

In yet another aspect, the present invention provides a direct one-pot synthesis to produce esters of 3-[2-(6-methoxynaphthyl)]-2,2-dimethylpentanoic acid from commercially available starting material. These esters can then be easily hydrolyzed under basic or acidic conditions to yield the corresponding acids 2 or 3, discussed above.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

IV. BRIEF DESCRIPTION OF THE DRAWINGS

The above and other objects, features, and advantages of the present invention will be better understood from the following detailed description taken in conjunction with the accompanying drawings, all of which are given by way of illustration only, and are not limitative of the present invention, in which:

FIG. 1 shows results of Experiment 2 of Example 2, i.e., the effects of (−)-, (+)-, and (±)-Z-bisdehydrodoisynolic acid (Z-BDDA) and (+)-17βb-estradiol on uterus weight in rats on treatment for 5–6 weeks [[1]significantly different from vehicle (p<0.05) and [2]significantly different from (−)-Z-BDDA (p<0.05), n=5/treatment, all values are the mean±SEM].

Figure 2:
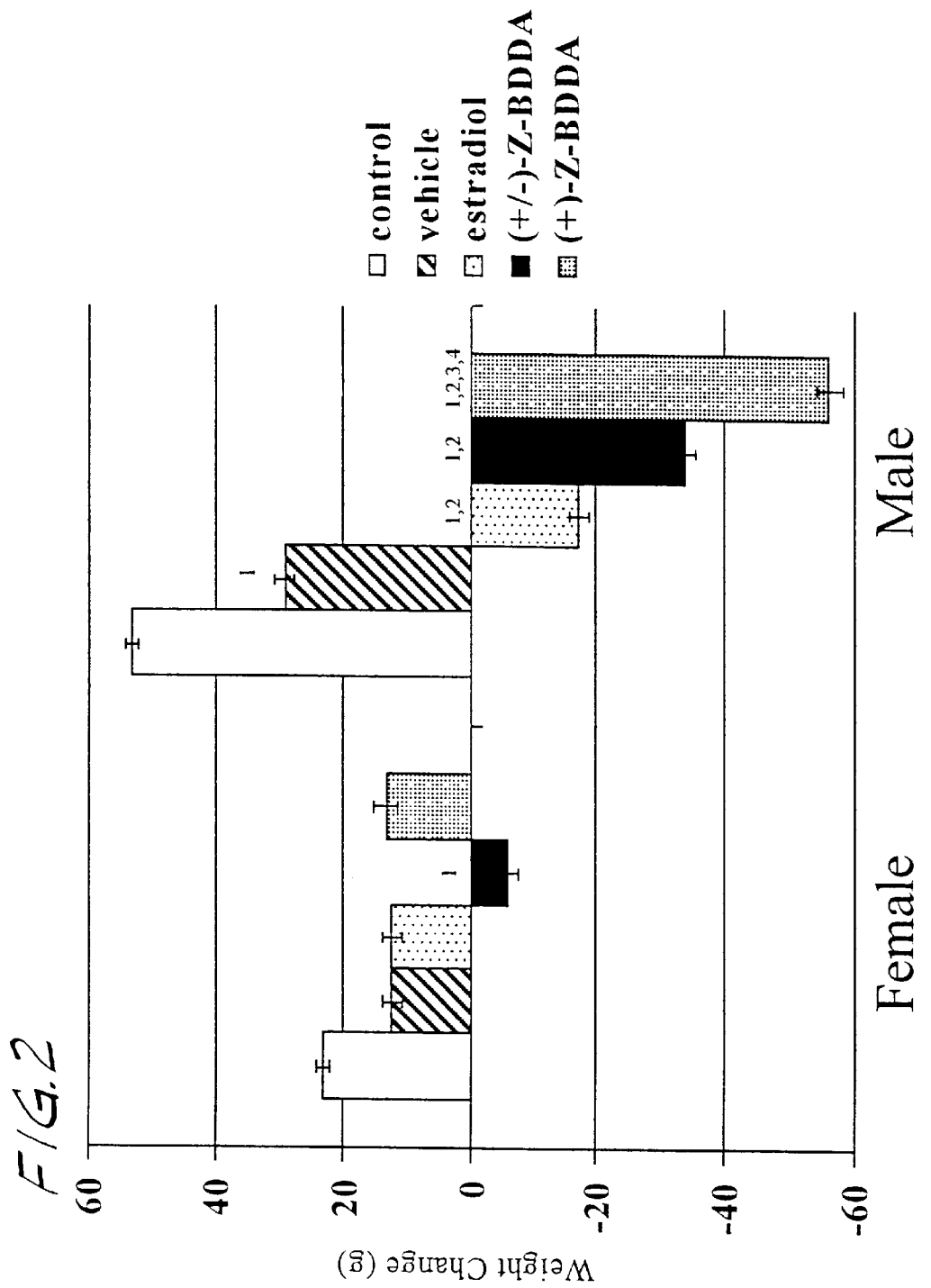

FIG. 2 shows results of Experiment 1 of Example 2, i.e., the effects of (+)- and (±)-Z-bisdehydrodoisynolic acid (Z-BDDA) and (+)-17β-estradiol on percent weight change in male and female rats on treatment for 4 weeks [[1]significantly different from control (p<0.05); [2]significantly different from vehicle (p<0.05); [3]significantly different from estradiol (p<0.05); and [4]Significantly different from (±)-Z-BDDA (p<0.05), n=5/treatment. All values are the mean±SEM].

Figure 3:
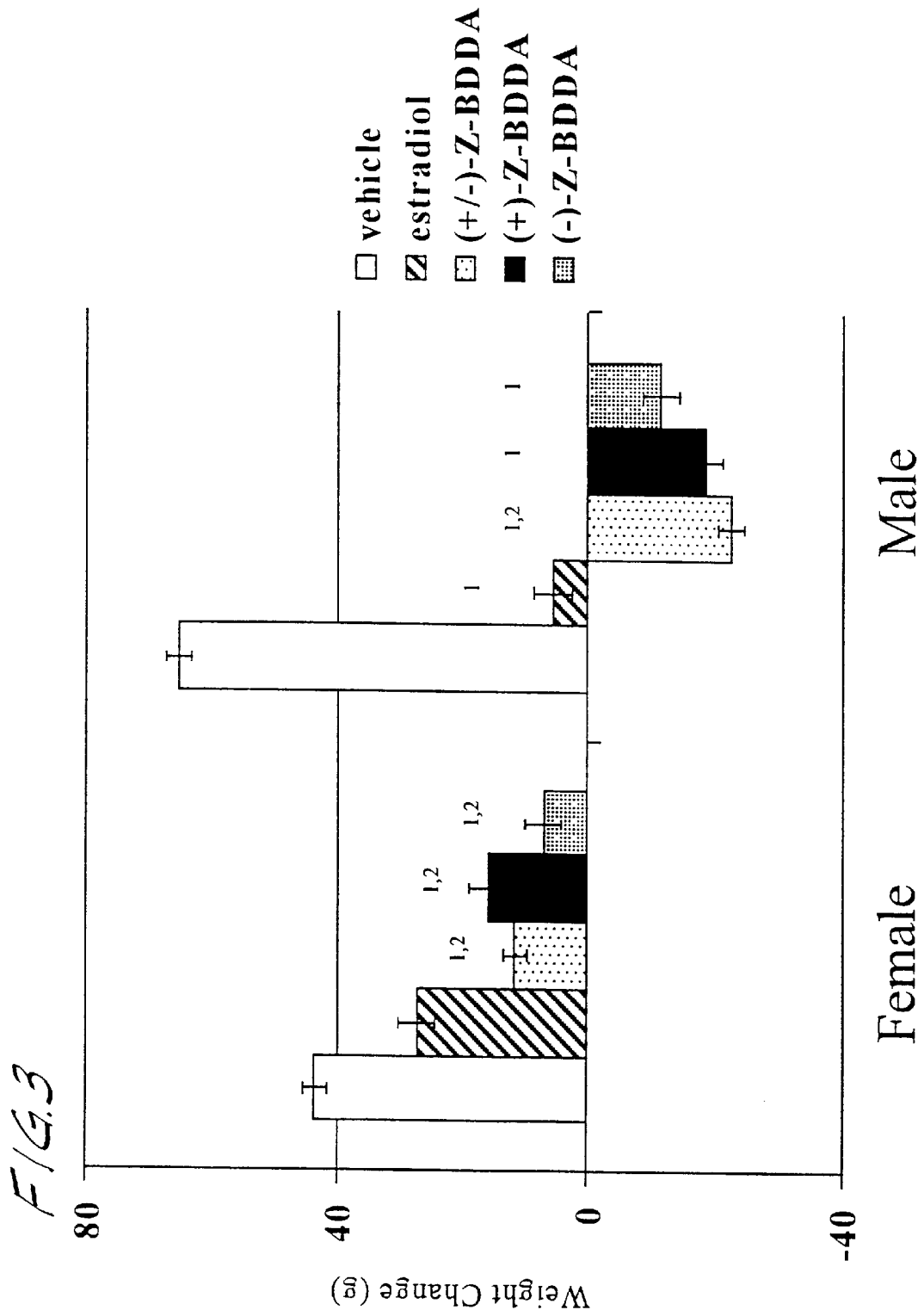
Figure 4A:
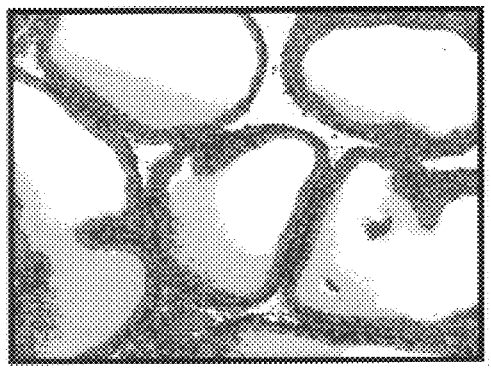
Figure 4B:
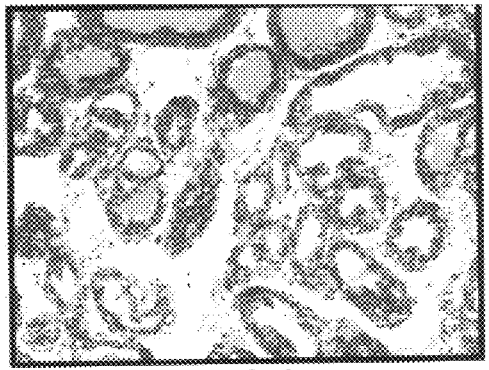
Figure 4C:
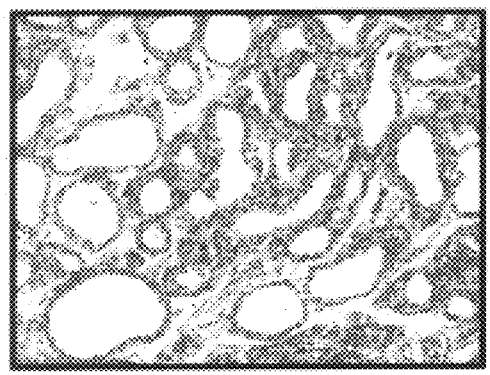
Figure 4D:
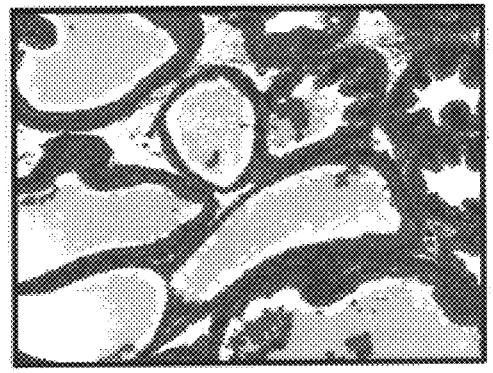
Figure 4E:
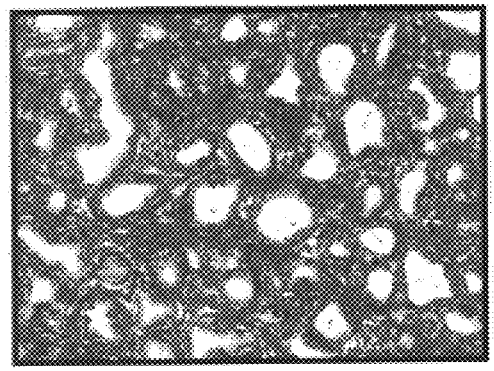
Figure 4F:
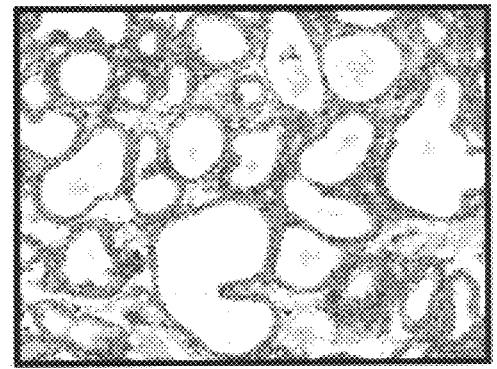
Figure 5A:
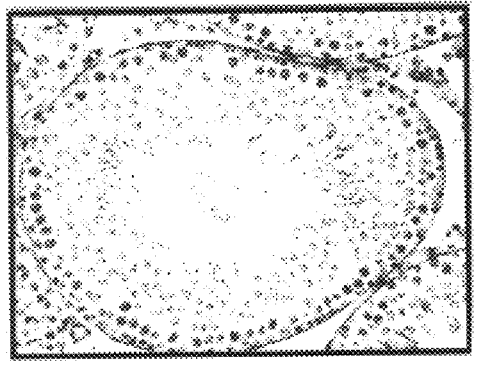
Figure 5B:
Figure 5C:
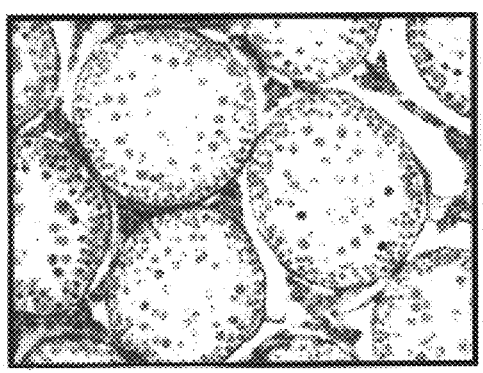
Figure 5D:
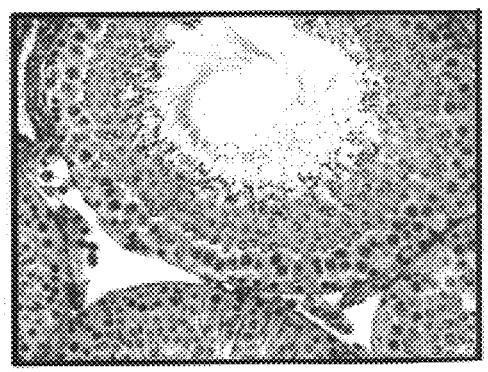
Figure 5E:
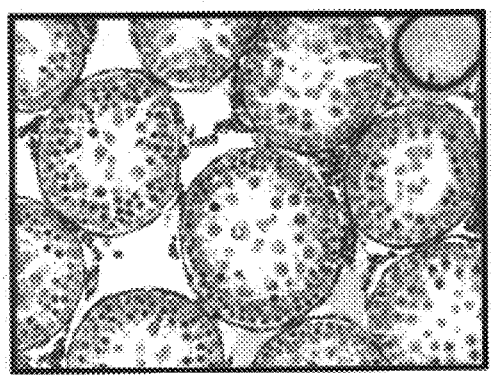
Figure 5F:
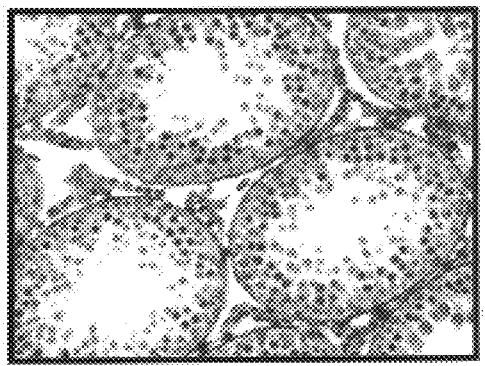

FIG. 3 shows results of Experiment 2 of Example 2, i.e., the effects of (−)-, (+)-, and (±)-Z-bisdehydrodoisynolic acid (Z-BDDA) and (+)-17β-estradiol on % weight change in male and female rats on treatment for 5–6 weeks [[1]significantly different from vehicle (p<0.05) and [2]significantly different from estradiol (p<0.05), n=5/treatment, all values are the mean±SEM].

FIGS. 4a–4f show the effects of (−)- and (+)-Z-bisdehydrodoisynolic acids (BDDA), (−)- and (+)-hydroxyallenolic acid (HAA), and (+)-17β-estradiol (E) on prostate histology in male rats on treatment for 6 weeks (Example 4). Photomicrographs represent hemotoxylin and eosin stains of paraffin sections photographed at 20X. Representative panels were treated as labeled at 0.1 μg/g body-weight.

FIGS. 5a–5f show the effects of (−)- and (+)-Z-bisdehydrodoisynolic acids (BDDA), (−)- and (+)-hydroxyallenolic acid (HAA), and (+)-17β-estradiol (E) on testis histology in male rats on treatment for 6 weeks (Example 4). Photomicrographs represent hemotoxylin and eosin stains of paraffin sections photographed at 20x. Representative panels were treated as labeled at 0.1 μg/g body-weight.

Figure 6:
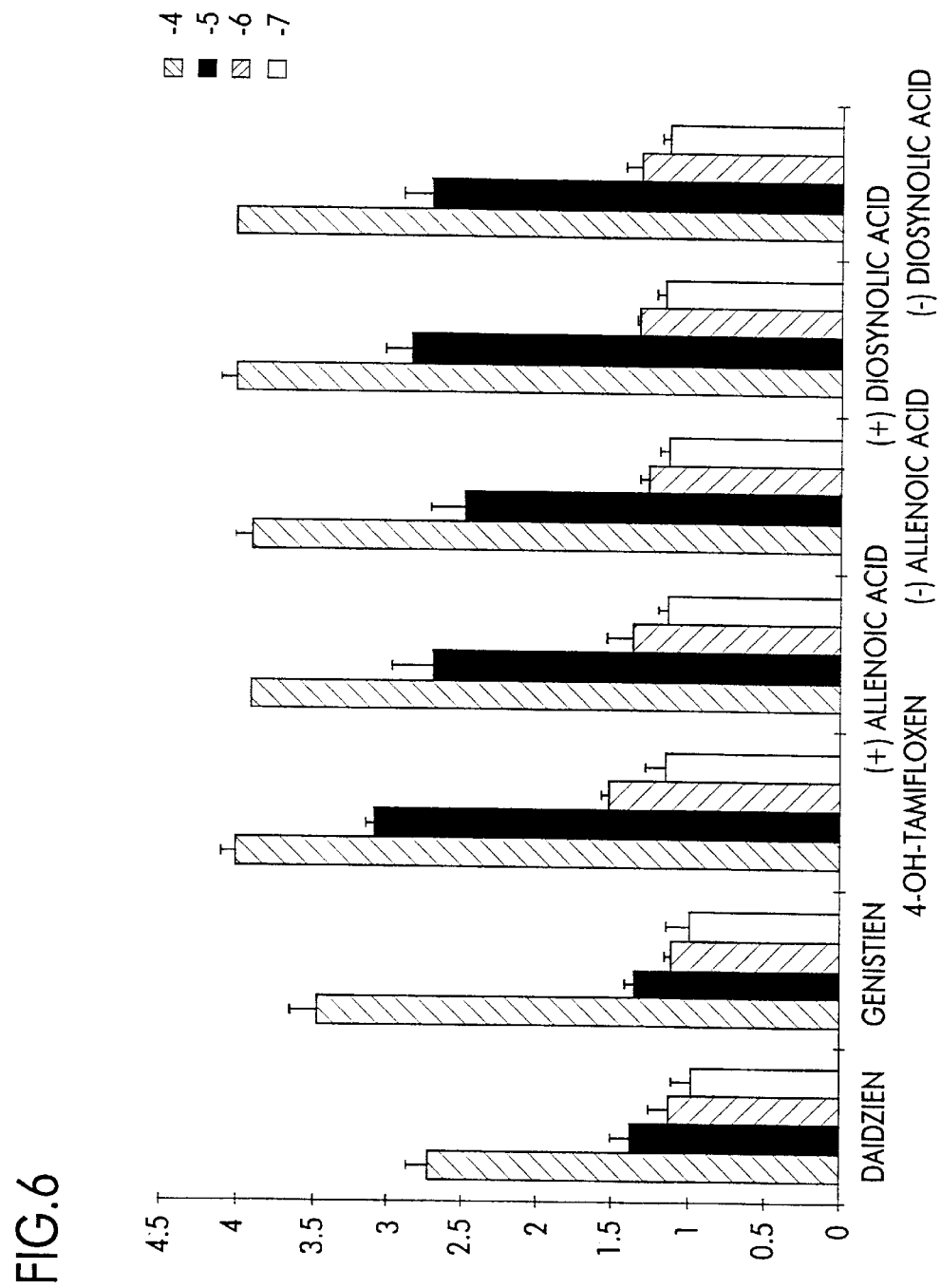

FIG. 6 shows the results of the lag time oxidation studies described in Example 5. Compounds shown on the x-axis, from left to right: daidzein, genistein, 4-hydroxy-tamoxifen, (+)-allenolic acid, (−)-allenolic acid, (+)-Z-bisdehydrodoisynolic acid, (−)-Z-bisdehydrodoisynolic acid. Each compound was tested at a concentration of $10^{-4}$, $10^{-5}$, $10^{-6}$, and $10^{-7}$ M. The results obtained at each of these concentrations is shown for each compound, from left to right as a vertical bar, respectively.

V. DETAILED DESCRIPTION OF THE INVENTION

Although the following detailed description is provided to aid those skilled in the art in practicing the present invention, it should not be construed to unduly limit the present invention. Modifications and variations in the embodiments discussed herein can be made by those of ordinary skill in the art without departing from the spirit or scope of the present inventive discovery.

The present methods utilize the unique properties of doisynolic acid and related estrogenic compounds (especially related estrogenic carboxylic acids) in animal (particularly human) therapy and research. Based on the properties of these compounds, together with present methods of treating prostate, breast, and uterine cancer, osteoporosis, atresia, Alzheimer's disease, etc., improved therapies are proposed for these disorders. These improvements stem from the unique properties of the estrogenic therapeutic compounds discussed below, which place them in a separate category of estrogenic compounds distinguished from the conventional physiological estrogens (e.g., estradiol and estrone). These properties include low toxicity, long acting effect, and the absence of any detectable carcinogenicity.

The estrogenic therapeutic compounds (particularly estrogenic carboxylic acids) used in accordance with this invention may also be a valuable research tool for testing the estrogen receptors and/or pathways involved in mediating the actions elicited by estrogenic and non-estrogenic compounds. As noted earlier, there is an apparent activity/binding paradox suggesting that the classic estrogen receptor, ER α, may not be the exclusive receptor or pathway mediating the actions of Z-BDDA compounds, or possibly even those of estradiol. Initial studies comparing the classical ER α and the novel estrogen receptor ER β show similar results. The binding affinity of (+)-Z-BDDA is even lower than that of the (−)-enantiomer, and both enantiomers have a much lower affinity for estrogen receptors than does estradiol, where measured via direct receptor binding assays or by generating does-response profiles using activation of estrogen-responsive reportes genes in cell-culture systems. Indeed, estradiol and other conventional estrogenic compounds appear to be dependent on high affinity binding to ER α and/or β for eliciting the classical estrogen response. This effect does not appear to be the case for the present estrogenic therapeutic compounds (particularly the estrogenic carboxylic acids), which suggests that these compounds are selective estrogen response modulators (SERMs) that elicit their estrogenic actions by a novel binding of the estrogen receptors, or by a mechanism that is independent of the estrogen receptor and which occurs elsewhere in the estrogen response pathway. Therefore, these estrogenic therapeutic compounds (particularly estrogenic carboxylic acids) have the potential for use as research tools in determining if a classical or novel estrogenic action is dependent on high affinity binding to ER α and/or β, or is elicited via low affinity binding to the estrogen receptors. Additionally, the present estrogenic compounds can be a valuable tool in elucidating and characterizing the mechanisms involved in the classical and novel estrogen signaling pathway, testing the estrogen receptors and/or pathways involved in mediating the actions elicited by estrogenic and non-estrogenic compounds. Sites of action of the present estrogenic compounds can also be detected by transcriptional initiation through a cotransfection assay.

A. Compounds

The estrogenic compounds useful in the methods of the present invention include, for example, doisynolic acid compounds, bisdehydrodoisynolic acid compounds, allenolic acid compounds, phenyl- and hydroxyphenylcyclohexane compounds, phenyl- and hydroxyphenylcyclohexene compounds, and hydroxytetrahydroanthracene compounds. Especially preferred compounds include, for example, doisynolic acid, bisdehydrodoisynolic acid, allenolic acid, phenyl- and hydroxyphenylcyclohexane carboxylic acids, phenyl- and hydroxyphenylcyclohexene carboxylic acids, and hydroxytetrahydroanthracene carboxylic acids.

In addition to the foregoing specific compounds, a number of derivatives thereof are also contemplated for use in the present methods. These include hydroxynaphthyl alkylated alkanoic acids, hydroxyphenyl alkylated cyclohexene- and cyclohexanecarboxylic acids, and hydroxyalkylated tetrahydro-anthracenecarboxylic acids, and the corresponding non-hydroxylated compounds which are hydroxylated in vivo, and thereby likewise exhibit estrogenic activity. Methods for preparing these derivatives involve conventional synthetic organic chemical reactions within the ordinary skill of the art.

In the various therapeutic methods disclosed herein, one can use the estrogenically active compounds of the present invention in their phenolic or non-phenolic forms, as free acids, or corresponding pharmaceutically acceptable salts, ethers, esters, or other easily hydrolyzable derivatives such as anhydrides, etc.

The preferred structures of the compounds for use in accordance with this invention are shown below. It should be noted that in some cases, only one enantiomeric structure is illustrated for each of a particular compound. However, as these compounds possess asymmetric carbon atoms, enantiomers and diastereomers other than those shown may exhibit specific biological activity. As it is known to those skilled in the art that the compounds of the present invention having such asymmetric carbon atoms can exist in enantiomeric, diastereomeric, and racemic forms, all these forms are contemplated within the scope of the present invention. More specifically, the present invention includes such enantiomers, diastereomers, racemic mixtures, and other mixtures thereof.

In one of the more preferred embodiments of this invention, the therapeutic estrogenic compound has the structure of formula (I) or is a pharmaceutically acceptable salt thereof:

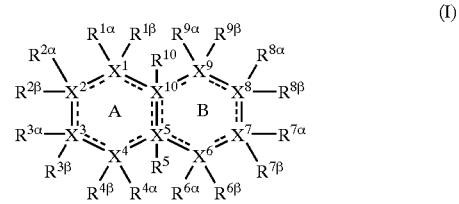

Here, $X^1$, $X^2$, $X^3$, $X^4$, $X^5$, $X^6$, $X^7$, $X^8$, $X^9$, and $X^{10}$ preferably are carbon atoms.

The dashed lines are optional π bonds (i.e., a bond represented by both a solid line and a dashed line may optionally be either a single or a double bond).

$R^{1\beta}$, $R^{2\beta}$, $R^{3\beta}$, $R^{4\beta}$, $R^5$, $R^{6\beta}$, $R^{7\beta}$, $R^{8\beta}$, $R^{9\beta}$, and/or $R^{10}$ are present only when $X^1$, $X^2$, $X^3$, $X^4$, $X^5$, $X^6$, $X^7$, $X^8$, $X^9$, and/or $X^{10}$, respectively, are saturated (i.e., are bound to 4 atoms).

$R^{1\alpha}$ and $R^{2\alpha}$ preferably are independently a moiety which (a) comprises from 1 to 20 carbon atoms (more preferably from 1 to 6 carbon atoms), and is selected from the group consisting of hydrocarbyl and substituted hydrocarbyl (i.e., $R^{1\alpha}$ and $R^{2\alpha}$ are independently a carbon-containing moiety which comprises no greater than 20 carbon atoms, and more preferably no greater than 6 carbon atoms); or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{1\alpha}$ and $R^{2\alpha}$ are independently selected from the group consisting of hydrogen; hydrocarbyl comprising from 1 to 6 carbon atoms; and —OR$^{100}$, wherein $R^{100}$ is hydrogen or hydrocarbyl containing from 1 to 6 carbon atoms, and particularly wherein $R^{100}$ is hydrogen or methyl. Most preferably, $R^{1\alpha}$ and $R^{2\alpha}$ are hydrogen.

$R^{1\beta}$, $R^{2\beta}$, $R^{3\beta}$, $R^{4\beta}$, $R^5$, $R^{6\beta}$, $R^{8\beta}$, $R^{9\beta}$, and $R^{10}$ preferably are independently a moiety which (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{1\beta}$, $R^{2\beta}$, $R^{3\beta}$, $R^{4\beta}$, $R^5$, $R^{6\beta}$, $R^{8\beta}$, $R^{9\beta}$, and $R^{10}$ are independently selected from the group consisting of hydrogen and hydrocarbyl comprising from 1 to 6 carbon atoms. Most preferably, $R^{1\beta}$, $R^{2\beta}$, $R^{3\beta}$, $R^{4\beta}$, $R^5$, $R^{6\beta}$, $R^{8\beta}$, $R^{9\beta}$, and $R^{10}$ are hydrogen.

$R^{3\alpha}$ preferably (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. In a more preferred embodiment, $R^{3\alpha}$ is hydrogen. In another more preferred embodiment, $R^{3\alpha}$ is selected from the group consisting of glycosidyl, acetylated glycosidyl, and malonylated glycosidyl. In an additional more preferred embodiment, $R^{3\alpha}$ is —OC(O)($R^{101}$), wherein $R^{101}$ is benzyl or —N(CH$_2$CH$_2$Cl)$_2$. In yet another more preferred embodiment, $R^{3\alpha}$ comprises (a) no greater than 20 carbon atoms (more preferably, no greater than 6 carbon atoms); and (b) a moiety selected from the group consisting of amino, halogen, hydrogen, imino, oximido, oxo, oxy, phosphinidene, phosphino, phosphinyl, phosphinylidene, phosphono, phosphoranyl, phosphoranylidene, siloxy, silyl, silylene, sulfeno, sulfino, sulfo, and thio. In an even more preferred embodiment, $R^{3\alpha}$ comprises (a) no greater than 20 carbon atoms (more preferably, no greater than 6 carbon atoms); and (b) a moiety selected from the group consisting of amino, imino, oximido, oxy, phosphinidene, phosphino, phosphinyl, phosphinylidene, phosphono, phosphoranyl, phosphoranylidene, siloxy, silyl, silylene, sulfeno, sulfino, sulfo, and thio. In a still even more preferred embodiment, $R^{3\alpha}$ comprises a polarizable hydrogen atom (i.e., a hydrogen atom bound to an atom other than a carbon atom), and is, for example, —C(O)(OH), —NH$_2$, =NH, =N(OH), —OH, =PH, —PH$_2$, —P(O)(H)(H), =P(O)(H), —P(O)(OH)(OH), —PH$_4$, =PH$_3$, =SiH$_2$, —S(OH), —S(O)(OH), S(O)(O)(OH), or —SH. In an alternative even more preferred embodiment, $R^{3\alpha}$ is —OR$^{102}$ or —OC(O)(R$^{103}$), wherein $R^{102}$ and $R^{103}$ are hydrogen, halogen, or hydrocarbyl comprising from 1 to 19 carbon atoms (particularly 1 to 5 carbon atoms, and more particularly from 1 to 2 carbon atoms). Most preferably, $R^{3\alpha}$ is —OH.

$R^{4\alpha}$, $R^{6\alpha}$, and $R^{9\alpha}$ preferably are independently a moiety which (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{4\alpha}$, $R^{6\alpha}$, and $R^{9\alpha}$ are independently selected from the group consisting of hydrogen and hydrocarbyl comprising from 1 to 6 carbon atoms. Most preferably, $R^{4\alpha}$, $R^{6\alpha}$, and $R^{9\alpha}$ are hydrogen.

$R^{7\alpha}$ preferably (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{7\alpha}$ is selected from the group consisting of hydrogen, hydrocarbyl comprising from 1 to 20 carbon atoms, and oxo. Most preferably, $R^{7\alpha}$ is hydrogen.

$R^{7\beta}$ preferably (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{7\beta}$ is selected from the group consisting of hydrogen and hydrocarbyl comprising from 1 to 6 carbon atoms. Most preferably, $R^{7\beta}$ is hydrogen.

$R^{8\alpha}$ preferably is a substituted hydrocarbyl comprising a moiety selected from the group consisting of amino, imino, oximido, oxy, phosphinidene, phosphino, phosphinyl, phosphinylidene, phosphono, phosphoranyl, phosphoranylidene, siloxy, silyl, silylene, sulfeno, sulfino, sulfo, and thio. More preferably, $R^{8\alpha}$ comprises a substituted hydrocarbyl containing a polarizable hydrogen atom ($R^{8\alpha}$ is, for example, —C(O)(OH), —NH$_2$, =NH, =N(OH), —OH, =PH, —PH$_2$, —P(O)(H)(H), =P(O)(H), —P(O)(OH)(OH), —PH$_4$, =PH$_3$, =SiH$_2$, —S(OH), —S(O)(OH), S(O)(O)(OH), or —SH). In an alternative more preferred embodiment, $R^{8\alpha}$ is a substituted hydrocarbyl comprising —C(O)(OR$^{104}$), wherein $R^{104}$ is hydrogen, halogen, or hydrocarbyl comprising from 1 to 5 carbon atoms (particularly from 1 to 2 carbon atoms). Most preferably, $R^{8\alpha}$ is a substituted hydrocarbyl comprising —C(O)(OH), making the compound an estrogenic carboxylic acid. In a particularly preferred embodiment, $R^{8\alpha}$ comprises no greater than 20 carbon atoms.

In some instances, it is preferred that the therapeutic compound of formula (I) have the structure of formula (II) or be a pharmaceutically acceptable salt thereof:

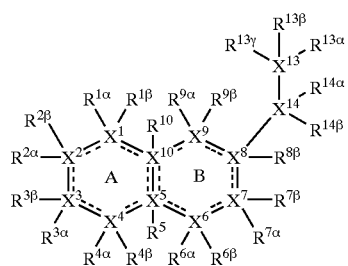

Here, $X^1$, $X^2$, $X^3$, $X^4$, $X^5$, $X^6$, $X^7$, $X^8$, $X^9$, $X^{10}$, $R^{1\alpha}$, $R^{1\beta}$, $R^{2\alpha}$, $R^{2\beta}$, $R^{3\alpha}$, $R^{3\beta}$, $R^{4\alpha}$, $R^{4\beta}$, $R^5$, $R^{6\alpha}$, $R^{6\beta}$, $R^{7\alpha}$, $R^{7\beta}$, $R^{8\beta}$, $R^{9\alpha}$, $R^{9\beta}$, and $R^{10}$ are preferably as defined above for formula (I).

$X^{13}$ and $X^{14}$ preferably are carbon atoms.

The dashed lines are optional π bonds.

$R^{1\beta}$, $R^{2\beta}$, $R^{3\beta}$, $R^{4\beta}$, $R^5$, $R^{6\beta}$, $R^{7\beta}$, $R^{8\beta}$, $R^{9\beta}$, $R^{10}$, $R^{13\gamma}$, and/or $R^{14\beta}$ are present only when $X^1$, $X^2$, $X^3$, $X^4$, $X^5$, $X^6$, $X^7$, $X^8$, $X^9$, $X^{10}$, $X^{13}$, and/or $X^{14}$, respectively, are saturated.

$R^{13\alpha}$ preferably comprises (a) no greater than 20 carbon atoms (more preferably no greater than 6 carbon atoms); and (b) a moiety selected from the group consisting of amino, imino, oximido, oxy, phosphinidene, phosphino, phosphinyl, phosphinylidene, phosphono, phosphoranyl, phosphoranylidene, siloxy, silyl, silylene, sulfeno, sulfino, sulfo, and thio. More preferably, $R^{13\alpha}$ comprises a polarizable hydrogen atom and is, for example, —C(O)(OH), —NH$_2$, =NH, =N(OH), —OH, =PH, —PH$_2$, —P(O)(H)(H), =P(O)(H), —P(O)(OH)(OH), —PH$_4$, =PH$_3$, =SiH$_2$, —S(OH), —S(O)(OH), S(O)(O)(OH), or —SH. In an alternative more preferred embodiment, $R^{13\alpha}$ is —C(O)(OR$^{105}$), wherein $R^{105}$ is hydrogen, halogen, or hydrocarbyl comprising from 1 to 5 carbon atoms. Most preferably, $R^{13\alpha}$ is —C(O)(OH) (i.e., the compound is an estrogenic carboxylic acid).

$R^{13\beta}$ preferably (a) comprises from 1 to 20 carbon atoms (more preferably no greater than 6 carbon atoms), and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{13\beta}$ is selected from the group consisting of hydrogen and hydrocarbyl comprising from 1 to 6 carbon atoms. Even more preferably, $R^{13\beta}$ is are independently hydrocarbyl comprising from 1 to 6 carbon atoms. Most preferably, $R^{13\beta}$ is methyl.

$R^{13\gamma}$ preferably (a) comprises from 1 to 20 carbon atoms (more preferably no greater than 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{13\gamma}$ is selected from the group consisting of hydrogen and hydrocarbyl comprising from 1 to 6 carbon atoms. Even more preferably, $R^{13\gamma}$ is hydrocarbyl comprising from 1 to 6 carbon atoms. Most preferably, $R^{13\gamma}$ is methyl.

$R^{14\alpha}$ preferably (a) comprises from 1 to 20 carbon atoms (more preferably no greater than 6 carbon atoms), and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{14\alpha}$ is selected from the group consisting of hydrogen and hydrocarbyl comprising from 1 to 6 carbon atoms. Even more preferably, $R^{14\alpha}$ is hydrocarbyl comprising from 1 to 6 carbon atoms. Most preferably, $R^{14\alpha}$ is ethyl.

$R^{14\beta}$ preferably (a) comprises from 1 to 20 (more preferably no greater than 6 carbon atoms), carbon atoms and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{14\beta}$ is selected from the group consisting of hydrogen and hydrocarbyl comprising from 1 to 6 carbon atoms. Most preferably, $R^{14\beta}$ is hydrogen.

One particularly preferred structure of formula (II) is "allenolic acid" (or "AA"), which has the following formula (III):

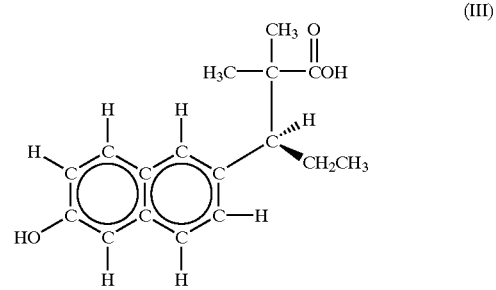

In other instances, it is particularly preferred for $R^{8\alpha}$ to form a carbocyclic ring with $R^{9\alpha}$ in formula (I) to create, for example, a doisynolic acid derivative having the formula (IV) or a pharmaceutically acceptable salt thereof:

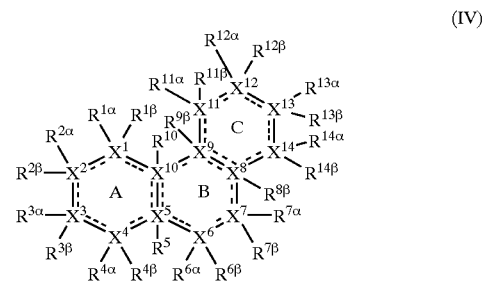

Here, $X^1$, $X^2$, $X^3$, $X^4$, $X^5$, $X^6$, $X^7$, $X^8$, $X^9$, $X^{10}$, $R^{1\alpha}$, $R^{1\beta}$, $R^{2\alpha}$, $R^{2\beta}$, $R^{3\alpha}$, $R^{3\beta}$, $R^{4\alpha}$, $R^{4\beta}$, $R^5$, $R^{6\alpha}$, $R^{6\beta}$, $R^{7\alpha}$, $R^{7\beta}$, $R^{8\beta}$, $R^{9\alpha}$, $R^{9\beta}$, and $R^{10}$ are preferably as defined above for formula (I).

$X^{11}$, $X^{12}$, $X^{13}$ and $X^{14}$ preferably are carbon atoms.

The dashed lines are optional π bonds.

$R^{1\beta}$, $R^{2\beta}$, $R^{3\beta}$, $R^{4\beta}$, $R^5$, $R^{6\beta}$, $R^{7\beta}$, $R^{8\beta}$, $R^{9\beta}$, $R^{10}$, $R^{11\beta}$, $R^\beta$, $R^{13\gamma}$, and/or $R^{14\beta}$ are present only when $X^1$, $X^2$, $X^3$, $X^4$, $X^5$, $X^6$, $X^7$, $X^8$, $X^9$, $X^{10}$, $X^{11}$, $X^{12}$, $X^{13}$, and/or $X^{14}$, respectively, are saturated.

$R^{11\beta}$ and $R^{12\alpha}$ preferably are independently a moiety which (a) comprises from 1 to 20 carbon atoms (more preferably, from 1 to 6 carbon atoms), and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidine, phosphino, phosphinyl, phosphinylidene, phospho, phosphono, phosphoranyl, phosphoranylidene, phosphoroso, siloxy, silyl, silyene, sulfeno, sulfinyl, sulfino, sulfo, sulfonyl, thio, and thioxo. More preferably, $R^{11\alpha}$ and $R^{12\alpha}$ are independently selected from the group consisting of hydrogen and hydrocarbyl comprising from 1 to 6 carbon atoms. Most preferably, $R^{11\alpha}$ and $R^{12\alpha}$ are hydrogen.

$R^{11\beta}$, $R^{12\beta}$, and $R^{14\beta}$ preferably are independently a moiety which (a) comprises from 1 to 20 carbon atoms (more preferably, from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{11\beta}$, $R^{12\beta}$, and $R^{14\beta}$ are independently selected from the group consisting of hydrogen and hydrocarbyl comprising from 1 to 6 carbon atoms. Most preferably, $R^{11\beta}$, $R^{12\beta}$, and $R^{14\beta}$ are hydrogen.

$R^{13\alpha}$ preferably comprises (a) no greater than 20 carbon atoms (more preferably no greater than 6 carbon atoms); and (b) a moiety selected from the group consisting of amino, imino, oximido, oxy, phosphinidene, phosphino, phosphinyl, phosphinylidene, phosphono, phosphoranyl, phosphoranylidene, siloxy, silyl, silylene, sulfeno, sulfino, sulfo, and thio. More preferably, $R^{13\alpha}$ comprises a polarizable hydrogen atom and is, for example, —C(O)(OH), —NH$_2$, =NH, =N(OH), —OH, =PH, —PH$_2$, —P(O)(H)(H), =P(O)(H), —P(O)(OH)(OH), —PH$_4$, =PH$_3$, =SiH$_2$, —S(OH), —S(O)(OH), S(O)(O)(OH), or —SH. In an alternative more preferred embodiment, $R^{13\alpha}$ is —C(O)(OR$^{106}$), wherein $R^{106}$ is hydrogen, halogen, or hydrocarbyl comprising from 1 to 5 carbon atoms. Most preferably, $R^{13\alpha}$ is —C(O)(OH) (i.e., the compound is an estrogenic carboxylic acid).

$R^{13\beta}$ preferably (a) comprises from 1 to 20 carbon atoms and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{13\beta}$ is selected from the group consisting of hydrogen and hydrocarbyl comprising from 1 to 6 carbon atoms. Even more preferably, $R^{13\beta}$ is hydrocarbyl comprising from 1 to 6 carbon atoms. Most preferably, $R^{13\beta}$ is methyl.

$R^{14\alpha}$ preferably (a) comprises from 1 to 20 carbon atoms and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{14\alpha}$ is selected from the group consisting of hydrogen and hydrocarbyl comprising from 1 to 6 carbon atoms. Even more preferably, $R^{14\alpha}$ is hydrocarbyl comprising from 1 to 6 carbon atoms. Most preferably, $R^{14\alpha}$ is ethyl.

It is especially preferred for the A ring of formula (IV) to be aromatic, as shown in formula (V):

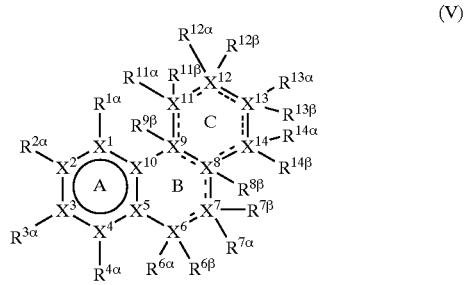

(V)

Here, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $R^{6\alpha}$, $R^{6\beta}$, $R^{7\alpha}$, $R^{7\beta}$, $R^{8\beta}$, $R^{9\beta}$, $R^{11\alpha}$, $R^{11\beta}$, $R^{12\alpha}$, $R^{12\beta}$, $R^{13\alpha}$, $R^{13\beta}$, $R^{14\alpha}$ and $R^{14\beta}$ preferably are as defined above for formula (IV).

The dashed lines are optional π bonds.

$R^{6\beta}$, $R^{7\beta}$, $R^{8\beta}$, $R^{9\beta}$, $R^{11\beta}$, $R^{12\beta}$, $R^{13\beta}$, and/or $R^{14\beta}$ are present only when $X^6$, $X^7$, $X^8$, $X^9$, $X^{11}$, $X^{12}$, $X^{13}$, and/or $X^{14}$, respectively, are saturated.

$R^{1\alpha}$ and $R^{2\alpha}$ preferably are independently a moiety which (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{1\alpha}$ and $R^{2\alpha}$ are independently selected from the group consisting of hydrogen; hydrocarbyl comprising from 1 to 6 carbon atoms; and —OR$^{107}$, wherein $R^{107}$ is hydrogen or hydrocarbyl containing from 1 to 6 carbon atoms, and particularly wherein $R^{107}$ is hydrogen or methyl. Most preferably, $R^{1\alpha}$ and $R^{2\alpha}$ are hydrogen.

$R^{3\alpha}$ preferably (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. In a more preferred embodiment, $R^{3\alpha}$ is hydrogen. In another more preferred embodiment, $R^{3\alpha}$ is selected from the group consisting of glycosidyl, acetylated glycosidyl, and malonylated glycosidyl. In an additional more preferred embodiment, $R^{3\alpha}$ is —OC(O)(R$^{108}$), wherein $R^{108}$ is benzyl or —N(CH$_2$CH$_2$Cl)$_2$. In yet another more preferred embodiment, $R^3$, comprises (a) no greater than 20 carbon atoms (more preferably, no greater than 6 carbon atoms); and (b) a moiety selected from the group consisting of amino, imino, oximido, oxy, phosphinidene, phosphino, phosphinyl, phosphinylidene, phosphono, phosphoranyl, phosphoranylidene, siloxy, silyl, silylene, sulfeno, sulfino, sulfo, and thio. In an even more preferred embodiment, $R^{3\alpha}$ comprises a polarizable hydrogen atom and is, for example, —C(O)(OH), —NH$_2$, =NH, =N(OH), —OH, =PH, —PH$_2$, —P(O)(H)(H), =P(O)(H), —P(O)(OH)(OH), —PH$_4$, =PH$_3$, =SiH$_2$, —S(OH), —S(O)(OH), S(O)(O)(OH), or —SH. In an alternative even more preferred embodiment, $R^{3\alpha}$ is —OR$^{109}$ or —OC(O)R$^{110}$, wherein $R^{109}$ and $R^{110}$ are hydrogen, halogen, or hydrocarbyl comprising from 1 to 19 carbon atoms (particularly 1 to 5 carbon atoms, and more particularly 1 to 2 carbon atoms). Most preferably, $R^{3\alpha}$ is —OH.

$R^{4\alpha}$ preferably (a) comprises from 1 to 20 carbon atoms (more preferably from 1 to 6 atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{4\alpha}$ is selected from the group consisting of hydrogen and hydrocarbyl comprising from 1 to 6 carbon atoms. Most preferably, $R^{4\alpha}$ is hydrogen.

In another especially preferred embodiment using the compound of formula (V) or a pharmaceutically acceptable salt thereof, no π bonds exist in the bond positions represented by both a solid line and a dashed line (i.e., all the bonds in those positions are single bonds) in formula (V), and the compound consequently has formula (VI) or is a pharmaceutically acceptable salt thereof:

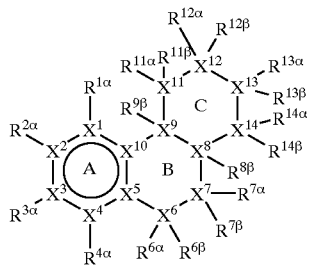

(VI)

Here, $X^1, X^2, X^3, X^4, X^5, X^6, X^7, X^8, X^9, X^{10}, X^{11}, X^{12}, X^{13}, X^{14}, R^{1\alpha}, R^{2\alpha}, R^{3\alpha}, R^{4\alpha}, R^{6\alpha}, R^{6\beta}, R^{7\alpha}, R^{7\beta}, R^{8\beta}, R^{9\beta}, R^{11\alpha}, R^{11\beta}, R^{12\alpha}, R^{12\beta}, R^{13\alpha}, R^{13\beta}, R^{14\alpha}$ and $R^{14\beta}$ preferably are as defined above for formula (V).

$R^{6\beta}, R^{7\beta}, R^{11\beta}, R^{12\beta}, R^{13\beta}$, and $R^{14\beta}$ are present only when $X^6, X^7, X^{11}, X^{12}, X^{13}$, and/or $X^{14}$, respectively, are saturated.

When using the compound of formula (VI) or a pharmaceutically acceptable salt thereof, it is especially preferred for $R^{1\alpha}, R^{2\alpha}, R^{4\alpha}, R^{6\alpha}, R^{6\beta}, R^{7\alpha}, R^{7\beta}, R^{8\beta}, R^{9\beta}, R^{11\alpha}, R^{11\beta}, R^{12\alpha}, R^{12\beta}$, and $R^{14\beta}$ to be hydrogen; $R^{3\alpha}$, to be —OH; $R^{13\alpha}$ to be —C(O)(OH) (i.e., the compound is an estrogenic carboxylic acid); $R^{13\beta}$ to be methyl; and $R^{14\alpha}$ to be ethyl. Such a compound most preferably has the formula (VII) or is a pharmaceutically acceptable salt thereof:

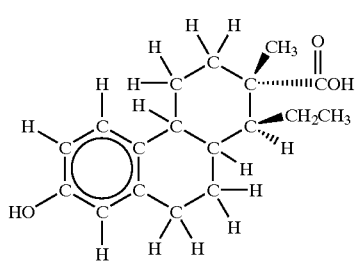

(VII)

In another particularly preferred embodiment, the compound of formula (V) or the pharmaceutically acceptable salt thereof has the formula (VIII) or is a pharmaceutically acceptable salt thereof:

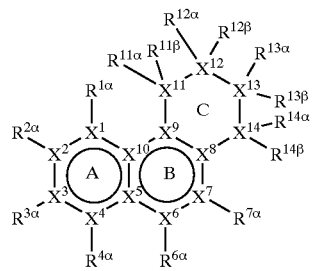

(VIII)

Here, $X^1, X^2, X^3, X^4, X^5, X^6, X^7, X^8, X^9, X^{10}, X^{11}, X^{12}, X^{13}, X^{14}, R^{1\alpha}, R^{2\alpha}, R^{3\alpha}, R^{4\alpha}, R^{11\alpha}, R^{11\beta}, R^{12\alpha}, R^{12\beta}, R^{13\alpha}, R^{13\beta}, R^{14\alpha}$, and $R^{14\beta}$ preferably are as defined above for formula (V).

$R^{11\beta}, R^{12\beta}, R^{13\beta}$, and/or $R^{14\beta}$ are present only when $X^{11}, X^{12}, X^{13}$, and/or $X^{14}$, respectively, are saturated.

$R^{6\alpha}$ preferably (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{6\alpha}$ is selected from the group consisting of hydrogen and hydrocarbyl comprising from 1 to 6 carbon atoms. Most preferably, $R^{6\alpha}$ is hydrogen.

$R^{7\alpha}$ preferably (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{7\alpha}$ is selected from the group consisting of hydrogen and hydrocarbyl comprising from 1 to 20 carbon atoms. Most preferably, $R^{7\alpha}$ is hydrogen.

When the compound has formula (VIII), it is especially preferred for $R^{1\alpha}, R^{2\alpha}, R^{4\alpha}, R^{6\alpha}, R^{7\alpha}, R^{11\alpha}, R^{11\beta}, R^{12\alpha}, R^{12\beta}$, and $R^{14\beta}$ to be hydrogen; $R^{3\alpha}$ to be —OH; $R^{13\alpha}$ to be —C(O)(OH) (i.e., the compound is an estrogenic carboxylic acid); $R^{13\beta}$ to be methyl; and $R^{14\alpha}$ to be ethyl. Such a compound, for example, may have the formula (IX):

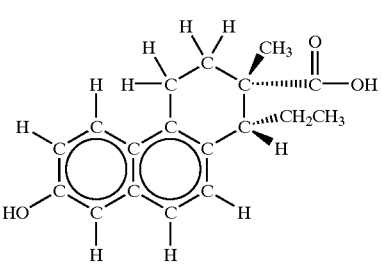

(IX)

This compound is sometimes described herein as "(−)-Z-bisdehydrodoisynolic acid" (or "(−)-Z-BDDA"). Its enantiomer has the formula (X):

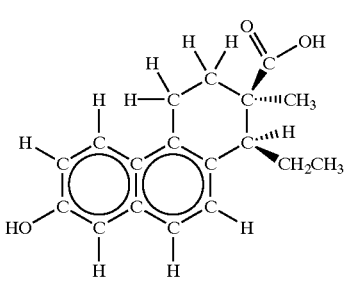

(X)

This compound is sometimes described herein as "(+)-Z-bisdehydrodoisynolic acid" (or "(+)-Z-BDDA"). Depending on the therapeutic application, either formula (IX) or formula (X) is most preferred.

In some instances, it is particularly preferred for $R^{8\alpha}$ in Formula (I) to form a carbocyclic ring with $R^{7\alpha}$ to form a compound having the formula (XI) or a pharmaceutically acceptable salt thereof:

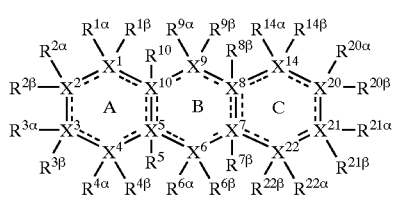

(XI)

Here, $X^1$, $X^2$, $X^3$, $X^4$, $X^5$, $X^6$, $X^7$, $X^8$, $X^9$, $X^{10}$, $R^{1\alpha}$, $R^{1\beta}$, $R^{2\alpha}$, $R^{2\beta}$, $R^{3\alpha}$, $R^{3\beta}$, $R^{4\alpha}$, $R^{4\beta}$, $R^5$, $R^{6\alpha}$, $R^{6\beta}$, $R^{7\beta}$, $R^{8\beta}$, $R^{9\alpha}$, $R^{9\beta}$, and $R^{10}$ are preferably as defined above for formula (I).

$X^{14}$, $X^{20}$, $X^{21}$, and $X^{22}$ preferably are carbon atoms.

The dashed lines are optional π bonds.

$R^{1\beta}$, $R^{2\beta}$, $R^{3\beta}$, $R^{4\beta}$, $R^5$, $R^{6\beta}$, $R^{7\beta}$, $R^{8\beta}$, $R^{9\beta}$, $R^{10}$, $R^{14\beta}$, $R^{20\beta}$, $R^{21\beta}$, and/or $R^{22\beta}$ are present only when $X^1$, $X^2$, $X^3$, $X^4$, $X^5$, $X^6$, $X^7$, $X^8$, $X^9$, $X^{10}$, $X^{14}$, $X^{20}$, $X^{21}$, and/or $X^{22}$, respectively, are saturated.

$R^{21\alpha}$ and $R^{22\alpha}$ preferably are independently a moiety which (a) comprises from 1 to 20 carbon atoms (more preferably, from 1 to 6 carbon atoms), and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{21\alpha}$ and $R^{22\alpha}$ are independently selected from the group consisting of hydrogen and hydrocarbyl comprising from 1 to 6 carbon atoms. Most preferably, $R^{21\alpha}$ and $R^{22\alpha}$ are hydrogen.

$R^{21\beta}$, $R^{22\beta}$, and $R^{14\beta}$ preferably are independently a moiety which (a) comprises from 1 to 20 carbon atoms (more preferably, from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoranylidene, silyl, sulfeno, sulfino, sulfo, sulfonyl, and thio. More preferably, $R^{21\beta}$, $R^{22\beta}$, and $R^{14\beta}$ are independently selected from the group consisting of hydrogen and hydrocarbyl comprising from 1 to 6 carbon atoms. Most preferably, $R^{21\beta}$, $R^{22\beta}$, and $R^{14\beta}$ are hydrogen.

$R^{20\alpha}$ preferably comprises (a) no greater than 20 carbon atoms (more preferably no greater than 6 carbon atoms); and (b) a moiety selected from the group consisting of amino, imino, oximido, oxy, phosphinidene, phosphino, phosphinyl, phosphinylidene, phosphono, phosphoranyl, phosphoranylidene, siloxy, silyl, silylene, sulfeno, sulfino, sulfo, and thio. More preferably, $R^{20\alpha}$ comprises a polarizable hydrogen atom and is, for example, —C(O)(OH), —NH2, =NH, =N(OH), —OH, =PH, —PH$_2$, —P(O)(H)(H), =P(O)(H), —P(O)(OH)(OH), —PH$_4$, =PH$_3$, =SiH$_2$, —S(OH), —S(O)(OH), S(O)(O)(OH), or —SH. In an alternative more preferred embodiment, $R^{20\alpha}$ is —C(O)(OR$^{111}$), wherein R$^{111}$ is hydrogen, halogen, or hydrocarbyl comprising from 1 to 5 carbon atoms. Most preferably, $R^{20\alpha}$ is —C(O)(OH) (i.e., the compound is an estrogenic carboxylic acid).

$R^{20\beta}$ preferably (a) comprises from 1 to 20 carbon atoms and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{20\beta}$ is selected from the group consisting of hydrogen and hydrocarbyl comprising from 1 to 6 carbon atoms. Even more preferably, $R^{20\beta}$ is hydrocarbyl comprising from 1 to 6 carbon atoms. Most preferably, $R^{20\beta}$ is methyl.

$R^{14\alpha}$ preferably (a) comprises from 1 to 20 carbon atoms and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{14\alpha}$ is selected from the group consisting of hydrogen and hydrocarbyl comprising from 1 to 6 carbon atoms. Even more preferably, $R^{14\alpha}$ is hydrocarbyl comprising from 1 to 6 carbon atoms. Most preferably, $R^{14\alpha}$ is ethyl.

When the compound has formula (XI), it is particularly preferred for the A and B rings to be aromatic; $R^{1\alpha}$, $R^{2\alpha}$, $R^{4\alpha}$, $R^{6\alpha}$, $R^{9\alpha}$, $R^{14\beta}$, $R^{21\alpha}$, $R^{21\beta}$, $R^{22\alpha}$ and $R^{22\beta}$ to be hydrogen; $R^{3\alpha}$, to be —OH; $R^{14\alpha}$ to be ethyl; $R^{20\alpha}$ to be —C(O)(OH) (i.e., the compound is an estrogenic carboxylic acid); $R^{20\beta}$ to be methyl. Most preferably, such a compound is formula (XII) or a pharmaceutically acceptable salt thereof:

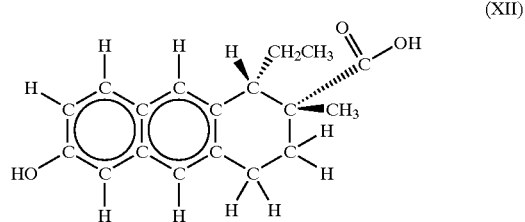

(XII)

This compound is sometimes referred to herein as 1-ethyl-6-hydroxy-2-methyl-1,2,3,4-tetrahydroanthracene-2-carboxylic acid.

In another of the more preferred embodiments of this invention, the compound has the structure of formula (XIII) or is a pharmaceutically acceptable salt thereof:

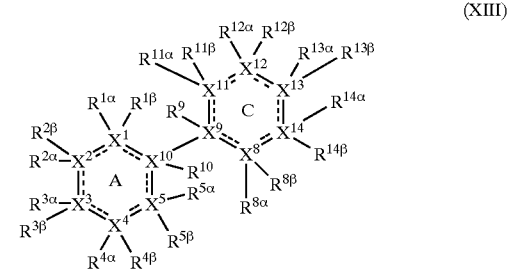

(XIII)

Here, $X^1$, $X^2$, $X^3$, $X^4$, $X^5$, $X^8$, $X^9$, $X^{10}$, $X^{11}$, X12, $X^{13}$, and $X^{14}$ preferably are carbon atoms.

The dashed lines are optional π bonds.

$R^{1\beta}$, $R^{2\beta}$, $R^{3\beta}$, $R^{4\beta}$, $R^{5\beta}$, R8β, $R^9$, $R^{10}$, $R^{11\beta}$, $R^{12\beta}$, $R^{13\beta}$, and/or $R^{14\beta}$ are when $X^1$, $X^2$, $X^3$, $X^4$, $X^5$, $X^8$, $X^9$, $X^{10}$, $X^{11}$, $X^{12}$, $X^{13}$, and/or $X^{14}$, respectively, are saturated.

$R^{1\alpha}$ and $R^{2\alpha}$ preferably are independently a moiety which (a) comprises from 1 to 20 carbon atoms (more preferably from 1 to 6 carbon atoms), and is selected from the group consisting of hydrocarbyl and substituted hydrocarbyl; or (b)

does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{1\alpha}$ and $R^{2\alpha}$ are independently selected from the group consisting of hydrogen; hydrocarbyl comprising from 1 to 6 carbon atoms; and —$OR^{112}$, wherein $R^{112}$ is hydrogen or hydrocarbyl containing from 1 to 6 carbon atoms, and particularly wherein $R^{112}$ is hydrogen or methyl. Most preferably, $R^{1\alpha}$ and $R^{2\alpha}$ are hydrogen.

$R^{1\beta}$, $R^{2\beta}$, $R^{3\beta}$, $R^{4\beta}$, $R^{5\beta}$, $R^{8\beta}$, $R^9$, $R^{10}$, $R^{11\beta}$, and $R^{13\beta}$ preferably are independently a moiety which (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{1\beta}$, $R^{2\beta}$, $R^{3\beta}$, $R^{4\beta}$, $R^{5\beta}$, $R^{8\beta}$, $R^9$, $R^{10}$, $R^{11\beta}$, and $R^{13\beta}$ are independently selected from the group consisting of hydrogen and hydrocarbyl comprising from 1 to 6 carbon atoms. Most preferably, $R^{1\beta}$, $R^{2\beta}$, $R^{3\beta}$, $R^{4\beta}$, $R^{5\beta}$, $R^{8\beta}$, $R^9$, $R^{10}$, $R^{11\beta}$, and $R^{13\beta}$ are hydrogen.

$R^{3\alpha}$ preferably (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. In a more preferred embodiment, $R^{3\alpha}$ is hydrogen. In another more preferred embodiment, $R^{3\alpha}$ is selected from the group consisting of glycosidyl, acetylated glycosidyl, and malonylated glycosidyl. In an additional more preferred embodiment, $R^{3\alpha}$ is —$OC(O)(R^{114})$ wherein $R^{114}$ is benzyl or —$N(CH_2CH_2Cl)_2$. In yet another more preferred embodiment, $R^{3\alpha}$ comprises (a) no greater than 20 carbon atoms (more preferably, no greater than 6 carbon atoms); and (b) a moiety selected from the group consisting of amino, halogen, hydrogen, imino, oximido, oxo, oxy, phosphinidene, phosphino, phosphinyl, phosphinylidene, phosphono, phosphoranyl, phosphoranylidene, siloxy, silyl, silylene, sulfeno, sulfino, sulfo, and thio. In an even more preferred embodiment, $R^{3\alpha}$ comprises (a) no greater than 20 carbon atoms (more preferably, no greater than 6 carbon atoms); and (b) a moiety selected from the group consisting of amino, imino, oximido, oxy, phosphinidene, phosphino, phosphinyl, phosphinylidene, phosphono, phosphoranyl, phosphoranylidene, siloxy, silyl, silylene, sulfeno, sulfino, sulfo, and thio. In a still even more preferred embodiment, $R^{3\alpha}$ comprises a polarizable hydrogen atom, and is, for example, —C(O)(OH), —$NH_2$, =NH, =N(OH), —OH, =PH, —$PH_2$, —P(O)(H)(H), =P(O)(H), —P(O)(OH)(OH), —$PH_4$, =$PH_3$, =$SiH_2$, —S(OH), —S(O)(OH), S(O)(O)(OH), or —SH. In an alternative even more preferred embodiment, $R^{3\alpha}$ is —$OR^{115}$ or —$OC(O)R^{116}$, wherein $R^{115}$ and $R^{116}$ are hydrogen, halogen, or hydrocarbyl comprising from 1 to 19 carbon atoms (particularly 1 to 5 carbon atoms, and more particularly from 1 to 2 carbon atoms). Most preferably, $R^{3\alpha}$ is —OH.

$R^{4\alpha}$, $R^{5\alpha}$, and $R^{11\alpha}$ preferably are independently a moiety which (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{4\alpha}$, $R^{5\alpha}$, and $R^{11\alpha}$ are independently selected from the group consisting of hydrogen and hydrocarbyl comprising from 1 to 6 carbon atoms. Most preferably, $R^{4\alpha}$, $R^{5\alpha}$, and $R^{11\alpha}$ are hydrogen.

$R^{8\alpha}$, $R^{12\alpha}$, and $R^{14\alpha}$ preferably are independently a moiety which (a) comprises from 1 to 20 carbon atoms and is selected from the group consisting of hydrocarbyl and substituted hydrocarbyl; or (b) does not comprise a carbon atom and is selected from the group consisting of amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, and thioxo. More preferably, $R^{8\alpha}$, $R^{12\alpha}$, and $R^{14\alpha}$ are independently selected from the group consisting of hydrogen and hydrocarbyl comprising from 1 to 6 carbon atoms (particularly from 1 to 2 carbon atoms).

$R^{13\alpha}$ preferably comprises (a) no greater than 20 carbon atoms (more preferably no greater than 6 carbon atoms); and (b) a moiety selected from the group consisting of amino, imino, oximido, oxy, phosphinidene, phosphino, phosphinyl, phosphinylidene, phosphono, phosphoranyl, phosphoranylidene, siloxy, silyl, silylene, sulfeno, sulfino, sulfo, and thio. More preferably, $R^{13\alpha}$ comprises a polarizable hydrogen atom and is, for example, —C(O)(OH), —$NH_2$, =NH, =N(OH), —OH, =PH, —$PH_2$, —P(O)(H)(H), =P(O)(H), —P(O)(OH)(OH), —$PH_4$, =$PH_3$, =$SiH_2$, —S(OH), —S(O)(OH), S(O)(O)(OH), or —SH. In an alternative more preferred embodiment, $R^{13\alpha}$ is —$C(O)(OR^{117})$, wherein $R^{117}$ is hydrogen, halogen, or hydrocarbyl comprising from 1 to 5 carbon atoms. Most preferably, $R^{13\alpha}$ is —C(O)(OH) (i.e., the compound is an estrogenic carboxylic acid).

$R^{12\beta}$ and $R^{14\beta}$ preferably are independently a moiety which (a) comprises from 1 to 20 carbon atoms and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{12\beta}$ and $R^{14\beta}$ are independently selected from the group consisting of hydrogen and hydrocarbyl comprising from 1 to 6 carbon atoms (particularly from 1 to 2 carbon atoms).

When the compound has the structure of formula (XIII) or is a pharmaceutically acceptable salt thereof, it is particularly preferred for the compound to have formula (XIV) or be a pharmaceutically acceptable thereof:

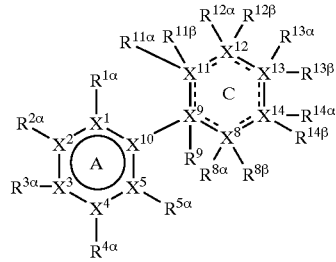

(XIV)

Here, $X^1, X^2, X^3, X^4, X^5, X^8, X^9, X^{10}, X^{11}, X^{12}, X^{13}, X^{14}$, $R^{8\alpha}, R^{8\beta}, R^9, R^{11\alpha}, R^{11\beta}, R^{12\alpha}, R^{12\beta}, R^{13\alpha}, R^{13\beta}, R^{14\beta}$, and $R^{14\beta}$ preferably are as defined as in formula (XIII).

The dashed lines are optional π bonds.

$R^{8\beta}, R^9, R^{11\beta}, R^{12\beta}, R^{13\beta}$, and/or $R^{14\beta}$ are present only when $X^8, X^9, X^{11}, X^{12}, X^{13}$, and/or $X^{14}$, respectively, are saturated.

$R^{1\alpha}$ and $R^{2\alpha}$ preferably are independently a moiety which (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{1\alpha}$ and $R^{2\alpha}$ are independently selected from the group consisting of hydrogen; hydrocarbyl comprising from 1 to 6 carbon atoms; and —OR$^{118}$, wherein R$^{118}$ is hydrogen or hydrocarbyl containing from 1 to 6 carbon atoms, and particularly wherein R$^{118}$ is hydrogen or methyl. Most preferably, $R^{1\alpha}$ and $R^{2\alpha}$ are hydrogen.

$R^{3\alpha}$ preferably (a) comprises from 1 to 20 carbon atoms (more preferably from 1 to 6 carbon atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. In a more preferred embodiment, $R^{3\alpha}$ is hydrogen. In another more preferred embodiment, $R^{3\alpha}$ is selected from the group consisting of glycosidyl, acetylated glycosidyl, and malonylated glycosidyl. In an additional more preferred embodiment, $R^{3\alpha}$ is —OC(O)(R$^{119}$), wherein R$^{119}$ is benzyl or —N(CH$_2$CH$_2$Cl)$_2$. In yet another more preferred embodiment, $R^{3\alpha}$ comprises (a) no greater than 20 carbon atoms (more preferably, no greater than 6 carbon atoms); and (b) a moiety selected from the group consisting of amino, imino, oximido, oxy, phosphinidene, phosphino, phosphinyl, phosphinylidene, phosphono, phosphoranyl, phosphoranylidene, siloxy, silyl, silylene, sulfeno, sulfino, sulfo, and thio. In an even more preferred embodiment, $R^{3\alpha}$ comprises a polarizable hydrogen atom and is, for example, —C(O)(OH), —NH$_2$, =NH, =N(OH), —OH, =PH, —PH$_2$, —P(O)(H)(H), =P(O)(H), —P(O)(OH)(OH), —PH$_4$, =PH$_3$, =SiH$_2$, —S(OH), —S(O)(OH), S(O)(O)(OH), or —SH. In an alternative even more preferred embodiment, $R^{3\alpha}$ is —OR$^{120}$ or —OC(O)R$^{121}$, wherein R$^{120}$ and R$^{121}$ are hydrogen, halogen, or hydrocarbyl comprising from 1 to 19 carbon atoms (particularly 1 to 5 carbon atoms, and more particularly 1 to 2 carbon atoms). Most preferably, $R^{3\alpha}$ is —OH.

$R^{4\alpha}$ and $R^{5\alpha}$ preferably are independently a moiety which (a) comprises from 1 to 20 carbon atoms (more preferably from 1 to 6 atoms), and is selected from the group consisting of hydrocarbyl and substituted hydrocarbyl; or (b) does not comprise a carbon atom and is selected from the group consisting of amino, halogen, hydrogen, nitro, nitroso, oxy, phosphino, phosphinyl, phospho, phosphono, phosphoranyl, phosphoroso, siloxy, silyl, sulfeno, sulfino, sulfo, sulfonyl, and thio. More preferably, $R^{4\alpha}$ and $R^{5\alpha}$ are independently selected from the group consisting of hydrogen and hydrocarbyl comprising from 1 to 6 carbon atoms. Most preferably, $R^{4\alpha}$ and $R^{5\alpha}$ are hydrogen.

Examples of preferred compounds having the structure of formula (XIII) include the following estrogenic carboxylic acids (and pharmacuetically acceptable salts thereof):

1. 1-(p-Hydroxyphenyl)-6-ethyl-5-methylcyclohexene-4-carboxylic Acid

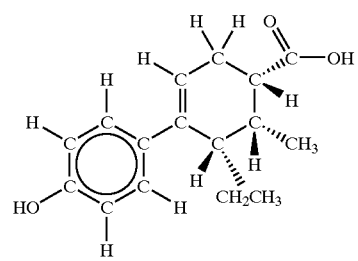

(XV)

2. 1-(p-Hydroxyphenyl)-2-ethyl-3-methylcyclohexene-4-carboxylic Acid

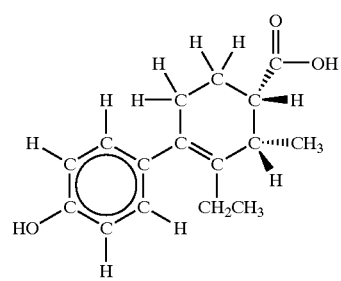

(XVI)

3. 1-(p-Hydroxyphenyl)-2-ethyl-3,5,5-trimethylcyclohexene-4-carboxylic Acid

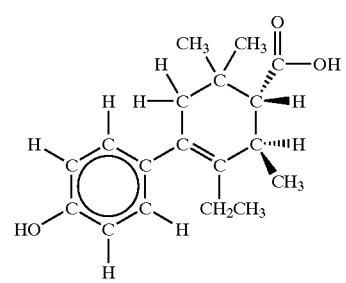

(XVII)

4. 4-(p-Hydroxyphenyl)-2,2,6,6-tetramethylcyclohexane Carboxylic Acid

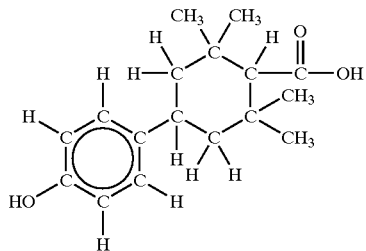

(XVIII)

5. 1-Phenyl-2-ethyl-3-methylcyclohexene-4-carboxylic Acid

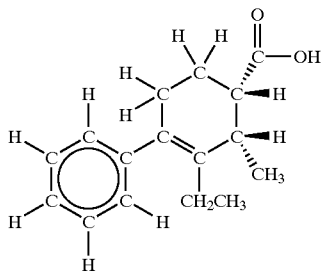

(XIX)

6. 1-Phenyl-5,6-dimethylcyclohexene-4-carboxylic Acid

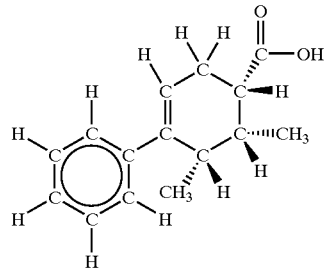

(XX)

For a review of the structures of estrogenic doisynolic-type acids, and methods for preparing these compounds, the reader is referred to the review of Meyers et al., "Doisynolic-Type Acids-Uterotropically Potent Estrogens Which Compete Poorly With Estradiol for Cytosolic Estradiol Receptors, *J. Steroid Biochem.* 31(4A):393–404 (1988), and the references cited therein.

B. Pharmaceutical Compositions

The compounds of the present invention can be formulated as pharmaceutical compositions. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., *Remington's Pharmaceutical Sciences*, Mack Publishing Co., Easton, Pa. (1975), and Liberman, H. A. and Lachman, L., Eds., *Pharmaceutical Dosage Forms*, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form will vary depending upon the patient and the particular mode of administration.

The mode of administration is partially dependent upon the chemical form of the estrogenic carboxylic acids. The phenolic and carboxylic salts (e.g., sodium, potassium, calcium, etc.) are more water soluble than the parent phenolic carboxylic acids, and can be administered orally or in aqueous solution. The estrogenic carboxylic acids themselves and their esters and related derivatives have lower water solubility and are probably best administered subcutaneously or transdermally in an oily or penetrating vehicle.

In the form of their 3-methyl ethers, (±)-Z-BDDA ("Fenocylin", Ciba-Geigy) and allenolic acid ("Vallestril", G.D. Searle and Co.) have been cleared for clinical use. However, Segaloff ((1949) in *Recent Progress in Hormone Research*, Vol. IV, G. Pincus, Ed., Academic Press, New York, pp. 85–111) discounted the clinical activity of Fenocylin in women. See Meyers C Y, Kolb V M, Gass G H, Rao B R, Roos C F, Dandliker W B: "Doisynolic-Type Acids— Uterotropically Potent Estrogens which Compete Poorly with Estradiol for Cytosolic Estradiol Receptors. *J Steroid Biochem* 31:393–404 (1988); and Soto A M, Meyers C Y, Sonnenschein C: "How Many Rings Can be Cleaved from a Steroidal Estrogen While Preserving its Estrogenic Activity? "*The Endocrine Society*, 70th Annual Meeting, Abstract (1988); and the foregoing discussion.

Certain of the pharmaceutical compounds of this invention which are administered in accordance with the methods of the invention can serve as prodrugs to other compounds of this invention. Prodrugs are drugs that can be chemically converted in vivo or in vitro by biological systems into an active derivative or derivatives. Prodrugs are administered in essentially the same fashion as the other pharmaceutical compounds of the invention. Non-limiting examples include non-hydroxylated phenylcyclohexenecarboxylic acids of this invention that are hydroxylated in vivo.

It should be noted that the present invention encompasses the use of estrogenic carboxylic acids as disclosed herein formulated alone, and in various combinations with one another. Single estrogenic carboxylic acids, or combinations of estrogenic carboxylic acids, can also be formulated in combination with other estrogens coventionally used in the art.

C. Dosages

Depending upon the particular pharmaceutical application, the estrogenically active compounds of the present invention can be administered daily to humans or animals in a number of different dosages. For example, as suggested by the results disclosed in Example 2, below, the dosage can be an amount in the range of from about 0.1 μg/kg/day to about 100 mg/kg/day, preferably from about 0.5 μg/kg/day to about 75 mg/kg/day, more preferably from about 1 μg/kg/day to about 50 mg/kg/day, even more preferably from about 1 μg/kg/day to about 25 mg/kg/day, and still more preferably from about 1 μg/kg/day to about 20 mg/kg/day. As suggested by the results disclosed in Example 4, below, dosages for use in treating prostatic (and other) disorders can be an amount in the range of from about 10 μg/kg/day to about 10 mg/kg/day, preferably from about 10 μg/kg/day to about 5 mg/kg/day, more preferably from about 10 μg/kg/day to about 2.5 mg/kg/day, and even more preferably from about 10 μg/kg/day to about 1 mg/kg/day. In further embodiments, the lower value of these dosage ranges can be as low as about 1 μg/kg/day.

The doses described above can be administered to a patient in a single dose or in proportionate multiple subdoses, for example two subdoses daily. In the case of proportionate multiple subdoses, dosage unit compositions can contain such amounts of submultiples thereof to make up the daily dose. Multiple doses per day can also increase the total daily dose should this be desired by the person prescribing the drug.

D. Treatment Regimen

The present invention provides methods for treating or preventing a variety of symptoms, conditions, and diseases that would benefit from estrogen therapy using the compounds disclosed herein. In this context, "treating" refers to ameliorating, suppressing, or eradicating these symptoms, conditions, and diseases. The regimen for treating a patient suffering from a symptom, condition, or disease that would benefit from estrogen therapy, or preventing the same, with the compounds and/or compositions of the present invention is selected in accordance with a variety of factors, including the age, weight, sex, diet, and medical condition of the patient, the severity of the infection, the route of administration, pharmacological considerations such as the activity, efficacy, pharmacokinetic, and toxicology profiles of the particular compounds employed, and whether a drug delivery system is utilized. It should be noted that the methods disclosed herein are applicable in both human and veterinary medicine. Treatment of domestic pets, such as cats and dogs, is contemplated in the present invention.

Administration of individual estrogenic carboxylic acids, combinations thereof, or such individual estrogenic carboxylic acids or combinations thereof in further combination with estrogens conventionally used in the art, should generally be continued over a period of several weeks to several months or years until symptoms reach acceptable levels, or have been eliminated entirely, indicating that the condition has been controlled or eradicated. As noted above, patients undergoing treatment with the drugs disclosed herein can be routinely monitored by measuring appropriate physical and physiological parameters to determine the effectiveness of therapy.

Continuous analysis of the data obtained by these methods permits modification of the treatment regimen during therapy so that optimal amounts of each compound are administered, and so that the duration of treatment can be determined as well. Thus, the treatment regimen/dosing schedule can be rationally modified over the course of therapy so that the lowest amount of each estrogenic carboxylic acid used alone or in combination which together exhibit satisfactory therapeutic effectiveness are administered, and so that administration of such compounds is continued only so long as is necessary to successfully treat the indicated condition.

In order to monitor the effect and progress of treatment, conventional assays can be used wherever appropriate. For example, the standard immunoassays for testosterone and prostate specific antigen (PSA) can be used in the case of prostate cancer. Significant decreases in either testosterone or PSA indicate the utility of the present compounds as therapeutic agents. When such assays are lacking or where effects are expected to be very slow, more subjective parameters can be employed. These are considered individually in the following examples discussing each disease.

The chronic effects of the Z-BDDA compounds as compared to those of E2 were studied in rats as a model mammalian system. In addition to anlysis of changes in body weight, additional metabolic and endocrine studies were performed, including monitoring food intake and metabolic and reproductive parameters in male and female rats. Because so little has been reported on the comparative effects of the Z-BDDA enantiomers, the (+)-, (−)-, and (±)-forms were prepared and investigated. Anner G, Miescher K: Hydrierungs—Und Umlagerungs-Reaktion in der Doisynolsäure—Reihe. Oestrogene Carbonsäuren XII. Hev. Chim. Acta 29 (1946)1889–1895; Die totalsyntheses von racemischen doisynolsäuren XXI. Über oestrogene carbonsäueren. ibid 30:1422–1432 (1947); Tschopp E: "Wirksamkeit, organconzentration und ausscheidung der 7-methyl-bisdehydro-doisynolsäure." *Helv Physiol Pharmacol Acta* 4:401–410 (1946); Tschopp E: "Die oestrogene wirkung der bisdehydrodoisynolsäure und ihre derivate." *Helv Physiol Pharmacol Acta* 4:271–284 (1946); Rometsch R, Miescher K: "Die spaltung des racemates der n-bisdehydro-doisynolsäure. Über östrogene carbonsäuren X." *Helv Chim Acta* 29:1231–1235 (1946); and Terenius L: "Differential Inhibition In Vitro of 17β-Estradiol Binding in the Mouse Uterus and Vagina by Optical Antipodes of Estrogen." *Molec Pharmac* 4:301–310 (1968).

VI. Definitions

The term "acyl" means the group having the formula —C(O)(R), wherein R is hydrocarbyl. The term "substituted acyl" means the group having the formula —C(O)(R), wherein R is, for example, substituted hydrocarbyl.

The term "alkanoyl halide" means the group having the formula —C(O)(R), wherein R is halogen.

The term "alkenyl" means a straight or branched hydrocarbyl comprising at least one carbon-carbon double bond, and includes, for example, ethenyl, propenyl, iso-propenyl, butenyl, isobutenyl, hexenyl, and the like.

The term "alkyl" means a saturated straight or branched chain hydrocarbyl (i.e., no double or triple carbon-carbon bonds), and includes, for example, methyl, ethyl, n-propyl, isopropyl, n-butyl, iso-butyl, sec-butyl, tert-butyl, pentyl, hexyl, and the like.

The term "alkynyl" means a straight or branched hydrocarbyl comprising at least one triple carbon-carbon bond, and includes, for example, ethynyl, propynyl, butynyl, isobutynyl, hexynyl, and the like.

The term "amide" means the group having the formula —C(O)(N($R^a$)($R^b$)), wherein $R^a$ and $R^b$ are independently, for example, hydrogen, hydrocarbyl, or substituted hydrocarbyl.

The term "amino" means the group having the formula —N($R^a$)($R^b$), wherein $R^a$ and $R^b$ are independently, for example, hydrogen, hydrocarbyl, or substituted hydrocarbyl.

The term "carboxyl" means the group having the formula —C(O)(OR), wherein R is, for example, hydrogen, hydrocarbyl, or substituted hydrocarbyl.

The term "formyl" means the group having the formula —C(H)(O).

The term "halogen" includes F, Cl, Br, and I.

The term "heterocyclyl" means a chain of 3 or more atoms (typically 5 or 6 atoms) forming a ring (or multiple rings), wherein at least one of the atoms forming the ring is an atom which is not a carbon atom or hydrogen atom (e.g., sulfur, nitrogen, or oxygen). The heterocyclyl may comprise all single bonds between the atoms forming the ring, or, alternatively, may comprise one or more double bonds between such atoms. Heterocyclyls include, for example, furyl, thienyl, pyridinyl, morpholinyl, and the like. In addition to being bound to the other atoms forming the ring, the atoms forming the ring of the heterocyclyl may also be bound to hydrogen or to another group, such as, for example: (a) a group which is selected from the group consisting of hydrocarbyl or a substituted hydrocarbyl (e.g., another heterocyclyl); or (b) a group which does not comprise a carbon atom and is selected from the group consisting of an amino, halogen, hydrogen, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfino, sulfinyl, sulfo, sulfonyl, thio, and thioxo.

The term "hydrocarbyl" means a group consisting exclusively of carbon and hydrogen atoms. Such a group may be straight, branched, cyclic (or multi-cyclic), or a combination thereof. It may also be saturated (i.e., comprise no carbon-carbon double or triple bonds) or unsaturated (i.e., comprise at least one carbon-carbon double or triple bond). Hydrocarbyls include, for example, alkyl, alkenyl, alkynyl, aryl, alkaryl, alkenaryl, and alkynaryl. The term "substituted hydrocarbyl" means a hydrocarbyl, wherein at least one hydrogen atom has been substituted with (a) an atom which is not a hydrogen or carbon atom (i.e., a heteroatom), or (b) a group of atoms comprising at least one heteroatom. A "heteroatom" may be, for example, a boron, halogen, nitrogen, oxygen, phosphorous, silicon, or sulfur atom. Substituted hydrocarbyls include hydrocarbyls wherein one or more hydrogen atoms have been substituted with, for example, amino, halogen, heterocyclyl, imino, nitro, nitroso, oximido, oxo, oxy, phosphinidene, phosphino, phosphinyl, phosphinylidene, phospho, phosphono, phosphoranyl, phosphoranylidene, phosphoroso, siloxy, silyl, silylene, sulfeno, sulfinyl, sulfino, sulfo, sulfonyl, thio, or thioxo. Examples of substituted hydrocarbyls include acyl (e.g., acetyl and benzoyl) and substituted acyl, alkanoyl halide, amide, formyl, nitrile, carboxyl, oxycarbonyl, alkoxy, amino substituted with hydrocarbyl (i.e., N($R^a$)($R^b$), wherein $R^a$ and $R^b$ are hydrocarbyl), phosphono substituted with hydrocarbyl (i.e., a phosphono ester, —P(O(O$R^a$)(O$R^b$), wherein $R^a$ and $R^b$ are hydrocarbyl), and sulfo substituted with hydrocarbyl (i.e., a sulfo ester, —S(O)(O)(OR), wherein R is hydrocarbyl).

The term "imino" means the group having the formula =NR, wherein R is, for example, hydrogen, hydrocarbyl, or substituted hydrocarbyl.

The term "nitrile" means the group having the formula —CN.

The term "nitro" means the group having the formula —NO$_2$.

The term "nitroso" means the group having the formula —NO.

The term "non-hydrocarbyl group" means a group that comprises no carbon atoms.

The term "oximido" means the group having the formula =N(OR), wherein R is, for example, hydrogen, hydrocarbyl, or substituted hydrocarbyl.

The term "oxo" means the oxygen group (i.e., =O) of a carbonyl group.

The term "oxy" means the group having the formula —OR, wherein R is, for example, hydrogen (i.e., —OR is hydroxy), hydrocarbyl, or substituted hydrocarbyl.

The term "oxycarbonyl" means the group having the formula —OC(O)(R), wherein R is, for example, hydrocarbyl or substituted hydrocarbyl.

The term "pharmaceutically acceptable salt" embraces salts commonly used to form alkali metal salts and to form addition salts of free acids or free bases. The nature of the salt is not critical, provided that it is pharmaceutically-acceptable. Suitable pharmaceutically-acceptable acid addition salts of the therapeutic compounds discussed herein may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclyl, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric and galacturonic acid. Suitable pharmaceutically-acceptable base addition salts of the therapeutic compounds discussed herein include metallic salts and organic salts. More preferred metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Preferred organic salts can be made from tertiary amines and quaternary ammonium salts, including in part, tromethamine, diethylamine, N,N'-dibenzylethylenediamine, chloroprocaine, choline, diethanolamine, ethylenediamine, meglumine (N-methylglucamine) and procaine. All of these salts may be prepared by conventional means from the corresponding therapeutic compounds discussed herein by reacting, for example, the appropriate acid or base with the compounds.

The term "phosphinidene" means the group having the formula $=PR$, wherein R is, for example, hydrogen, hydrocarbyl, or substituted hydrocarbyl.

The term "phosphino" means the group having the formula $—P(R^a)(R^b)$, wherein $R^a$ and $R^b$ are independently, for example, hydrogen, hydrocarbyl, or substituted hydrocarbyl.

The term "phosphinyl" means the group having the formula $—P(O)(R^a)(R^b)$, wherein $R^a$ and $R^b$ are independently, for example, hydrogen, hydrocarbyl, or substituted hydrocarbyl.

The term "phosphinylidene" means the group having the formula $=P(O)(R)$, wherein R is, for example, hydrogen, hydrocarbyl, or substituted hydrocarbyl.

The term "phospho" means the group having the formula $—PO_2$.

The term "phosphono" means the group having the formula $—P(O)(OR^a)(OR^b)$, wherein $R^a$ and $R^b$ are independently, for example, hydrogen, hydrocarbyl, or substituted hydrocarbyl.

The term "phosphoranyl" means the group having the formula $—P(R^a)(R^b)(R^c)(R^d)$, wherein $R^a$, $R^b$, $R^c$, and $R^d$ are independently, for example, hydrogen, hydrocarbyl, or substituted hydrocarbyl.

The term "phosphoranylidene" means the group having the formula $=P(R^a)(R^b)(R^c)$, wherein $R^a$, $R^b$, and $R^c$ are independently, for example, hydrogen, hydrocarbyl, or substituted hydrocarbyl.

The term "phosphoroso" means the group having the formula $—PO$.

The term "siloxy" means the group having the formula $—OSI(R^a)(R^b)(R^c)$, wherein $R^a$, $R^b$, and $R^c$ are independently, for example, hydrogen, hydrocarbyl, or substituted hydrocarbyl.

The term "silyl" means the group having the formula $—Si(R^a)(R^b)(R^c)$, wherein $R^a$, $R^b$, and $R^c$ are independently, for example, hydrogen, hydrocarbyl, or substituted hydrocarbyl.

The term "silylene" means the group having the formula $=Si(R^a)(R^b)$, wherein $R^a$ and $R^b$ are independently, for example, hydrogen, hydrocarbyl, or substituted hydrocarbyl. The term "unsubstituted silylene" means the group having the formula $=SiH_2$.

The term "sulfeno" means the group having the formula $—S(OR)$, wherein R is, for example, hydrocarbyl or substituted hydrocarbyl.

The term "sulfino" means the group having the formula $—S(O)(OH)$. The term "substituted sulfino" means the group having the formula $—S(O)(OR)$, wherein R is, for example, hydrocarbyl or substituted hydrocarbyl.

The term "sulfinyl" means the group having the formula $=SO$.

The term "sulfo" means the group having the formula $—S(O)(O)(OR)$, wherein R is, for example, hydrogen, hydrocarbyl, or substituted hydrocarbyl.

The term "sulfonyl" means the group having the formula $—S(O)(O)(R)$, wherein R is, for example, halogen, hydrocarbyl, substituted hydrocarbyl, or amine.

The term "thio" means the group having the formula $—SR$, wherein R is, for example, hydrogen, hydrocarbyl, or substituted hydrocarbyl.

The term "thioxo" means the group having the formula $=S$.

VII. EXAMPLES

The following non-limiting examples illustrate various aspects of the present invention.

Example 1

Preparation of (±)-(Z-bis Dehydrodoisynolic Acid ((±)-Z-BDDA))

(±)-Z-bisdehydrodoisynolic acid ((±)-Z-BDDA)) is prepared by refluxing a solution of Fenocylin in concentrated HBr-HOAc for 2.5 hr. After recrystallization, the melting point is 204–205.5° C. Elemental analysis, acid-base titration, and NMR can be used to confirm the identify of the product.

Alternatively, potassium hydroxide fusion of equilenin yields a mixture of acids from which the (−)-Z-bis-dehydrodoisynolic acid can be isolated (K. Miescher, *Chem. Rev.* 43:367–384 (1948)). One or more of the allenolic acids can be prepared by literature methods cited in Miescher. The other non-steroidal estrogenic compounds of the present invention, i.e., the hydroxyphenylcyclohexane- and -cyclohexene-, and hydroxytetrahydroanthracenecarboxylic acids disclosed herein, can be synthesized by methods disclosed in references discussed in Meyers et al., *J. Steroid Biochem.* 31 (4A):393–404 (1988).

Example 2

Comparative Effects of (−)-, (+)-, and (±)-Z-Bisdehydrodoisynolic Acids and Estradiol on Body Weight, Food Intake, Metabolic, and Reproductive Parameters in Male and Female Rats A study was designed to investigate the chronic effects of the Z-BDDA compounds vs. E2 in rats. In addition to analysis of changes in body weight, additional metabolic and endocrine studies were performed, including monitoring food intake and metabolic and reproductive parameters, in male and female rats. Moreover, because so little has been reported on the comparative effects of the Z-BDDA enantiomers, the (+), (−) and (±) forms were prepared and investigated.

The compounds used in these studies were (+)-17β-estradiol (E2), (−)-Z-bisdehydrodoisynolic acid [(−)-Z-BDDA], and (+)-Z-bisdehydrodoisynolic acid [(+)-Z-BDDA]. Their structures are shown below in a, b, and c, respectively. Racemic (±)-Z-bisdehydrodoisynolic acid [(±)-Z-BDDA] is a 1:1 mixture of the (+) and the (−) enantiomers.

a.

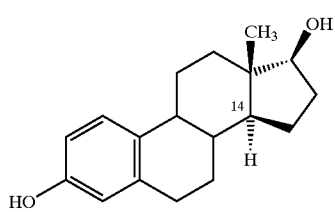

b.

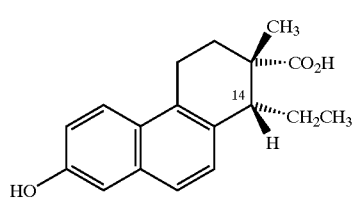

c.

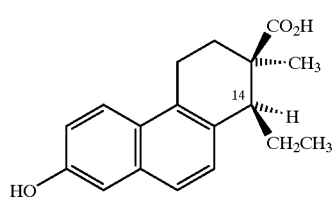

(+)-17β-Estradiol (E2) was purchased from Sigma Chemical Company (St. Louis, Mo.). (±)-Z-Bisdehydrodoisynolic acid [((±)-Z-BDDA] was prepared from (±)-Z-BDDA-3-OMe ("Fenocylin," from Ciba-Geigy, Inc.; m.p. 228–230° C.) as described by Meyers et al. (Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988); and Banz J, Winters T A, Hou Y, Adler S, Meyers C Y: "Activities of Non-Classical Estrogens: Effects of (−)-, (+)-, and (+)-Z-Bisdehydrodoisynolic Acids In Vitro and on Body Weight in Male and Female Rats." *The Endocrine Society*, 80th Annual Meeting, Abstract (1998)), m.p. (recrystallized from acetone-ligroin) 204–205.5° C. (darkens) 204° C. The slightly off-white crystals rapidly deepen in color in solution and more slowly in air. (+)-Z-BDDA and (−)-Z-BDDA were prepared by the resolution of (±)-Z-BDDA-3-OMe through their respective isolated and purified L-menthyl esters according to the method reported by Rometsch and Miescher. Rometsch R, Miescher K: "Die spaltung des racemates der n-bisdehydro-doisynolsäure. Über östrogene carbonsäuren X." *Helv Chim Acta* 29:1231–1235 (1946). The crystalline (+)- and (−)-Z-BDDA so prepared exhibited a single TLC spot, and their $^1$H- and $^{13}$C-NMR spectra correctly identified their structure.

Experiment 1

Twenty-five male and 25 female Sprague-Dawley rats, 9–10 weeks of age, were randomly assigned to groups of five animals, respectively, as a control group (no treatment) (C), for treatment with vehicle only (V), estradiol (E), (±)-Z-BDDA, or (+)-Z-BDDA. Each animal in group V received a daily 0.1 cc injection of a 10% ethanol-90% olive oil solution; the other treatments received their respective compound as a daily 0.1 cc injection, e.g., 2.5 μg of compound/g of body weight, in a 10% ethanol-90% olive oil solution. A temperature of 21° C. and an artificial 12-h light-dark cycle was maintained in the animal room. All animals were maintained on standard chow in powdered form for four weeks, then sacrificed after an overnight fast under i.p. pentobarbital anesthesia (50 mg/kg). Animal weight and food intake were measured weekly during the study, and the subsequent food-efficiency ratio [FER(g of weight change/g of food intake)] was determined. During sacrifice, blood was collected (via cardiac puncture) for cholesterol measurements. Immediately following sacrifice the fat pads and reproductive organs were removed and weighed.

Experiment 2

Twenty-five male and 25 female Wistar rats, 7–8 weeks of age, were randomly assigned to groups of five animals, respectively, for treatment with vehicle only (V), estradiol (E), (±)-Z-BDDA, (+)-Z-BDDA, or (−)-Z-BDDA. Each animal in group V received a daily 0.1 cc injection of a 10% ethanol-90% olive oil solution; the other treatments received their respective compound as a daily 0.1 cc injection, e.g., 2.5 μg of compound/g of body weight, in a 10% ethanol-90% olive oil solution. A temperature of 21° C. and an artificial 12-h light-dark cycle were maintained in the animal room. All animals were maintained on standard chow in powdered form, the males for five weeks and the females for six weeks, then sacrificed after an overnight fast under i.p. pentobarbital anesthesia (50 mg/kg). Animal weight and food intake were measured weekly during the study and subsequent FER values were determined. During sacrifice, blood was collected (via cardiac puncture) for glucose, luteinizing hormone, prolactin and testosterone measurements. The amounts of luteinizing hormone, prolactin and testosterone were measured to help elucidate the target tissue of the respective compounds in male and female rats. Immediately following sacrifice the fat pads and reproductive organs were removed and weighed.

Statistical Analyses

Experiments 1 and 2 employed a randomized design. All data were analyzed by one-way analysis of variance (ANOVA,)and post-hoc comparisons were made with Tukey pairwise comparisons test. Significance was confirmed at $p \leq 0.05$ (SYSTAT 7.0, SPSS INC., 1997), and all values are reported as means±standard error of the mean.

Results

E2 and the three forms of Z-BDDA produced both similar and distinct effects on reproductive parameters in male and female rats. For example, the results demonstrate that E2 and (+)- and (±)-Z-BDDA behave similarly in their effect on reproductive-organ weight: they promote an increase in uterine weight and a decrease in testis weight, compared to the control or vehicle alone (Table 1 and 2). Surprisingly, (−)-Z-BDDA did not induce an increase (p<0.05) in uterine weight as observed with (+), (±)-Z-BDDA and estradiol (FIG. 1) but, like them, (−)-Z-BDDA, compared to the vehicle alone, caused weight reduction (p<0.05) of the testis and prostate (Tables 1 and 2).

whereas in the male rats, all three Z-BDDA forms not only elicited estrogenic-like effects (Table 1 and 2), but appeared to be more potent with respect to weight repression (FIGS. 2 and 3). The male rats exhibited a reduction in visceral fat

TABLE 1

Experiment 1.
The effects of (+)- and (±)-Z-bisdehydrodoisynolic acid (Z-BDDA) and (+)-17β-estradiol on metabolic and reproductive parameters in male and female rats on treatment for 4 weeks*

| Treatment | Food intake (g) | FER (food efficiency ratio) | Cholesterol (mg/dl) | Visceral fat (g) | Uterus/testis weight (g) | Prostate weight (g) |
|---|---|---|---|---|---|---|
| Female | | | | | | |
| control | 300.0 ± 28.6 | 0.079 ± 0.010 | 91.6 ± 12.3 | 2.9 ± 0.3 | 0.42 ± 0.03 | — |
| vehicle[†] | 293.0 ± 26.1 | 0.040 ± 0.013 | 67.2 ± 12.5 | 1.6 ± 0.4[1] | 0.66 ± 0.06 | — |
| estradiol[¶] | 371.6 ± 17.8 | 0.035 ± 0.011 | 44.9 ± 15.8[1] | 0.8 ± 0.1[1] | 1.58 ± 0.15 | — |
| (±)-Z-BDDA[¶] | 318.2 ± 21.8 | −0.023 ± 0.027[1] | 30.1 ± 2.8[1] | 1.3 ± 0.1 | 2.04 ± 0.45[1] | — |
| (+)-Z-BDDA[¶] | 315.2 ± 18.4 | 0.045 ± 0.017[4] | 35.1 ± 8.6[1] | 2.1 ± 0.3[1,3] | 2.57 ± 0.79[1,2] | — |
| Male | | | | | | |
| control | 402.8 ± 25.0 | 0.134 ± 0.013 | 82.1 ± 6.1 | 5.4 ± 0.7 | 3.82 ± 0.19 | 0.64 ± 0.10 |
| vehicle[†] | 339.8 ± 22.6 | 0.087 ± 0.011 | 81.5 ± 3.9 | 8.2 ± 0.7[1] | 3.55 ± 0.11 | 0.56 ± 0.03 |
| estradiol[¶] | 298.2 ± 18.8[1] | −0.057 ± 0.012[1,2] | 51.5 ± 9.5[1,2] | 4.2 ± 0.4[2] | 0.94 ± 0.13[1,2] | 0.09 ± 0.01[1,2] |
| (±)-Z-BDDA[¶] | 344.6 ± 15.5 | −0.099 ± 0.009[1,2] | 36.2 ± 2.6[1,2] | 4.5 ± 0.4[2] | 0.72 ± 0.06[1,2] | 0.08 ± 0.02[1,2] |
| (+)-Z-BDDA[¶] | 326.0 ± 9.5[1] | −0.174 ± 0.027[1,2,3,4] | 24.6 ± 2.2[1,2,3] | 5.1 ± 0.2[2] | 0.84 ± 0.06[1,2] | 0.13 ± 0.04[1,2,3] |

*All values are the mean ± SEM, n = 5 animals/treatment (9–10 weeks of age).
[†]10% ethanol-90% olive oil solution.
[¶]Treatment groups received the compound (2.5 ug/g of body weight) in 10% ethanol-90% olive oil solution.
[1]significantly different from control ($p < 0.05$); [2]significantly different from vehicle ($p < 0.05$); [3]significantly different from estradiol ($p < 0.05$); [4]significantly different from (±)-Z-BDDA ($p < 0.05$).

TABLE 2

Experiment 2.
The effects of (−)-, (+)-, and (±)-Z-bisdehydrodoisynolic acids (Z-BDDA) and (+)-17β-estradiol on metabolic and reproductive parameters in male and female rats on treatment for 5–6 weeks*

| Treatment | Food intake (g) | FER (food efficiency ratio) | Blood glucose (mg/dl) | Uterus/testis weight (g) | Prostate weight (g) |
|---|---|---|---|---|---|
| Female | | | | | |
| vehicle[†] | 625.8 ± 49.3 | 0.071 ± 0.007 | 107.00 ± 11.47 | 1.22 ± 0.21 | — |
| estradiol[¶] | 699.6 ± 33.7 | 0.039 ± 0.004 | 100.80 ± 10.22 | 4.83 ± 1.30[1] | — |
| (±)-Z-BDDA[¶] | 704.0 ± 51.7 | 0.017 ± 0.003[1,2] | 80.40 ± 5.66 | 4.25 ± 1.04[1] | — |
| (+)-Z-BDDA[¶] | 693.6 ± 72.3 | 0.026 ± 0.008[1] | 89.60 ± 6.15 | 4.02 ± 0.91[1] | — |
| (−)-Z-BDDA[¶] | 675.2 ± 37.9 | 0.011 ± 0.005[1,2] | 95.00 ± 8.33 | 1.44 ± 0.34[2,3,4] | — |
| Male | | | | | |
| vehicle[†] | 525.8 ± 27.3 | 0.12 ± 0.02 | 134.80 ± 10.97 | 2.68 ± 0.26 | 0.25 ± 0.11 |
| estradiol[¶] | 590.4 ± 47.7 | 0.00 ± 0.01[1] | 108.00 ± 10.90 | 0.74 ± 0.04[1] | 0.06 ± 0.02 |
| (±)-Z-BDDA[¶] | 530.0 ± 33.0 | −0.04 ± 0.01[1,2] | 98.60 ± 14.00 | 0.78 ± 0.02[1] | 0.16 ± 0.02 |
| (+)-Z-BDDA[¶] | 676.0 ± 33.2 | −0.02 ± 0.01[1] | 94.00 ± 10.18[1] | 0.61 ± 0.02[1] | 0.02 ± 0.00[1] |
| (−)-Z-BDDA[¶] | 650.0 ± 54.3 | −0.01 ± 0.01[1] | 88.00 ± 2.00[1] | 0.57 ± 0.04[1] | 0.03 ± 0.10[1] |

*All values are the mean ± SEM, n = 5 animals/treatment (9–10 weeks of age).
[†]10% ethanol-90% olive oil solution.
[¶]Treatment groups received the compound (2.5 ug/g of body weight) in 10% ethanol-90% olive oil solution.
[1]significantly different from vehicle ($p < 0.05$); [2]significantly different from estradiol ($p < 0.05$); [3]significantly different from (±)-Z-BDDA ($p < 0.05$); [4]significantly different from (+)-Z-BDDA ($p < 0.05$).

Parallel to their effects on reproductive parameters, E2 and the three forms of Z-BDDA also elicited similar and distinct effects on metabolic parameters in the male and female rats. For example, in the female rats in both experiments, (−)- and (±)-Z-BDDA appeared to repress weight gain slightly more than did (+)-Z-BDDA and E2, while in the male rats estradiol and the three Z-BDDA forms caused a dramatic reduction in body weight (FIGS. 2 and 3).

Surprisingly, the specific enantiomers of Z-BDDA appeared to elicit a divergence between estrogenicity and weight repression in the female rats (FIGS. 1, 2, and 3), weight when treated with E2 and each of the three Z-BDDA forms, respectively, versus vehicle (Table 1). It is apparent from other metabolic parameters (i.e., food intake and FER) that the weight repression in weight-gain and even the weight reduction were independent of food intake (Table 1 and 2). In fact, almost all of the difference in weight can be accounted for by a decrease in food efficiency (Table 1 and 2).

In addition to the gross physiological parameters, metabolic processes were also examined. The female rats receiving (+)-Z-BDDA, (±)-Z-BDDA, or E2 exhibited a decrease in total cholesterol versus control (Table 1). The males exhibited a more pronounced cholesterol-lowering pattern (p<0.05), (+)-Z-BDDA having the most profound effect (Table 1). Furthermore, in the second experiment, male rats receiving either (−)- or (+)-Z-BDDA compounds exhibited a reduction (p<0.05) in blood glucose, while the (±)-Z-BDDA treated males and the females treated with all the Z-BDDA compounds demonstrated a trend (p=0.06) toward a reduction in blood glucose (Table 2).

In the same experiment, luteinizing hormone, prolactin, and testosterone were measured to detect possible endocrine disruption caused by the Z-BDDA compounds. No significant changes in luteinizing hormone and prolactin were observed. However, compared to the vehicle, (+)-Z-BDDA as well as E2 caused a significant (p<0.05) testosterone suppression in the male rats, a trend which was less pronounced with (−)- and (±)-Z-BDDA.

Conclusions

These results with the Z-BDDA compounds demonstrate that specific enantiomers of Z-BDDA appear to confer cardioprotective benefits (i.e., reduction in cholesterol, body weight, blood glucose, and positive alterations in distribution of visceral fat). Wilson P W: "The Impact of Estrogen on Cardiovascular Disease." Perspective Studies: The Framingham Study. Postgrad Med 51–53:89–90 (1989); Cooper R L, Kavlock R J: "Endocrine Disruptors and Reproductive Development: A Weight-of-Evidence Overview." J Endocrinol 152:159–166 (1997); and Reubinoff B E, Wurtman J, Rojansky N, Adler D, Stein P, Schenker J G, Brzezinski A: "Effects of Hormone Replacement Therapy on Weight, Body Composition, Fat Distribution, and Food Intake in Early Postmenopausal Women: A Prospective Study." Fertil Steril 64:963–968 (1995). The (−) enantiomer appears to minimize undesirable estrogenic effects on reproductive tissues. The Z-BDDA compounds exhibited a cholesterol-lowering effect consistent with that elicited by other estrogenic compounds. See Heer J, Billeter J R, Miescher K: "Totalsynthese der racemischen bisdehydro-doisynolsäure. Über oestrogene carbosäuren IV." Helv. Chim. Acta 28:1342–1354 (1945); Ke H Z, Chen H A, Simmons H A, Qi H, Crawford D T, Pirie C M, Chidsey-Frink K L, Ma Y F, Jee W S S, Thompson D D: "Comparative Effects of Droloxifene, Tamoxifen, and Estrogen on Bone, Serum Cholesterol, and Uterine Histology in the Ovariectomized Rat Model." Bone 20:31–39 (1997); Sato M, Rippy M K, Bryant H U: "Raloxifene, Tamoxifen, Nafoxidine, or Estrogen Effects on Reproductive and Nonreproductive Tissues in Ovariectomized Rats." FASEB J 10:905–912 (1996); Dodge J A, Glasebrook A L, Magee D A, Phillips D L, Sato M, Short L L, Bryant HU: "Environmental Estrogens: Effects on Cholesterol Lowering and Bone in the Ovariectomized Rat." J Steroid Biochem Molec Biol 59:155–161 (1996); and Hart J E: "Endocrine Pathology of Estrogens: Species Differences." Pharmac Ther 47:203–218 (1990). Surprisingly, the hypocholesterolemic, weight-repressing, and visceral fat-reducing effects were demonstrated in reproductively intact male and female rats. This effect may be unique among non-steroidal estrogens. For example, raloxifene has no significant clinical effects in healthy, menstruating women. Heywood R, Wadsworth PF: "The Experimental Toxicology of Estrogens." Pharmac Ther 8:125–142 (1980). While raloxifene as well as tamoxifen and nafoxidine seem to elicit a cholesterol-lowering and a minimal weight-repressing effect in ovariectomized animals, the Z-BDDA compounds appear to be much more effective and, moreover, produce this effect in reproductively intact animals. Meyers C Y, Lutfi H G, Adler S: "Transcriptional Regulation of Estrogen-Responsive Genes by Non-Steroidal Estrogens: Doisynolic and Allenolic acids." J Steroid Biochem Molec Biol 62:477–489 (1997); Heer J, Billeter J R, Miescher K: "Totalsynthese der racemischen bisdehydro-doisynolsäure. Über oestrogene carbos äuren IV." Helv. Chim. Acta 28:1342–1354 (1945); Ke H Z, Chen H A, Simmons H A, Qi H, Crawford D T, Pirie C M, Chidsey-Frink K L, Ma Y F, Jee W S S, Thompson D D: "Comparative Effects of Droloxifene, Tamoxifen, and Estrogen on Bone, Serum Cholesterol, and Uterine Histology in the Ovariectomized Rat Model." Bone 20:31–39 (1997); Sato M, Rippy M K, Bryant H U: "Raloxifene, Tamoxifen, Nafoxidine, or Estrogen Effects on Reproductive and Nonreproductive Tissues in Ovariectomized Rats." FASEB J 10:905–912 (1996); and Heywood R, Wadsworth P F: "The Experimental Toxicology of Estrogens." Pharmac Ther 8:125–142 (1980). Being observed in intact, non-castrate male and female animals, these effects suggest clinical applications for these or similar compounds in treating pre- as well as post-menopausal women, and males at risk for cardiovascular and prostatic disease.

The distinct effects elicited by all three Z-BDDA forms on body weight, food intake, FER, and visceral fat appear to be compound-specific and somewhat divergent from the effects elicited by E2. It is apparent from the food intake and FER data that the repression in body-weight gain was independent of the quantity of food consumed. The fact that almost all of the variation in weight can be accounted for by a decrease in food efficiency points to a metabolic alteration elicited by the Z-BDDA compounds rather than appetite suppression as the weight-repressing mechanism. This finding is in contrast to the effects of other estrogenic compounds on body weight. While some other estrogens may cause weight repression, in those cases it appears to be compound-, species-, and gender-specific and, in sharp contrast to the results obtained with the present BDDA compounds, can be explained by a reduction in food intake. In further contrast to the present results with the BDDA compounds, these effects elicited by other estrogens are reported in studies with castrated rather than reproductively intact animals. See Heer J, Billeter J R, Miescher K: "Totalsynthese der racemischen bisdehydro-doisynolsäure. Über oestrogene carbosäuren IV." Helv. Chim. Acta 28:1342–1354 (1945); Ke H Z, Chen H A, Simmons H A, Qi H, Crawford D T, Pirie C M, Chidsey-Frink K L, Ma Y F, Jee W S S, Thompson D D: "Comparative Effects of Droloxifene, Tamoxifen, and Estrogen on Bone, Serum Cholesterol, and Uterine Histology in the Ovariectomized Rat Model." Bone 20:31–39 (1997); Sato M, Rippy M K, Bryant H U: "Raloxifene, Tamoxifen, Nafoxidine, or Estrogen Effects on Reproductive and Nonreproductive Tissues in Ovariectomized Rats." FASEB J 10:905–912 (1996); Dodge J A, Glasebrook A L, Magee D A, Phillips D L, Sato M, Short L L, Bryant H U: "Environmental Estrogens: Effects on Cholesterol Lowering and Bone in the Ovariectomized Rat." J Steroid Biochem Molec Biol 59:155–161 (1996); and Hart J E: "Endocrine Pathology of Estrogens: Species Differences." Pharmac Ther 47:203–218 (1990).

These results also suggest that (−)-Z-BDDA appears to exhibit both estrogenic and anti-estrogenic activities in female rats. This was not the case for the males, and may be dependent on the interaction of (−)-Z-BDDA with endogenous E2. Racemic Z-BDDA and its two enantiomers, while all promoting weight-repressing effects in female rats, differed in their capacity to elicit uterotropism, a classic assay for estrogenic activity. Surprisingly, (−)-Z-BDDA did not induce the significant increases in uterine weight observed with (+)- or (±)-Z-BDDA or E2. In contrast to the results observed in the chronic treatment study, it has previously been demonstrated that the (−) enantiomer of (±)-Z-BDDA is the enantiomer responsible for the high uterotropic activity observed when administered acutely. Anner G, Miescher K: Hydrierungs—Und Umlagerungs-Reaktion in der Doisynolsäure—Reihe. Oestrogene Carbonsäuren XII. *Helv. Chim. Acta* 29 (1946) 1889–1895; Die totalsyntheses von racemischen doisynolsäuren XXI. Über oestrogene carbonsäueren. ibid 30:1422–1432 (1947); Tschopp E: "Wirksamkeit, organconzentration und ausscheidung der 7-methyl-bisdehydro-doisynolsäure." *Helv Physiol Pharmacol Acta* 4:401–410 (1946); Tschopp E: "Die oestrogene wirkung der bisdehydrodoisynolsäure und ihre derivate." *Helv Physiol Pharmacol Acta* 4:271–284 (1946); Rometsch R, Miescher K: "Die spaltung des racemates der n-bisdehydro-doisynolsäure. Über ostrogene carbonsäuren X." *Helv Chim Acda* 29:1231–1235 (1946); and Terenius L: "Differential Inhibition In Vitro of 17β-Estradiol Binding in the Mouse Uterus and Vagina by Optical Antipodes of Estrogen." *Molec Pharmac* 4:301–310 (1968). The basis of the difference between the results presented herein and those reported previously is not known. However, in addition to differences in duration of treatment, other factors that may have contributed to the lack of uterotropism elicited by (−)-Z-BDDA in the present studies include the dosages used and the species and ages of the animals.

Of further interest are the differences observed in the potency of the Z-BDDA compounds when the in vivo results are compared with either cell-culture assays measuring activation of estrogen receptor, or with in vitro assays of relative receptor-binding affinity. Numerous competitive binding-inhibition studies with the classical estrogen receptors (ER$^\alpha$) have demonstrated that the binding affinity of (±)-Z-BDDA is much lower than that of estradiol. Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988); Soto A M, Meyers C Y, Sonnenschein C: "How Many rings Can be Cleaved from a Steroidal Estrogen While Preserving its Estrogenic Activity? *The Endocrine Society*, 70*th Annual Meeting*, Abstract (1988); and Banz J, Winters T A, Hou Y, Adler S, Meyers C Y: "Activities of Non-Classical Estrogens: Effects of (−)-, (+)-, and (±)-Z-Bisdehydroisynolic Acids In Vitro and on Body Weight in Male and Female Rats." *The Endocrine Society*, 80*th Annual Meeting*, Abstract (1998). These results were substantiated recently by direct binding studies using preparations of human ERα, and are in agreement with previous results with (−)-Z-BDDA, which were determined with mouse uterine tissue in competitive binding-inhibition studies. Terenius L: "Differential Inhibition In Vitro of 17β-Estradiol Binding in the Mouse Uterus and Vagina by Optical Antipodes of Estrogen." *Molec Pharmac* 4:301–310 (1968); and Meyers C Y, Lutfi H G, Adler S: "Transcriptional Regulation of Estrogen-Responsive Genes by Non-Steroidal Estrogens: Doisynolic and Allenolic acids." *J Steroid Biochem Molec Biol* 62:477–489 (1997). Hence, there is an apparent activity/binding paradox, suggesting that the classic estrogen receptor, ERα, may not be the exclusive receptor or pathway mediating the actions of Z-BDDA compounds, or possibly even those of estradiol. Meyers C Y, Kolb V M, Gass G H, Rao B R, Roos C F, Dandliker W B: "Doisynolic-Type Acids—Uterotropically Potent Estrogens which Compete Poorly with Estradiol for Cytosolic Estradiol Receptors. *J Steroid Biochem* 31:393–404 (1988).

Recently, a new form of estrogen receptor, ERβ, has been identified, and its role in estrogenic regulation in various target tissues and its affinity for non-steroidal ligands are currently being defined. Kuiper G G, Carlsson B, Grandien K, Enmark E, Haggblad J, Nilsson S, Gustafsson J: "Comparison of the Ligand Binding Specificity and Transcript Tissue Distribution of Estrogen Receptors α and β." *Endocrinology* 138:863–870 (1997); and Pace P, Taylor J, Suntharaiingam S, Coombes R C, Ali S: "Human Estrogen Receptor β Binds DNA in a Manner Similar to and Dimerizes with Estrogen Receptor α." *J Biol Chem* 272:25832–25838 (1997). Initial studies comparing the classical ER$^\alpha$ and the novel estrogen receptor ERβ show very similar results. The binding affinity of (+)-Z-BDDA is even lower than that of the (−) enantiomer, and both enantiomers have a much lower affinity for estrogen receptors than does estradiol, whether measured via direct receptor binding assays or by generating dose-response profiles using activation of estrogen-responsive reporter genes in cell-culture systems. Banz J, Winters T A, Hou Y, Adler S, Meyers C Y: "Activities of Non-Classical Estrogens: Effects of (−)-, (+)-, and (±)-Z-Bisdehydrodoisynolic Acids In Vitro and on Body Weight in Male and Female Rats." *The Endocrine Society*, 80*th Annual Meeting*, Abstract (1998). The evaluation of ERβ has not resolved the apparent paradox. However, the use of heterodimers of ERα and ERβ has not been evaluated, and may add a further degree of complexity to this binding/ activity evaluation.

Alternatively, there is evidence that in vivo, serum-binding proteins could account for part of the activity/ binding paradox emanating from a comparison of estradiol on one hand and the three Z-BDDA forms on the other. Danzo B J: "Environmental Xenobiotics May Disrupt Normal Endocrine Function by Interfering with the Binding of Physiological Ligands to Steroid Receptors and Binding Proteins." *Environ Health Perspect* 105:294–301 (1997); and Nagel S C, vom Saal F S, Thayer K A, Dhar M G, Boechler M, Welshons W V: "Relative Binding Affinity-Serum Modified Access Assay Predicts the Relative In Vivo Bioactivity of the Xenoestrogens Bisphenol A and Octylphenol." *Environ Health Perspect* 105:70–76 (1997). Steroid-hormone binding globulin (SHBG) and serum albumin appear to have a much higher affinity for estradiol than for many environmental and synthetic estrogens. Thus, in vivo, there is a relatively higher level of free versus bound compound compared to estradiol than would be predicted from in vitro binding studies alone. In addition, nonsteroidal environ-mental and synthetic estrogens may also elicit biological effects independent of the ligand-estrogen receptor complex (i.e., antioxidant and enzyme modulation). Wehling M: "Specific, Nongenomic Actions of Steroid Hormones." *Annu Rev Physiol* 59:365–393 (1997); Akiyama T, Ishida J, Nakagawa S, Ogawara H, Watanabe S, Itoh N, Shibuya M, Fukami Y: "Genistein, A Specific Inhibitor of Tyrosine-Specific Protein Kinases." *J Biol Chem* 262:5592–5595 (1987); Peterson G, Barnes S: "Genistein Inhibits Both Estrogen and Growth Factor-Stimulated Proliferation of Human Breast Cancer Cells. *Cell Growth & Differentiation* 7:1345–1351 (1996); Spink D C, Johnson J A, Connor S P, Aldous K M, Gierthy J F: "Stimulation of 17 Beta-Estradiol Metabolism in MCF-7 Cells by Bromochloro- and Chloromethyl-Substituted Dibenzo-p-dioxins and Dibenzo-furans: Correlations with Antiestrogenic Activity." *Journal of Toxicology & Environmental Health* 41:451–466 (1994); Behl C, Skutella T, LeZoualch F, Post A, Widmann M, Newton C J, Holsboer F: "Neuroprotection Against Oxidative Stress by Estrogens: Structure-Activity Relationship."

Mol Pharmacol 51:535–541 (1997); Wiseman H, O'Reilly J: "Oestrogens as Antioxidant Cardioprotectants." *Biochemical Society Transactions* 25:54–59 (1997); and Smith C L, Conneely O M, O'Malley B W: "Modulation of the Ligand-Independent Activation of the Human Estrogen Receptor by Hormone and Antihormone." *Proc Natl Acad Sci* 90:6120–6124 (1993). The final in vivo effect of these compounds may reflect all of these contributions.

The foregoing data, generated in intact, non-castrated male and female animals, indicate that the observed effects, unlike those reported in comparable studies with tamoxifen, nafoxidine, or raloxifene, are not obscured by endogenous estradiol. Heer J, Billeter J R, Miescher K: "Totalsynthese der racemischen bisdehydro-doisynolsäure. Über oestrogene carbosäuren IV." *Helv. Chim. Acta* 28:1342–1354 (1945); Ke H Z, Chen H A, Simmons H A, Qi H, Crawford D T, Pirie C M, Chidsey-Frink K L, Ma Y F, Jee W S S, Thompson D D: "Comparative Effects of Droloxifene, Tamoxifen, and Estrogen on Bone, Serum Cholesterol, and Uterine Histology in the Ovariectomized Rat Model." *Bone* 20:31–39 (1997); Sato M, Rippy M K, Bryant H U: "Raloxifene, Tamoxifen, Nafoxidine, or Estrogen Effects on Reproductive and Nonreproductive Tissues in Ovariectomized Rats." *FASEB J* 10:905–912 (1996); and Heywood R, Wadsworth P F: "The Experimental Toxicology of Estrogens." *Pharmac Ther* 8:125–142 (1980). The Z-BDDA compounds cause weight repression/reduction in male and female rats via an unknown mechanism. The results demonstrate remarkable selective estrogen receptor modulator (SERM) activity, and strongly suggest clinical applications for these compounds in peri- as well as post-menopausal women. Furthermore, they suggest clinical applications for these compounds (or appropriate derivatives thereof) in males at risk for cardiovascular and prostatic disease.

Example 3

Effects of Z-Bisdehydrodoisynolic Acids on In situ Apoptosis in Primary Porcine Granulosa Cells Estrogens have been found to decrease ovarian follicle atresia (Tilly et al. (1991) *Endocrinology* 129:2799–2801) which in turn could increase the number of follicles recruited and thus ovulated each menstrual or estrous cycle in humans and animals, respectively. Apoptosis, or programmed cell death, is the underlying mechanism for follicular atresia. This experiment was performed to determine if BDDAs affect follicular cell apoptosis.

Materials and Methods
Tissue Culture

Porcine ovaries were obtained from local packing plants and transported to the laboratory on ice-cold Hank's balanced salt solution (HBSS). Each of the follicles was aspirated with an insulin syringe, and the follicular fluid was centrifuged at 3000 rpm and 4° C. for 15 min. The supernatant was poured off and the cells were washed in 5 mls of cold HBSS and centrifuged for another 10 min. The cells were again resuspended in HBSS, and the number of viable cells counted under the microscope using a hematocytometer. Once the number of cells was determined, the cells were centrifuged again for 10 min. and resuspended in the appropriate volume of Eagle's minimum essential media (MEM) containing 10% fetal bovine serum (FBS) and antibiotic/antimycotics. The cells were plated at 250,000 per well in 8 chamber microscope slides (Nunc, Naperville, Ill.) which were pre-treated with poly-L-lysine for 10 min. The slides were incubated at 5% $CO_2$/95% air at 37° C. Approximately 12 hours later, the medium was removed by vacuum and replaced with pre-warmed, serum-free MEM. Cells were then treated for 2–3 hrs with MEM only to wash out any estrogen effects from the serum (Winters et al. (1994) *Biol. Reprod.* 50 (Suppl. 1):113; Suttner et al. (1998) *Biol. Reprod.* 59 (Suppl.): (Accepted for publication).

Treatments

Following serum-free MEM treatment, cells were treated for 24 hr with (+) or (−) enantiomers of Z-BDDA or estradiol at 0. 1, 1, and 10 μM, or EtOH vehicle control in serum-free MEM.

Apoptosis Assay

Cells were subsequently processed using an in situ apoptosis assay kit (Apotag-Plus In Situ Apoptosis Kit-Peroxidase, Edition 1.1., Oncor, Gaithersburg, Md., 1995) to study ovarian apoptosis (Suttner et al., 1998). The slides were washed in two changes of PBS for 5 min each, and then quenched in 2% hydrogen peroxide in methanol for 5 min. at room temperature. After pre-treatment with an equilibration buffer, 13 ul of Terminal deoxynucleotidyl Transferase (TdT) diluted with reaction buffer and distilled water were added, and the slides were incubated for 1 h at 37° C. in a humidified chamber. After this 1 h period, the slides were put in pre-warmed stop wash buffer in the incubator for 30 min to stop the reaction. Next, the slides were washed in three changes of PBS for 5 min. each, and the anti-digoxigenin peroxidase was placed on the slides for 30 min. in a humidified chamber at room temperature. Once this time was up, the slides were washed in four changes of PBS for 5 min. each and stained with diaminobenzidine substrate solution for 15–20 min. This yielded a brown stain in apoptotic cells. After washing in three changes of distilled water for 1 min., followed by a 5 min. wash, the slides were counterstained in methyl green for 8 min. This yielded a blue/green stain in non-apoptotic cells. Once counterstained, the specimens were washed in three changes of distilled water and 100% butanol, respectively, by dipping 10 times in the first and second washes, followed by 30 sec. in the third wash. The slides were cleared in three washes of xylene for 2 min. each and then mounted under coverslips with permount.

Image Analysis

The degree of apoptosis for the calorimetric apoptosis assay was quantified microscopically using an image analysis system (Optimas 5.23, Optimas Users Guide, 5th Edition, Redmond, Wash.). Ten measurements (captured images) were taken for each concentration based on a pre-determined grid. Brown and blue/green color thresholds for apoptotic and non-apoptotic cells, respectively, were set for each captured image. Percentage area of each color was then quantitated using the image analysis system. Data were then transferred to a spreadsheet (Excel, Microsoft Corp., Redmond, Wash.) for sorting before statistical analysis. This procedure was repeated for each slide and each concentration in duplicate.

Statistics

Statistical analysis was performed using a statistical program (SAS, 1988, SAS/STAT User's Guide. Statistical Analysis Institute, Cary, N.C.). Contrast analyses were run for the weekly experiments, and all of the treatments were compared. The level of significance was determined at $p<0.05$.

Results (−)-Z-BDDA treatment decreased ($P<0.01$) mean apoptosis (% area) from 63.4% in the controls to 26.1% in treated cells. (+)-Z-BDDA treatment did not appreciably change mean apoptosis in the controls (68.4%) vs. the treated cells (61.1%). Estradiol treatment combined was not different from controls; however, percent apoptosis was lower (P<0.05) at 10 μM estradiol (23.8%). In addition, (−)-Z-BDDA tended to decrease (P=0.06) percent apoptosis vs. estradiol (46.5).

Conclusions

These results indicate that (−)-Z-BDDA has the ability to decrease apoptosis in granulosa cells from the ovarian follicle of a porcine experimental model. Decreased follicle apoptosis could lead to more follicle recruitment and ovulations in the mammalian ovary. The inhibition of granulosa cell apoptosis by (−)-Z-BDDA appears to be more substantial than that of estradiol. The (+)-enantiomer did not appear to have an effect in these experiments. However, (+)-Z-BDDA could be active at a higher concentration, or be acting as an antiestrogen inhibiting the estrogenic effect seen with (−)-Z-BDDA and estradiol. These results suggest that the use of (−)-Z-BDDA in human and/or veterinary medicine could lead to more follicle recruitment and ovulations, thus increasing fertility. (+)Z-BDDA may may have applications as a birth control drug. In addition, the BDDAs could potentially be used to modulate other physiological processes controlled by apoptosis, including maturation of the immune system, embryonic development, luteolysis, male pattern baldness, cancer, tissues responding to thermal and metabolic stress, tissues responding to hormonal stimuli (especially estrogens), and normal tissue turnover (Bowen et al. (1990) *Programmed Cell Death in Tumors and Tissues*, Chapman & Hall, New York, N.Y.).

Example 4

Differential Effects of Estrogenic Carboxylic Acids on the Prostate and Testis of Male Rats Estrogens have been used in the treatment of prostate cancer; however, these estrogens have negative feminizing side effects. These include shrinkage of the testis and accessory glands (including the prostate), gynecomastia, salt and water retention, and inhibition of other secondary male sex characteristics (including loss of libido and impotence). Gudziak, M R, and A Y Smith. "Hormonal Therapy for Stage D Cancer of the Prostate" *West J Med* 160:351–359 (1994). In addition, estrogen therapy in males leads to a three-fold increased risk of thromboembolic events (including heart attacks, strokes, and blood clots). Glashan, R W, and M R G Robinson. "Cardiovascular Complications in the Treatment of Prostatic Carcinoma." *Br J Urol* 53:624–627 (1981). Since estrogen treatment in males causes these undesirable effects, estrogens are only used in severe prostate carcinoma, and are not usually used in other prostatic conditions such as benign prostate hypertrophy. Jacobi, G H. "Hormonal Treatment of Metastatic Carcinoma." In: *The Prostate*, pp. 119–128.(J M Fitzpatrick and R J Krane, eds., Churchill Livingstone, New York, N.Y. 1989); de Klerk, D P, and F Allen. "Medical Therapy for Benign Prostatic Hyperplasia." In: *The Prostate*, pp. 119–128 (J M Fitzpatrick and R J Krane, eds., Churchill Livingstone, New York, N.Y. 1989).

This study was undertaken to determine the effects that enantiomers of the estrogenic carboxylic acids, Z-bisdehydrodoisynolic acids (BDDA) and hydroxyallenolic acids (HAA), have on the prostate, testis, and other physiological parameters in male rats. As reported below, the results demonstrate that these compounds possess utility as a therapy for prostatic disease, as well as in other clinical applications in males.

Materials and Methods

Sixty male Sprague-Dawley rats, 7–8 weeks of age, were randomly assigned to groups of ten animals. Each group was randomly assigned to one of six treatments: Vehicle control (C), Estradiol-17β(E), (−)-Z-BDDA, (+)-Z-BDDA, (−)-HAA, and (+)-HAA. The compounds were all administered at a dose of 0.1 μg/g of body weight in 0.1 cc once a day for 6 weeks. The estrogenic compounds were dissolved in 10% ethanol and 90% olive oil vehicle. A temperature of 21° C. and an artificial 12 h light-dark cycle were maintained in the animal room. All animals were maintained on standard chow in powdered form for six weeks, and then sacrificed after an overnight fast under i.p. pentobarbitol anesthesia (50 mg/kg). Animal weight was measured weekly during the study. During sacrifice, blood was collected via cardiac puncture. Immediately following sacrifice, the fat pads, livers, pituitaries, testes, seminal vesicles, and prostate were removed and weighed, and snap frozen in liquid nitrogen. Prostates and one testis from 2–3 animals in each treatment group were fixed in 10% formalin for histological examination. These tissues were fixed overnight, blocked in paraffin, sectioned at 4 μm, stained with Hematoxylin and Eodsin, cover slipped, and examined microscopically. Quantitative results were subjected to an analysis of variance and means separated by a Tukey's Test (SYSTAT, Chicago, Ill.).

Results

Rats in all five estrogen treatments showed a significant decrease (P<0.05) in weight gain compared to that in rats in the control (C) group (Table 3). The (+)-Z-BDDA-treated rats gained more (P<0.05) weight than the estradiol-treated, (−)-Z-BDDA-treated, (−)-HAA-treated, and (+)-HAA-treated rats. The (−)-Z-BDDA-treated rats had the lowest weight change, and was lower (P<0.05) than that in the control, estradiol-treated, (+)-Z-BDDA-treated, and (+)-HAA-treated groups.

Prostate weights as a percentage of bodyweight were lower (P<0.05) than that in controls in all five estrogen treatments (Table 3). The weights of testes and seminal vesicles as a percentage of bodyweight were lower (P<0.05) than that of control rats in the estradiol-treated, (−)-Z-BDDA-treated, (−)-HAA-treated, and (+)-HAA-treated rats (Table 1). The (+)-Z-BDDA-treated rats did not have significantly smaller testes or seminal vesicles as a percentage of bodyweight, although gross testes weights unadjusted for bodyweight were lighter (P<0.05) than those in control rats (data not shown). There were no obvious signs of gynecomastia in any of the rats.

TABLE 3

The effects of (−)- and (+)-Z-bisdehydrodoisynolic acids (BDDA), (−)- and (+)-hydroxyallenolic acid (HAA), and (+)-17β-estradiol (E) on metabolic and reproductive parameters in male rats on treatment for 6 weeks*

| Treatment | Body Weight (g) | Testis Weight as % Body Weight | Prostate Weight as % Body Weight | Seminal Vesicle Weight as % Body Weight |
|---|---|---|---|---|
| vehicle[†] | 336.3 ± 4.9 | 1.14 ± 0.05 | 0.16 ± 0.02 | 0.21 ± 0.03 |
| E[¶] | 207.2 ± 4.6[1] | 0.49 ± 0.13[1,4] | 0.05 ± 0.00[1] | 0.02 ± 0.00[1] |
| (−)-BDDA[¶] | 166.5 ± 4.5[1,2,4] | 0.31 ± 0.02[1,4] | 0.08 ± 0.00[1] | 0.06 ± 0.02[4] |
| (+)-BDDA[¶] | 234.8 ± 10.1[1,2] | 0.98 ± 0.15 | 0.05 ± 0.01[1] | 0.23 ± 0.12[2] |
| (−)-HAA[¶] | 180.9 ± 4.5[1,2,4] | 0.31 ± 0.01[1,4] | 0.08 ± 0.01[1] | 0.04 ± 0.00[1,4] |
| (+)-HAA[¶] | 196.2 ± 5.2[1,4,5] | 0.38 ± 0.02[1,4] | 0.08 ± 0.01[1] | 0.10 ± 0.04 |

*All values are the mean ± SEM, n = 10 animals/treatment (~7 weeks of age).
[†]10% ethanol-90% olive oil solution.

TABLE 3-continued

The effects of (−)- and (+)-Z-bisdehydrodoisynolic acids (BDDA), (−)- and (+)-hydroxyallenolic acid (HAA), and (+)-17β-estradiol (E) on metabolic and reproductive parameters in male rats on treatment for 6 weeks*

| Treatment | Body Weight (g) | Testis Weight as % Body Weight | Prostate Weight as % Body Weight | Seminal Vesicle Weight as % Body Weight |
| --- | --- | --- | --- | --- |

*Treatment groups received the compound (0.1 ug/g of body weight) in 10% ethanol-90% olive oil solution.
[1]significantly different from vehicle ($p < 0.05$); [2]significantly different from estradiol ($p < 0.05$); [3]significantly different from (−)-BDDA ($p < 0.05$); [4]significantly different from (+)-BDDA ($p < 0.05$); [5]significantly different from (−)-HAA ($p < 0.05$).

Histological examination of the prostate showed normal alveoli in the control and (+)-Z-BDDA-treated rats, with the tubules and alveoli being slightly smaller only in the (+)-Z-BDDA-treated rats (FIGS. 4a–f). However, the alveoli showed significant degrees of atrophy in the other four treatments, with the (−)-HAA-treated rats displaying the largest degree of atrophy. In the testis, spermatogenesis and Leydig cells were normal in the control and (+)-Z-BDDA-treated rats, but were severely attenuated in rats in the other four groups (FIGS. 5a–f). Rats in these four treatment groups had spermatogenesis halted in late meiosis, early spermiogenesis. The estradiol-treated rats showed spermatogenesis halted at round (Golgi phase) spermatids, and Leydig cells were small. The (−)-Z-BDDA-treated rats were halted primarily at the secondary spermatocyte phase, with a few spermatogenic cells reaching round spermatid. The (−)-Z-BDDA-treated rats also had severely atrophied Leydig cells, the smallest of all the treatments. The (−)-HAA-treated rats were also halted at round spermatid, with a few reaching cap phase. The (+)-HAA-treated rats were halted at round spermatid, with a few spermatogenic cells showing elongation (acrosome phase). Both HAA-treated groups had smaller Leydig cells than control and (+)-Z-BDDA-treated rats.

Conclusions

These results demonstrate that the estrogenic carboxylic acids BDDA and HAA significantly reduce the size of the prostate in post-pubertal male rats, and suggests their use in the treatment of prostatic disease. This phenomenon may occur via an estrogen-induced apoptotic mechanism. Treatment with the (+)-Z-BDDA enantiomer resulted in a different effect from that observed with the other estrogenic compounds in that testis size and more importantly spermatogenesis and Leydig cell function, was not compromised. The other estrogens used in this study significantly shrank the testes, and decreased its gametic and endocrine function. As in the testes, (+)-Z-BDDA also did not significantly shrink the seminal vesicles. The observation that (+)-Z-BDDA shrinks the prostate without appreciably affecting the testes or seminal vesicles is novel among estrogenic compounds, and may be indicative of selective estrogen receptor modulation (SERM) activity in males. SERM activity has been reported in the female, with compounds such as tamoxifen, nafoxidine, and raloxifene, but not in males. This differential effect of (+)-Z-BDDA also appears to be dependent on dose, since previous studies have shown that a dose 25 times higher (2.5 μg/g bodyweight) shrank the testis, similar to the effect of estradiol and (−)-Z-BDDA. Note Example 2, above, and Banz, W J, T A Winters, Y-Q Hou, S R Adler, and C Y Meyers. "Comparative Effects of the Selective Estrogen Receptor Modulators (−)-, (+)-, and (±)-Z-Bisdehydrodoisynolic Acids on Metabolic and Reproductive Parameters in Male and Female Rats." Horm Metab Res 30:730–736 (1998).

Since the effects of the BDDA and HAA estrogenic carboxylic acids were observed in intact, non-castrate male rats, the present data suggest clinical applications for these or similar compounds in treating males with prostatic disease. These applications could be alone or in combination with other treatments or therapies. The (−)-Z-BDDA and both HAA enantiomers appear to be useful in treating severe prostatic carcinoma since they cause atrophy of the prostate, and probably decrease the androgen secretion of the testis, which is indicative of the atrophy of the Leydig cells. Androgens exacerbate the division and metastasis of prostatic cancer cells. Gudziak, M R, and A Y Smith. "Hormonal Therapy for Stage D Cancer of the Prostate" West J Med 160:351–359 (1994). The BDDA compounds, and possibly the HAA compounds, may have advantages over other estrogen therapies in that they also lower certain cardiovascular risk factors. Note Example 2, above, and Banz, W J, T A Winters, Y-Q Hou, S R Adler, and C Y Meyers. "Comparative Effects of the Selective Estrogen Receptor Modulators (−)-, (+)-, and (±)-Z-Bisdehydrodoisynolic Acids on Metabolic and Reproductive Parameters in Male and Female Rats." Horm Metab Res 30:730–736 (1998). Other estrogen therapies have well-documented cardiovascular side effects. Jacobi, G H. "Hormonal Treatment of Metastatic Carcinoma." In: The Prostate, pp.119–128.(J M Fitzpatrick and R J Krane, eds., Churchill Livingstone, New York, N.Y. 1989). In addition to prostate cancer, (+)-Z-BDDA appears to have utility in the treatment of benign prostate hypertrophy (BPH) since the prostate is reduced without compromising spermatogenesis and/or androgen production by the testes. In addition, even though (+)-Z-BDDA shrank the prostate, histological analysis indicates that the exocrine function of this accessory gland is not appreciably compromised. The exocrine function of the seminal vesicles with (+)-Z-BDDA is probably also unaffected. Therefore, together with no effect on spermatogenesis, semen production should not be affected.

Other applications of these and related estrogenic carboxylic acids suggested by the present data include treatment of other androgen-responsive physiological or pathological conditions, a method of male birth control, and a means for chemical castration in males.

Example 5

Effects of Z-Bisdehydrodoisynolic Acids on Antioxidant Capacity in an Oxidized LDL Lag Time Assay The effects of several synthetic and environmental estrogens, i.e., (+)- and (−)-Z-BDDA, (+)-hydroxyvallestril (allenolic acid) and (−)-hydroxyvallestril (allenolic acid), genistein (soy phytoestrogen), daidzein (soy phytoestrogen), 4-hydroxy-tamoxifen, and estradiol (E2), on antioxidant capacity in an oxidized LDL lag time assay were compared in order to assess the antioxidant activity of these compounds.

Experiments were carried out on dialyzed LDL collected from four fasted persons. The LDL was used within 10 days of dialysis. The oxidizing agent was 3 μM $Cu_2SO_4$; phosphate buffered saline was used to control pH, and all drugs were dissolved in ethanol; final concentrations of each drug in the assays were $10^{-4}$, $10^{-5}$, $10^{-6}$, and $10^{-7}$ M. The combined results are shown in FIG. 6.

Relative to the LDL/Cu curve, the (+)- and (−)-Z-BDDA curves were shifted to the right and somewhat flattened (data not shown). This shift in lag time to the right and flattening of the curves indicates that the Z-BDDAs exhibited significant antioxidant activity. Similar effects were also observed in the case of (+)-allenolic acid, (−)-allenolic acid, and 4-hydroxytamoxifen. Less antioxidant activity was observed with genistein and daidzein. Estradiol exhibited very little antioxidant activity under these conditions (data not shown).

The results indicate that (+)- and (−)-Z-BDDA, (+)- and (−)-hydroxyvallestril, and 4-hydroxytamoxifen were the most potent antioxidants.

Taken together, the results presented in Examples 2–5 suggest that the non-steroidal, estrogenically active carboxylic acids of the present invention can be used in efficacious treatment programs for endocrine- and non-endocrine responsive conditions in males and females, e.g., prostatic disease, hormone-responsive cancers, osteoporosis, therapeutic applications for pre- and post-menopausal women, Alzheimer's disease, male pattern baldness, and as fertility (anti-atresia) and anti-fertility agents. These results further suggest clinical applications for the compounds disclosed herein, as well as appropriate derivatives thereof, in males at risk for cardiovascular disease via decreased oxidation of LDL, for reduction of cholesterol, blood glucose, and body weight, and to achieve positive alterations in body fat distribution. These results also suggest methods for treating or preventing prostatic diseases including benign prostate hyperplasia and other related conditions, androgen-responsive pathological conditions in males, and methods for male birth control and chemical castration, employing estrogenic carboxylic acids.

One-Pot Asymmetric Synthesis of n(+)- and (−)-3-[2-(6-Methoxynaphthyl)]-2,2-dimethylpentanoic Acid Esters In addition to compounds, compositions, and methods for treating diseases, symptoms, and conditions responsive to the compounds disclosed herein, the present invention also provides new synthetic methods for preparing certain of these compounds. In particular, the present invention provides a direct one-pot synthesis to produce esters of 3-[2-(6-methoxynaphthyl)]-2,2-dimethylpentanoic acid (Scheme 4) from commercially available starting material. These esters can then be easily hydrolyzed under basic or acidic conditions to give 2 or 3. Although there are three reaction steps in this synthetic route, separation of intermediates is unnecessary, lowering the cost of production by saving chemicals and manpower, and increasing product yield.

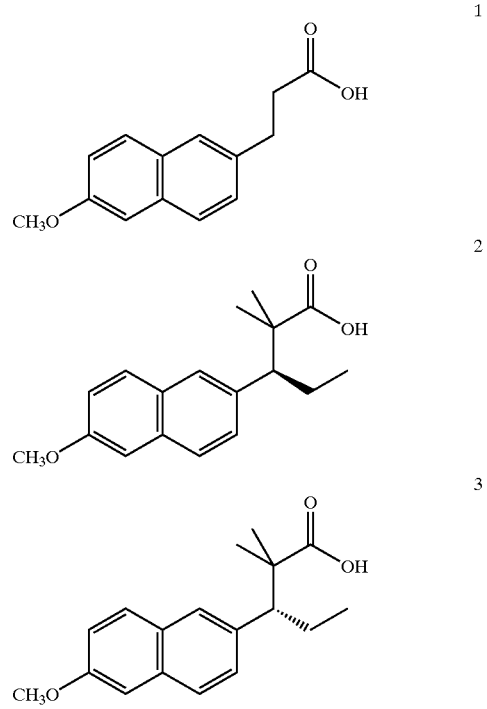

When a chiral R* group is used (Scheme 4), an asymmetric induction in the Michael addition step is expected. By using different chiral R* groups, it is possible to obtain one or the other enantiomer directly from the reaction, eliminating the resolution step and further lowering the cost of production.

Scheme 4

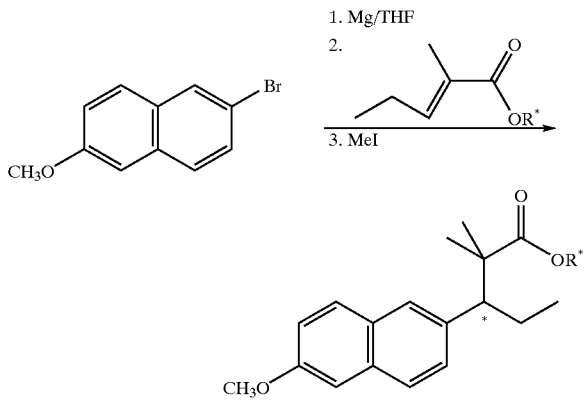

This synthetic scheme can also be used to prepare compounds having other different substituents either on the naphthalene ring or on the propionic acid side chain, as shown in the following structure, 6, where R can be any substituent that does not interfere with the reactions. Examples of R include, but are not limited to, hydrogen, alkyl, alkoxy, alkylthio, alkoxyalkyl, alkylthioalkyl, dialkylamino, halogen, aryl, aryloxy, arylthio, alkanesulfonyl, alkanesulfinyl, silyloxy, protected ketone, and aldehyde (e.g., ketal and acetal).

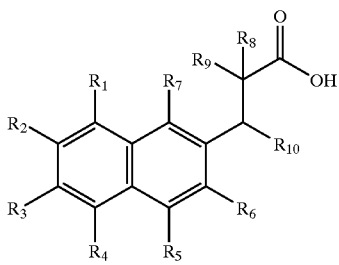

The major starting materials for this synthesis would have the following structures, e.g., 7 and 8, in which X is a halogen atom, for example Cl, Br, or I. Compound 8 is a derivative of acrylic acid, in which Y is a heteroatom, preferably oxygen or nitrogen.

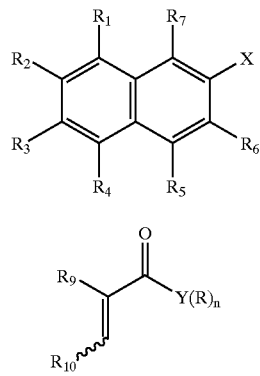

The experiments described below were carried out in ethereal solution starting from 2-bromo-6-methoxynaphthalene at pressures ranging from 0.1 to 100 atmospheres. Other suitable solvents include, for example; ethers, alkanes, and aromatic hydrocarbons. The temperature can range from −100° C. to +150° C. Metals that can be used for these reactiond include magnesium, lithium, sodium, potassium, calcium, palladium, copper, and aluminum. This reaction can also be catalyzed by copper (I) halides alone, or in the presence of other co-calalysts, such as phosphines and boron trifluoride. Chiral auxiliary groups used to induce asymmetric Michael addition include those derived from L- or D-menthol, L- or D-camphor, proline-derived amines and amides. The reaction can also be carried out in the presence of other asymmetric compounds, such as (−)-sparteine, which can induce asymmetric Michael additions under similar reaction conditions.

The starting materials for this synthesis can have the structures illustrated by 7 and 8. The methyl group for the methylation can be derived from methyl iodide, dimethyl sulphate, methyl arenesulfonate, methyl alkanesulfonate, etc.

Example 6

Preparation of L-menthyl trans-2-methyl-2-pentenoate

To a 100-mL round-bottomed flask trans-2-methyl-2-pentenoic acid (11.4 g, 100 mmol) and thionyl chloride (18 mL, 210 mmol) were added. Bubbles evolved from the light-yellow solution immediately. The mixture was stirred at room temperature for 5 min and then heated to reflux for 30 min, during which time the mixture turned brown. Unreacted thionyl chloride was removed by distillation. L-menthol (15.4 g, 99 mmol) was added to the formed acyl chloride and the mixture was heated in a 160° C. oil bath of for 1 hour, at which time the evolution of HCl ceased. The mixture was transferred into a separatory funnel and the flask rinsed with hexanes (100 mL). The hexanes solution was then washed with aqueous $NaHCO_3$ solution and water. Removal of hexanes in vacuo followed by vacuum distillation gave a light yellow oil, 18.7 g; yield: 75%.

Example 7

Preparation of L-menthyl 3-[2-(6-Methoxynaphthyl)]-2,2-dimethylpentanoate

To a 25-mL, three-necked round-bottomed flask equipped with a stir bar and a condenser, freshly ground magnesium turnings (0.29 g, 12.1 mmol) were added. The condenser and the flask were sealed with rubber septa and 5 mL of freshly distilled dry THF was injected. Argon was bubbled into the reaction flask to replace air, followed by dropwise injection of 1,2-dibromoethane (0.2 mL, 2.3 mmol). The reaction mixture started to reflux shortly without external heating. A solution of 2-bromo-6-methoxynaphthalene (Aldrich, 2.37 g, 10 mmol) in dry THF was syringed dropwise into the flask at a speed to maintain the reflux. After all the solution was added, the mixture was heated to maintain reflux for 40 min before being cooled in an ice-water bath. L-menthyl trans-2-methyl-2-pentenoate (2.2 g, 8.7 mmol) was dissolved in 5 mL of dry THF and the solution was injected into the flask. The ice-water bath was removed and the mixture was stirred at room temperature for 1.5 h before methyl iodide (0.62 mL. 10 mmol) was added via a syringe. The reaction proceeded for 15 min before being quenched with water. Product was extracted with ether and the ethereal solution was dried over magnesium sulfate. Removal of ether in vacuo gave a light yellow oil, 3.33 g. Column chromatography (silica gel, hexanes:ethyl acetate=50:1) provided a yellow oil, 2.85 g, whose $^1H$ NMR spectrum showed the presence of L-menthyl 3-[2-(6-methoxynaphthyl)]-2,2-dimethylpentanoate as the major product. Yield by NMR: 77%. The two diastereomers exist in equal amount.

Example 8

Preparation of (−)-8-Phenylmenthyl trans-2-Methyl-2-pentenoate

To a 50-mL round-bottomed flask trans-2-methyl-2-pentenoic acid (2.2 g, 19.3 mmol) and thionyl chloride (5 mL, 58 mmol) were added. Bubbles evolved from the light yellow solution immediately. The mixture was stirred at room temperature for 5 min and then heated at reflux for 30 min. Unreacted thionyl chloride was removed by heating the mixture in an oil bath at 160° C. (−)-8-Phenylmenthol (Aldrich, 0.95 g, 4.1 mmol) was added to the acyl chloride and the mixture was heated in an oil bath at 190° C. for 30 min. Dilute aqueous KOH solution was added into the mixture and the product was extracted with ether. Evaporation of ether provided a light brown oil which is further purified by column chromatography (silica gel, hexanes:ether=50:1) to give a light yellow oil, 1.28 g; yield: 94.8%. $^1H$ NMR showed that it was the desired product, but contained some cis isomer, the trans:cis ratio being 5:1.

Example 9

Preparation of (−)-8-Phenylmenthyl 3-[2-(6-Methoxynaphthyl)]-2,2-dimethyl-pentanoate To a 25-mL, three-necked round-bottomed flask equipped with a stir bar and a condenser, freshly ground magnesium turnings (0.171 g, 7.1 mmol) were added. The condenser and the flask were sealed with rubber septa and 5 mL of freshly distilled dry THF was injected. Argon was bubbled into the reaction flask to replace air, followed by dropwise injection of 1,2-dibromoethane (0.18 mL, 2.1 mmol). The reaction mixture started to reflux shortly without external heating. A solution of 2-bromo-6-methoxynaphthalene (1.20 g, 5.1 mmol) in dry THF (10 mL) was syringed dropwise into the flask at a speed to maintain the reflux. After all the solution was added, the mixture was heated to maintain reflux for 45 min before being cooled in an ice-water bath. (−)-8-Phenylmenthyl trans-2-methyl-2-pentenoate (1.27 g, 3.8 mmol) was dissolved in 5 mL of dry THF and the solution was injected into the flask. The ice-water bath was removed and the mixture was stirred at room temperature for 1.5 h before methyl iodide (0.4 mL, 6.4 mmol) was syringed into the flask. After 15 min the reaction was quenched with aqueous $NH_4Cl$ solution. The product was extracted with ether, the ethereal solution was dried over magnesium sulfate, and the ether was removed in vacuo to yield a light-yellow thick oil. Column chromatography (silica gel, hexanes:ethyl acetate=50:1~20:1) provided a yellow oil, 1.04 g, whose $^1H$ NMR spectrum showed that the two diastereomers exist in a ratio of about 1.7:1. Yield: 77% based on reacted starting material.

The present invention thus provides direct, one-pot methods for the asymmetric synthesis of esters of (+)- and (−)-3-[2-(6-methoxynaphthyl)]-2,2-dimethylpentanoic acid and esters of other substituted 3-(2-naphthyl)propionic acids. These esters can be easily hydrolyzed into their corresponding free acids.

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

The contents of each of the references cited herein are hereby incorporated by reference in their entirety.

What is claimed is:

1. A method for treating, inhibiting or delaying the onset of a prostatic condition in a patient suffering from or disposed to said condition, the method comprising administering (+)-Z-bisdehydrodoisynolic acid to said patient in a dosage effective to treat, inhibit or delay said condition.

2. The method of claim 1, wherein said dosage is in the range of from about 10 μg/kg/day to about 10 mg/kg/day.

3. The method of claim 2, wherein said dosage is in the range of from about 10 μg/kg/day to about 1 mg/kg/day.

4. The method of claim 1, wherein said dosage is from about 0.1 μg/kg/day to about 100 mg/kg/day.

5. The method of claim 1, wherein said prostatic condition is selected from the group consisting of prostatitis, benign prostatic hypertrophy, and prostate cancer.

* * * * *